United States Patent
Caplan et al.

(10) Patent No.: US 12,178,502 B2
(45) Date of Patent: Dec. 31, 2024

(54) TISSUE EXPANSION DEVICES, SYSTEMS AND METHODS

(71) Applicant: Fractyl Health, Inc., Lexington, MA (US)

(72) Inventors: Jay Caplan, Belmont, MA (US); Harith Rajagopalan, Wellesley Hills, MA (US); Mark A. Manasas, Lexington, MA (US); Christopher James Kadamus, Jamaica Plain, MA (US); Andrew Coats, Somerville, MA (US); Philip S. Levin, Storrs, CT (US); J. Christopher Flaherty, Nottingham, NH (US)

(73) Assignee: Fractyl Health, Inc., Burlington, MA (US)

( * ) Notice: Subject to any disclaimer, the term of this patent is extended or adjusted under 35 U.S.C. 154(b) by 337 days.

(21) Appl. No.: 17/868,076

(22) Filed: Jul. 19, 2022

(65) Prior Publication Data

US 2022/0354571 A1   Nov. 10, 2022

Related U.S. Application Data

(63) Continuation of application No. 14/515,324, filed on Oct. 15, 2014, now abandoned, which is a
(Continued)

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/0036* (2018.08); *A61B 5/6847* (2013.01);
(Continued)

(58) Field of Classification Search
CPC . A61B 18/1492; A61B 5/0036; A61B 5/6847; A61B 17/12186; A61B 18/1477;
(Continued)

(56) References Cited

U.S. PATENT DOCUMENTS

| 5,084,044 A | 1/1992 | Quint |
| 5,190,540 A | 3/1993 | Lee |

(Continued)

FOREIGN PATENT DOCUMENTS

| CA | 2666661 C | 1/2015 |
| CN | 1771888 A | 5/2006 |

(Continued)

OTHER PUBLICATIONS

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
(Continued)

*Primary Examiner* — Tan-Uyen T Ho
*Assistant Examiner* — Chima U Igboko
(74) *Attorney, Agent, or Firm* — Wolf, Greenfield & Sacks, P.C.

(57) ABSTRACT

A device for expanding tissue comprises at least one fluid delivery tube and at least one fluid delivery element in fluid communication with the at least one fluid delivery tube. The at least one fluid delivery tube comprises a proximal end, a distal end, and a lumen therebetween. The device is constructed and arranged to perform a near full circumferential expansion of luminal wall tissue. Systems and methods are also provided, including a system for expanding tissue layers and treating tissue proximate to the expanded tissue layers.

12 Claims, 19 Drawing Sheets

Related U.S. Application Data continuation of application No. PCT/US2013/037485, filed on Apr. 19, 2013.

(60) Provisional application No. 61/635,810, filed on Apr. 19, 2012.

(51) Int. Cl.
*A61B 17/12* (2006.01)
*A61M 25/00* (2006.01)
*A61M 25/04* (2006.01)
*A61M 29/00* (2006.01)
*A61M 29/02* (2006.01)

(52) U.S. Cl.
CPC ... *A61B 17/12186* (2013.01); *A61M 25/0074* (2013.01); *A61M 25/0084* (2013.01); *A61M 25/04* (2013.01); *A61M 29/00* (2013.01); *A61M 29/02* (2013.01); *A61B 2018/1472* (2013.01); *A61B 18/1477* (2013.01); *A61M 2025/0087* (2013.01); *A61M 2025/0089* (2013.01); *A61M 2025/009* (2013.01); *A61M 2025/0092* (2013.01)

(58) Field of Classification Search
CPC ... A61B 2018/1472; A61B 5/00; A61B 17/12; A61M 25/0074; A61M 25/0084; A61M 25/04; A61M 29/00; A61M 29/02; A61M 2025/0087; A61M 2025/0089; A61M 2025/009; A61M 2025/0092; A61M 25/00
See application file for complete search history.

(56) References Cited

U.S. PATENT DOCUMENTS

| | | | |
|---|---|---|---|
| 5,423,754 A | 6/1995 | Cornelius et al. | |
| 5,471,982 A | 12/1995 | Edwards et al. | |
| 5,496,311 A | 3/1996 | Abele et al. | |
| 5,515,100 A | 5/1996 | Nogo | |
| 5,542,928 A | 8/1996 | Evans et al. | |
| 5,549,559 A | 8/1996 | Eshel | |
| 5,575,772 A | 11/1996 | Lennox | |
| 5,704,934 A | 1/1998 | Neuwirth et al. | |
| 5,730,719 A | 3/1998 | Edwards | |
| 5,800,484 A | 9/1998 | Gough et al. | |
| 5,827,269 A | 10/1998 | Saadat | |
| 5,859,037 A | 1/1999 | Whitcomb et al. | |
| 5,869,037 A | 2/1999 | Crystal et al. | |
| 5,871,525 A | 2/1999 | Edwards et al. | |
| 5,879,347 A | 3/1999 | Saadat et al. | |
| 5,957,962 A | 9/1999 | Wallsten et al. | |
| 5,964,753 A | 10/1999 | Edwards | |
| 6,009,877 A | 1/2000 | Edwards | |
| 6,053,937 A | 4/2000 | Edwards et al. | |
| 6,056,744 A | 5/2000 | Edwards et al. | |
| 6,066,132 A | 5/2000 | Chen et al. | |
| 6,077,257 A | 6/2000 | Edwards et al. | |
| 6,112,123 A | 8/2000 | Kelleher et al. | |
| 6,293,909 B1 | 9/2001 | Chu et al. | |
| 6,325,777 B1 | 12/2001 | Zadno-Azizi et al. | |
| 6,325,798 B1 | 12/2001 | Edwards et al. | |
| 6,338,726 B1 | 1/2002 | Edwards et al. | |
| 6,358,245 B1 | 3/2002 | Edwards et al. | |
| 6,402,744 B2 | 6/2002 | Edwards et al. | |
| 6,405,732 B1 | 6/2002 | Edwards et al. | |
| 6,409,723 B1 | 6/2002 | Edwards | |
| 6,425,887 B1 | 7/2002 | McGuckin et al. | |
| 6,443,947 B1 | 9/2002 | Marko et al. | |
| 6,544,226 B1 | 4/2003 | Gaiser et al. | |
| 6,673,070 B2 | 1/2004 | Edwards et al. | |
| 6,712,814 B2 | 3/2004 | Edwards et al. | |
| 6,802,841 B2 | 10/2004 | Utley et al. | |
| 6,905,496 B1 | 6/2005 | Ellman et al. | |
| 6,962,587 B2 | 11/2005 | Johnson et al. | |
| 6,974,456 B2 | 12/2005 | Edwards et al. | |
| 7,077,841 B2 | 7/2006 | Gaiser et al. | |
| 7,111,627 B2 | 9/2006 | Stack et al. | |
| 7,122,031 B2 | 10/2006 | Edwards et al. | |
| 7,125,407 B2 | 10/2006 | Edwards et al. | |
| 7,156,860 B2 | 1/2007 | Wallsten | |
| 7,165,551 B2 | 1/2007 | Edwards et al. | |
| 7,241,295 B2 | 7/2007 | Maguire | |
| 7,326,207 B2 | 2/2008 | Edwards | |
| 7,371,215 B2 | 5/2008 | Colliou et al. | |
| 7,387,626 B2 | 6/2008 | Edwards et al. | |
| 7,422,587 B2 | 9/2008 | Bek et al. | |
| 7,507,234 B2 | 3/2009 | Utley et al. | |
| 7,507,238 B2 | 3/2009 | Edwards et al. | |
| 7,530,979 B2 | 5/2009 | Ganz et al. | |
| 7,556,628 B2 | 7/2009 | Utley et al. | |
| 7,585,296 B2 | 9/2009 | Edward et al. | |
| 7,632,268 B2 | 12/2009 | Utley et al. | |
| 7,632,291 B2 | 12/2009 | Stephens et al. | |
| 7,648,500 B2 | 1/2010 | Edwards et al. | |
| 7,758,623 B2 | 7/2010 | Dzeng et al. | |
| 7,762,977 B2 | 7/2010 | Porter et al. | |
| 7,947,038 B2 | 5/2011 | Edwards | |
| 7,959,627 B2 | 6/2011 | Utley et al. | |
| 7,993,336 B2 | 8/2011 | Jackson et al. | |
| 7,997,278 B2 | 8/2011 | Utley et al. | |
| 8,012,149 B2 | 9/2011 | Jackson et al. | |
| 8,066,689 B2 | 11/2011 | Mitelberg et al. | |
| 8,152,803 B2 | 4/2012 | Edwards et al. | |
| 8,177,853 B2 | 5/2012 | Stack et al. | |
| 8,192,426 B2 | 6/2012 | Stern et al. | |
| 8,251,992 B2 | 8/2012 | Utley et al. | |
| 8,273,012 B2 | 9/2012 | Wallace et al. | |
| 8,323,229 B2 | 12/2012 | Shin et al. | |
| 8,364,237 B2 | 1/2013 | Stone et al. | |
| 8,377,055 B2 | 2/2013 | Jackson et al. | |
| 8,486,005 B2 | 7/2013 | Yodfat et al. | |
| 8,641,711 B2 | 2/2014 | Kelly et al. | |
| 8,740,894 B2 | 6/2014 | Edwards | |
| 8,790,705 B2 | 7/2014 | Geigle et al. | |
| 9,364,283 B2 | 6/2016 | Utley et al. | |
| 9,555,020 B2 | 1/2017 | Pasricha et al. | |
| 9,615,880 B2 | 4/2017 | Gittard et al. | |
| 9,757,535 B2 | 9/2017 | Rajagopalan et al. | |
| 9,844,641 B2 | 12/2017 | Rajagopalan et al. | |
| 10,232,143 B2 | 3/2019 | Rajagopalan et al. | |
| 10,299,857 B2 | 5/2019 | Rajagopalan et al. | |
| 10,349,998 B2 | 7/2019 | Levin et al. | |
| 10,610,663 B2 | 4/2020 | Rajagopalan et al. | |
| 10,765,474 B2 | 9/2020 | Kadamus et al. | |
| 10,864,352 B2 | 12/2020 | Rajagopalan et al. | |
| 10,869,718 B2 | 12/2020 | Rajagopalan et al. | |
| 10,980,590 B2 | 4/2021 | Rajagopalan et al. | |
| 10,987,149 B2 | 4/2021 | Rajagopalan et al. | |
| 2002/0013581 A1 | 1/2002 | Edwards et al. | |
| 2002/0077594 A1 | 6/2002 | Chien et al. | |
| 2002/0115992 A1* | 8/2002 | Utley | A61B 18/1492 606/41 |
| 2002/0192162 A1* | 12/2002 | Green | A61P 13/08 424/9.4 |
| 2003/0040804 A1 | 2/2003 | Stack et al. | |
| 2003/0093072 A1 | 5/2003 | Friedman | |
| 2003/0153905 A1 | 8/2003 | Edwards et al. | |
| 2003/0208197 A1 | 11/2003 | Wood | |
| 2003/0233065 A1 | 12/2003 | Steward et al. | |
| 2004/0082859 A1 | 4/2004 | Schaer | |
| 2004/0087936 A1 | 5/2004 | Stern et al. | |
| 2004/0133256 A1 | 7/2004 | Callister | |
| 2004/0148034 A1 | 7/2004 | Kagan et al. | |
| 2004/0204768 A1 | 10/2004 | Geitz | |
| 2004/0215180 A1 | 10/2004 | Starkebaum et al. | |
| 2004/0215296 A1 | 10/2004 | Ganz et al. | |
| 2004/0220559 A1 | 11/2004 | Kramer et al. | |
| 2005/0096638 A1 | 5/2005 | Starkebaum et al. | |
| 2005/0154386 A1 | 7/2005 | West et al. | |
| 2005/0165437 A1 | 7/2005 | Takimoto | |
| 2005/0171524 A1 | 8/2005 | Stern et al. | |
| 2005/0192652 A1 | 9/2005 | Cioanta et al. | |
| 2005/0203489 A1 | 9/2005 | Saadat et al. | |

(56) References Cited

U.S. PATENT DOCUMENTS

| | | |
|---|---|---|
| 2005/0222558 A1 | 10/2005 | Baxter et al. |
| 2005/0245943 A1 | 11/2005 | Zvuloni et al. |
| 2005/0251116 A1 | 11/2005 | Steinke et al. |
| 2005/0273090 A1 | 12/2005 | Nieman et al. |
| 2006/0070631 A1* | 4/2006 | Scopton ............. A61B 17/3478 128/898 |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0247683 A1 | 11/2006 | Danek et al. |
| 2006/0259030 A1 | 11/2006 | Utley et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van et al. |
| 2008/0177135 A1 | 7/2008 | Muyari et al. |
| 2008/0207994 A1 | 8/2008 | Gonon |
| 2008/0243112 A1 | 10/2008 | De |
| 2008/0275445 A1 | 11/2008 | Kelly et al. |
| 2008/0319504 A1 | 12/2008 | Loushin et al. |
| 2009/0012469 A1 | 1/2009 | Nita |
| 2009/0012512 A1 | 1/2009 | Utley et al. |
| 2009/0012518 A1 | 1/2009 | Utley et al. |
| 2009/0018533 A1 | 1/2009 | Perkins et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0234840 A1 | 9/2010 | Jackson et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1 | 7/2011 | Iwata et al. |
| 2011/0319809 A1 | 12/2011 | Smith |
| 2012/0004654 A1 | 1/2012 | Jackson et al. |
| 2012/0016364 A1 | 1/2012 | Mayse et al. |
| 2012/0059364 A1 | 3/2012 | Baust et al. |
| 2012/0197245 A1 | 8/2012 | Burnett et al. |
| 2012/0271277 A1 | 10/2012 | Fischell et al. |
| 2012/0271301 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0310200 A1 | 10/2016 | Wang |
| 2016/0354144 A1 | 12/2016 | Caplan et al. |
| 2017/0007324 A1 | 1/2017 | Kadamus et al. |
| 2017/0014596 A1 | 1/2017 | Rajagopalan et al. |
| 2017/0191035 A1 | 7/2017 | Sia et al. |
| 2017/0333122 A1 | 11/2017 | Rajagopalan et al. |
| 2018/0193590 A1 | 7/2018 | Rajagopalan et al. |
| 2018/0221622 A1 | 8/2018 | Rajagopalan et al. |
| 2020/0001047 A1 | 1/2020 | Rajagopalan et al. |
| 2020/0060758 A1 | 2/2020 | Rajagopalan et al. |
| 2020/0060942 A1 | 2/2020 | Rajagopalan et al. |
| 2020/0138505 A1 | 5/2020 | Levin et al. |
| 2020/0155217 A1 | 5/2020 | Morneau et al. |
| 2020/0261144 A1 | 8/2020 | Caplan et al. |
| 2020/0305972 A1 | 10/2020 | Kadamus et al. |
| 2020/0405388 A1 | 12/2020 | Rajagopalan et al. |
| 2021/0008336 A1 | 1/2021 | Rajagopalan et al. |
| 2021/0085390 A1 | 3/2021 | Kadamus et al. |
| 2021/0137995 A1 | 5/2021 | Rajagopalan et al. |
| 2021/0307816 A1 | 10/2021 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2004180934 A | 7/2004 |
| JP | 2005007161 A | 1/2005 |
| JP | 2006509536 A | 3/2006 |
| JP | 2006136726 A | 6/2006 |
| JP | 2007502690 A | 2/2007 |
| JP | 2008515464 A | 5/2008 |
| JP | 2008173369 A | 7/2008 |
| JP | 2010142661 A | 7/2010 |
| JP | 2010533036 A | 10/2010 |
| JP | 2011516131 A | 5/2011 |
| JP | 2011517599 A | 6/2011 |
| JP | 2011218189 A | 11/2011 |
| JP | 2013543423 A | 12/2013 |
| JP | 2014503256 A | 2/2014 |
| KR | 20080013945 A | 2/2008 |
| KR | 100820497 B1 | 4/2008 |
| WO | WO-9418896 A1 | 9/1994 |
| WO | WO-9912489 A2 | 3/1999 |
| WO | WO-0207628 A2 | 1/2002 |
| WO | WO-02058577 A1 | 8/2002 |
| WO | WO-02096327 A2 | 12/2002 |
| WO | WO-02102453 A2 | 12/2002 |
| WO | WO-03033045 A2 | 4/2003 |
| WO | WO-03092609 A2 | 11/2003 |
| WO | WO-2004064600 A2 | 8/2004 |
| WO | WO-2006020370 A2 | 2/2006 |
| WO | WO-2007044244 A2 | 4/2007 |
| WO | WO-2007067919 A2 | 6/2007 |
| WO | WO-2008002654 A2 | 1/2008 |
| WO | WO-2010042461 A1 | 4/2010 |
| WO | WO-2010125570 A1 | 11/2010 |
| WO | WO-2011060301 A1 | 5/2011 |
| WO | WO-2012009486 A2 | 1/2012 |
| WO | WO-2012099974 A2 | 7/2012 |
| WO | WO-2013130655 A1 | 9/2013 |
| WO | WO-2013134541 A2 | 9/2013 |
| WO | WO-2013159066 A1 | 10/2013 |
| WO | WO-2014022436 A1 | 2/2014 |
| WO | WO-2014026055 A1 | 2/2014 |
| WO | WO-2014055997 A1 | 4/2014 |
| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |

(56) References Cited

FOREIGN PATENT DOCUMENTS

| | | |
|---|---|---|
| WO | WO-2018089773 A1 | 5/2018 |
| WO | WO-2019018362 A1 | 1/2019 |
| WO | WO-2019136240 A1 | 7/2019 |

OTHER PUBLICATIONS

Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
Co-pending U.S. Appl. No. 17/096,855, inventors Rajagopalan; Harith et al., filed Nov. 12, 2020.
Co-pending U.S. Appl. No. 202017095108, inventors Rajagopalan; Harith et al., filed Nov. 11, 2020.
EP12736438.8 The Extended European Search Report dated Nov. 22, 2016.
EP14844285.8 The Extended European Search Report dated Apr. 25, 2017.
EP20150391.9 The Extended European Search Report dated Aug. 20, 2020.
EP20159816.6 The Extended European Search Report dated Aug. 17, 2020.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report and search opinion dated Nov. 25, 2015 for EP Application No. 13777572.2.
European search report with written opinion dated Feb. 1, 2018 for EP Application No. 15822378.
European search report with written opinion dated Dec. 2, 2016 for EP Application No. 14807116.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 19 for U.S. Appl. No. 14/609,332.
Final Office action dated Jul. 10, 2019 for U.S. Appl. No. 15/274,948.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
Grikscheit, et al. Tissue-engineered small intestine improves recovery after massive small bowel resection. Ann Surg., 2004, 240:748-754.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
"International search report and written opinion dated Oct. 23, 2015 for PCT/US2015/040775.".
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report dated Dec. 3, 2014 for PCT Application No. US2014/040957.
International search report with written opinion dated Jan. 9, 2018 for PCT/US2017/061074.
Miyawaki, et al. Inhibition of gastric inhibitory polypeptide signaling prevents obesity. Nat Med. Jul. 2002;8(7):738-42. Epub Jun. 17, 2002.
Notice of Allowance dated Jul. 7, 2017 for U.S. Appl. No. 15/274,764.
Notice of Allowance dated Sep. 14, 2017 for U.S. Appl. No. 15/274,809.
Office Action date Jul. 11, 2018 for U.S. Appl. No. 14/917,243.
Office Action date Aug. 9, 2018 for U.S. Appl. No. 14/673,565.
Office action dated Jan. 8, 2018 for U.S. Appl. No. 14/609,334.
Office Action dated Jan. 13, 2017 for U.S. Appl. No. 14/609,332.
Office action dated Feb. 29, 2016 for U.S. Appl. No. 14/609,334.
Office action dated Mar. 7, 2019 for U.S. Appl. No. 13/945,138.
Office Action dated Mar. 7, 2017 for U.S. Appl. No. 15/274,764.
Office Action dated Mar. 7, 2017 for U.S. Appl. No. 15/274,809.
Office action dated Mar. 7, 2019 for U.S. Appl. No. 14/673,565.
Office action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office action dated Mar. 28, 2016 for U.S. Appl. No. 14/673,565.
Office action dated Apr. 4, 2018 for U.S. Appl. No. 15/156,585.
Office action dated May 18, 2018 for U.S. Appl. No. 14/956,710.
Office Action dated May 31, 2017 for U.S. Appl. No. 15/274,764.
Office action dated Jun. 6, 2019 for U.S. Appl. No. 15/683,713.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
Office action dated Sep. 7, 2018 for U.S. Appl. No. 14/609,332.
Office Action dated Oct. 7, 2016 for U.S. Appl. No. 13/945,138.
Office Action dated Nov. 2, 2017 for U.S. Appl. No. 15/156,585.
"Office action dated Nov. 2, 2018 for U.S. Appl. No. 14/609,334".
Office Action dated Nov. 15, 2016 for U.S. Appl. No. 14/609,334.
Office action dated Nov. 16, 2017 for U.S. Appl. No. 14/609,332.
Office action dated Nov. 30, 2015 for U.S. Appl. No. 13/945,138.
Office action dated Nov. 30, 2017 for U.S. Appl. No. 14/673,565.
"Office action dated Dec. 18, 2018 for U.S. Appl. No. 14/470,503.".
Office action dated Dec. 19, 2017 for U.S. Appl. No. 13/945,138.
PCT/US14/66829 International Search Report dated Feb. 20, 2015.
PCT/US2018/042438 International Search Report dated Sep. 14, 2018.
PCT/US2019/012338 International Search Report dated Apr. 15, 2019.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
Tolman, et al. Spectrum of liver disease in type 2 diabetes and management of patients with diabetes and liver disease. Diabetes care 30.3 (2007): 734-743.

(56) References Cited

OTHER PUBLICATIONS

Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
U.S. Appl. No. 14/470,503, filed Aug. 27, 2014.
U.S. Appl. No. 14/609,332, filed Jan. 29, 2015.
U.S. Appl. No. 14/609,334, filed Jan. 29, 2015.
U.S. Appl. No. 61/603,475, filed Feb. 27, 2012.
U.S. Appl. No. 61/635,810, filed Apr. 19, 2012.
U.S. Appl. No. 61/681,502, filed Aug. 9, 2012.
U.S. Appl. No. 14/917,243 Office Action dated Jun. 5, 2020.
U.S. Appl. No. 13/945,138 Notice of Allowance dated Dec. 22, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Dec. 24, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 13/945,138 Office Action dated Dec. 10, 2019.
U.S. Appl. No. 14/470,503 Notice of Allowance dated Feb. 27, 2019.
U.S. Appl. No. 14/609,334 Office Action dated Jan. 8, 2020.
U.S. Appl. No. 14/956,710 Notice of Allowance dated Jan. 9, 2019.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017 vol. 152, Issue 5, Supplement 1, p. S825. DOI: http://dx.doi.org/10.1016/S0016-5085(17)32851-2.
EP23151399.5 Extended European Search Report dated Aug. 14, 2023.
International search report and written opinion dated Dec. 30, 2013 for PCT Application No. US2013/063753.
Office action dated May 16, 2019 for U.S. Appl. No. 14/515,324.
Office Action dated Jun. 21, 2017 for U.S. Appl. No. 14/515,324.
Office Action dated Sep. 23, 2016 for U.S. Appl. No. 14/515,324.
Office action dated Oct. 4, 2018 for U.S. Appl. No. 14/515,324.
Office action dated Dec. 17, 2015 for U.S. Appl. No. 14/515,324.
Office action dated Dec. 18, 2017 for U.S. Appl. No. 14/515,324.
U.S. Appl. No. 14/515,324 Office Action dated Dec. 4, 2020.
U.S. Appl. No. 14/515,324 Office Action dated Jan. 24, 2022.
U.S. Appl. No. 14/515,324 Office Action dated Mar. 31, 2020.

\* cited by examiner

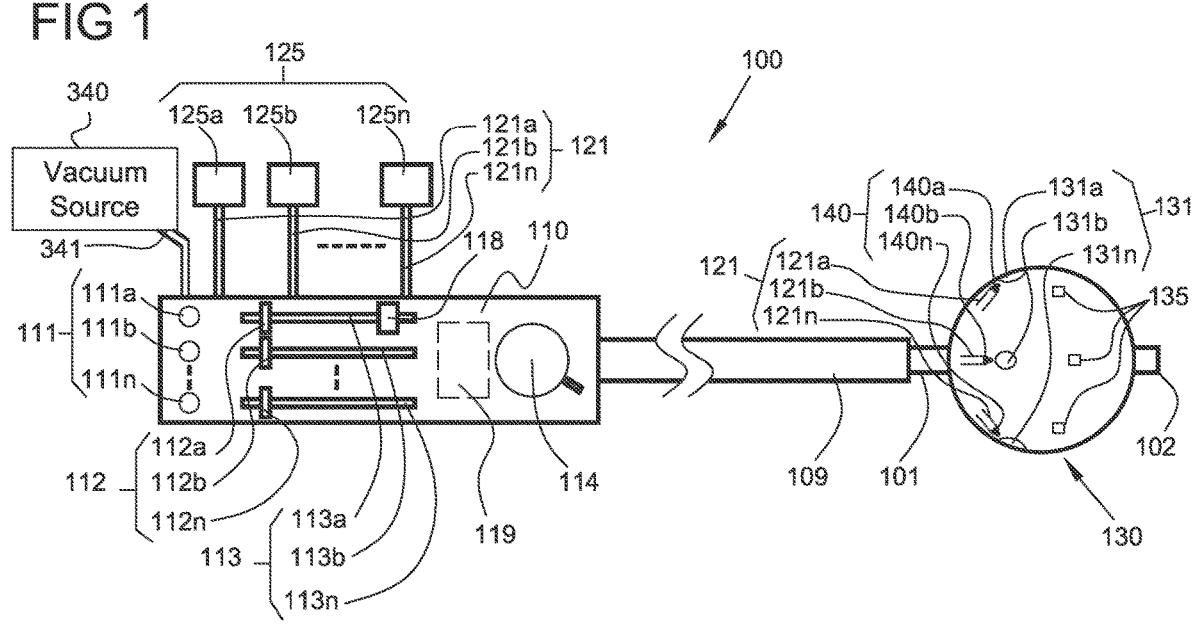
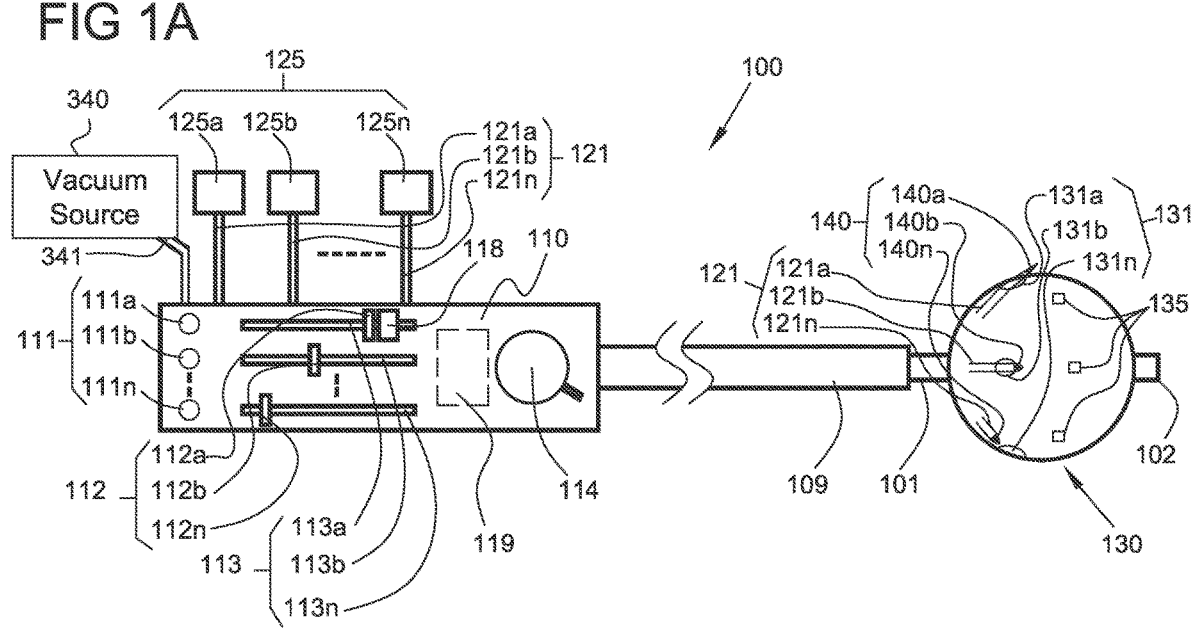

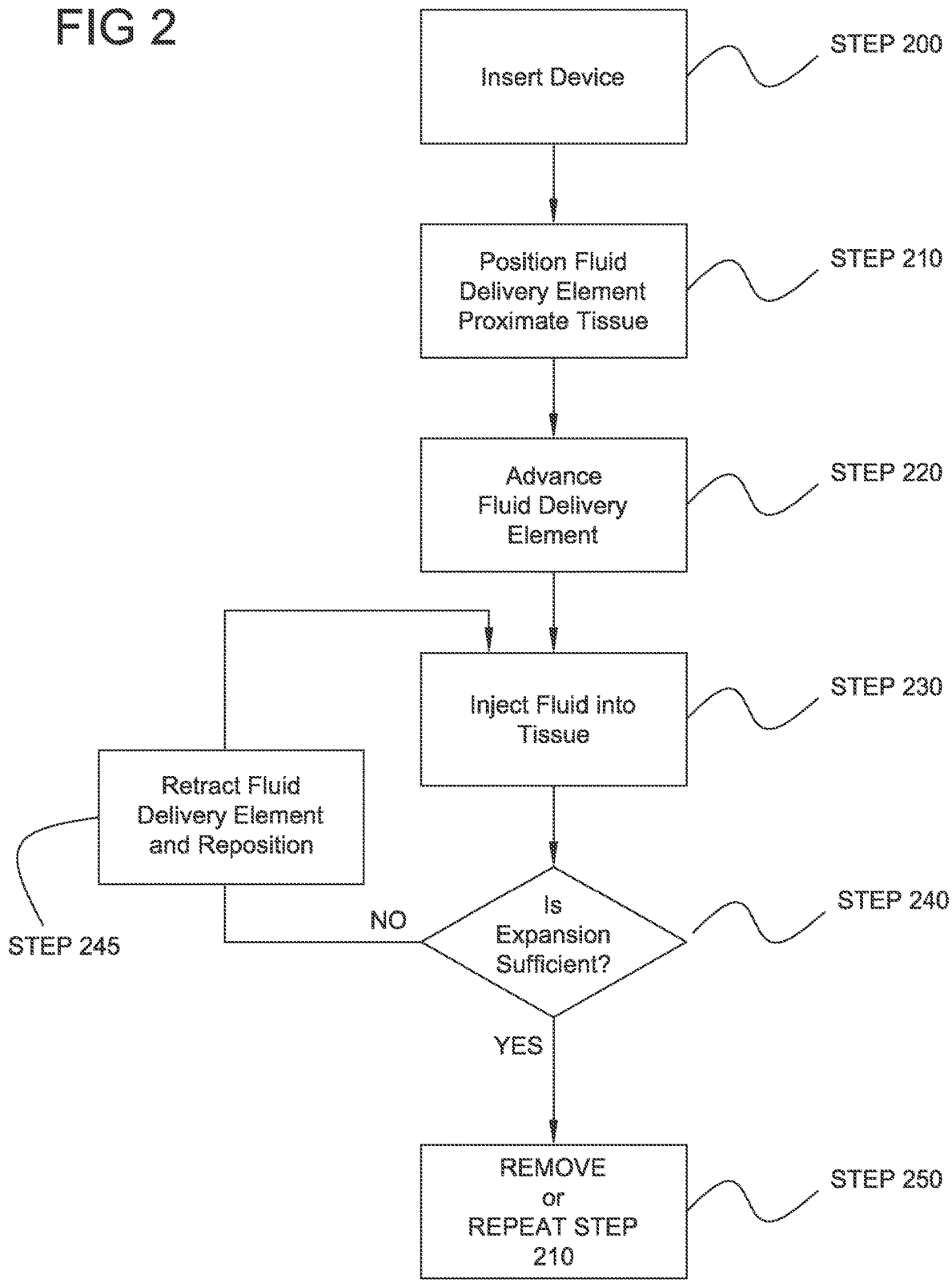

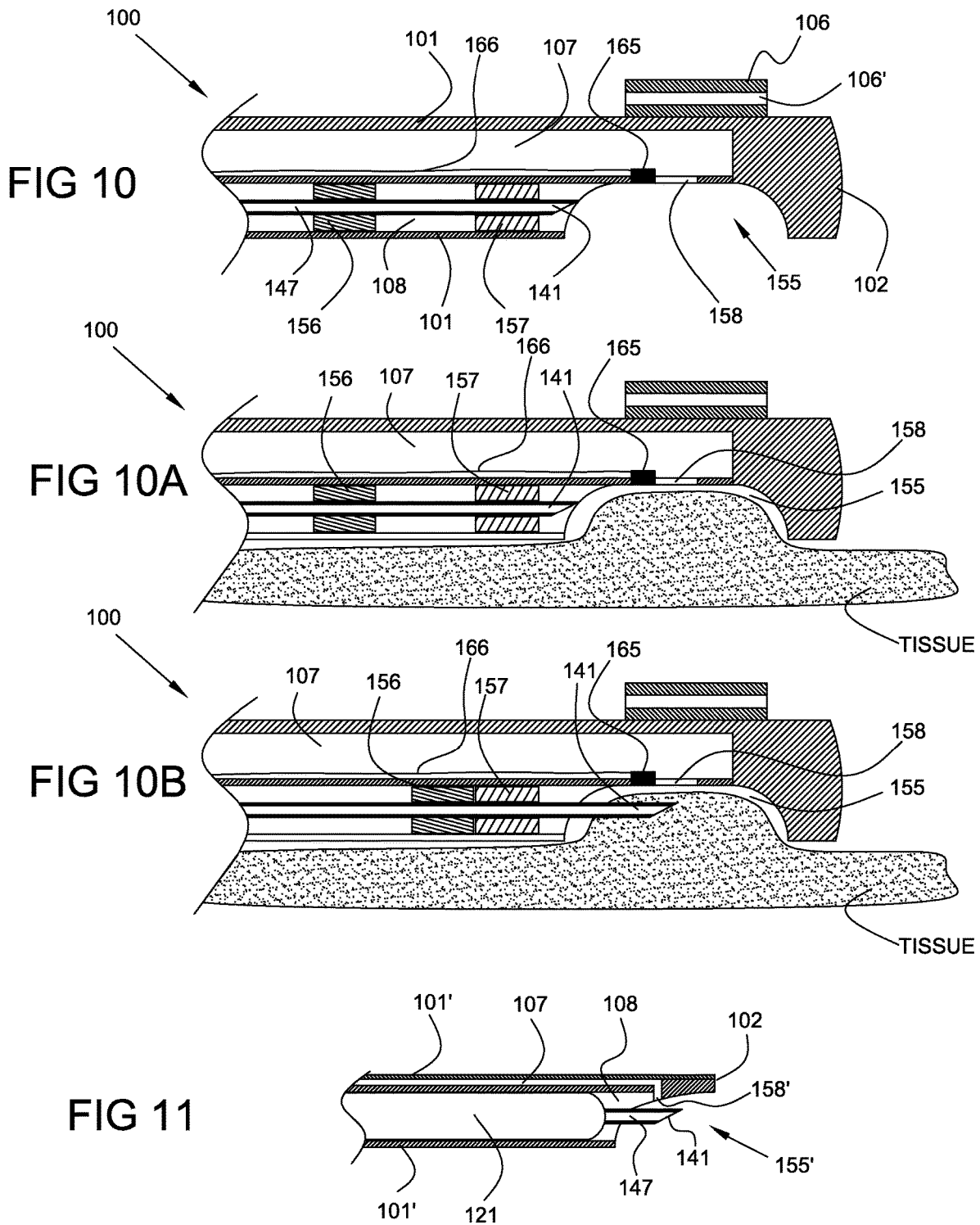

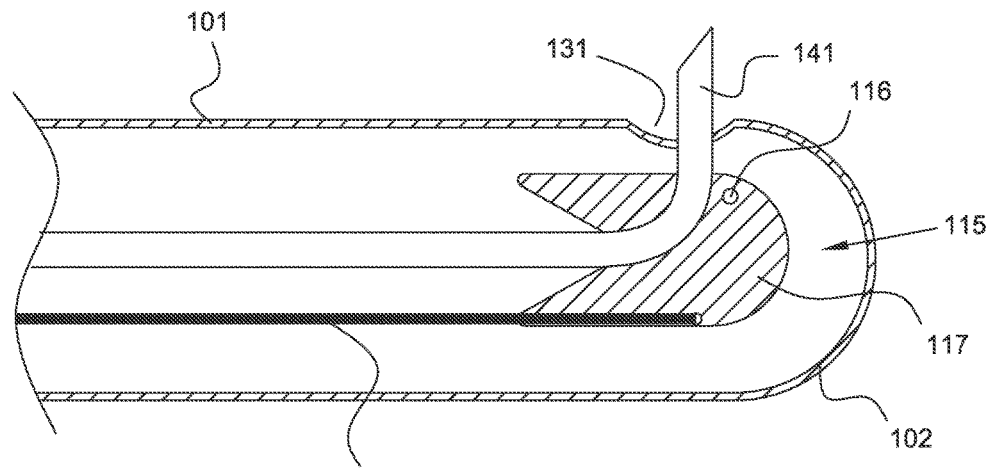
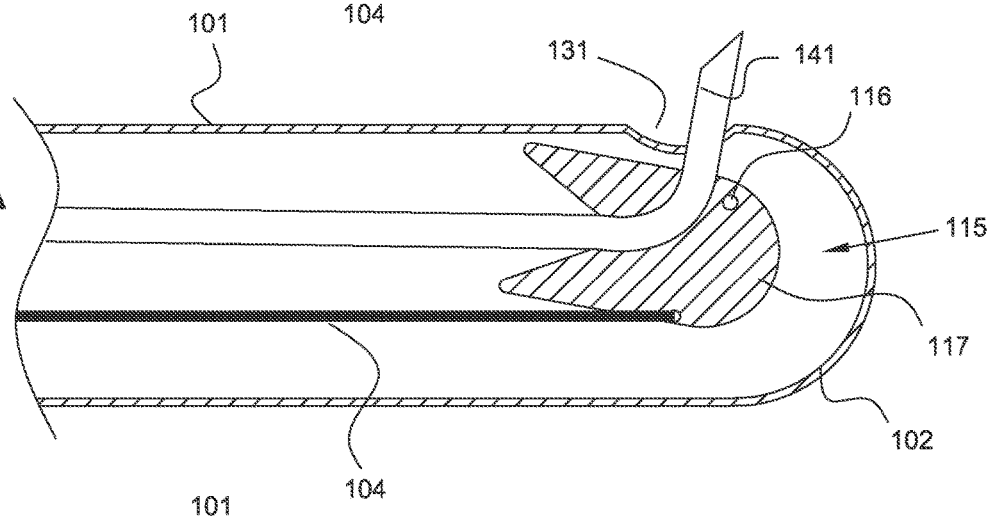
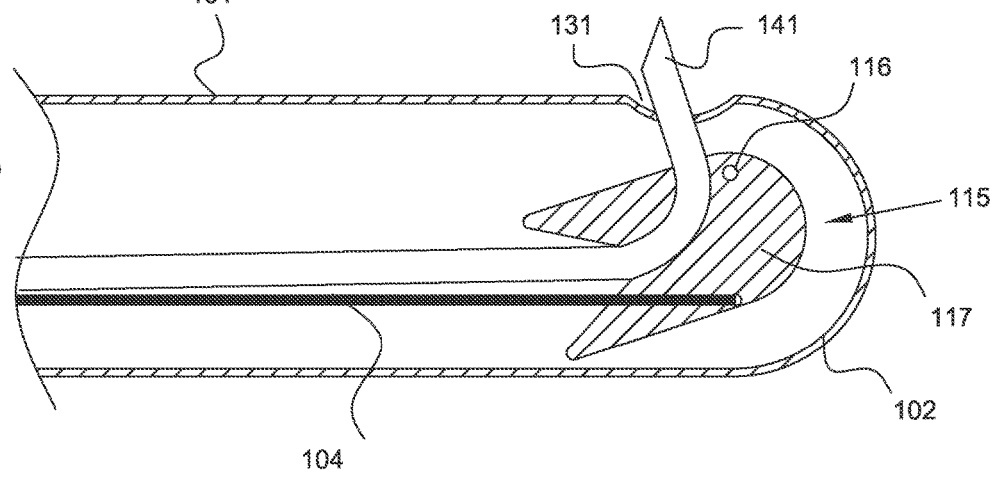

TISSUE EXPANSION DEVICES, SYSTEMS AND METHODS

CROSS-REFERENCE TO RELATED APPLICATIONS

This application is a continuation of U.S. patent application Ser. No. 14/515,324, filed Oct. 15, 2014, which is a continuation of PCT Application No. PCT/US2013/037485, filed Apr. 19, 2013, which claims the benefit of U.S. Provisional Application No. 61/635,810, filed Apr. 19, 2012, the entire content of which is incorporated herein by reference.

This disclosure of this application is also related to those of PCT Application Serial Number PCT/US2012/01739, filed Jan. 18, 2012; and of PCT Application Serial Number PCT/US2013/28082, filed Feb. 27, 2013, the contents of each are incorporated herein by reference in their entirety.

TECHNICAL FIELD

The embodiments disclosed herein relate generally to systems, devices and methods for expanding tissue, particularly one or more layers of gastrointestinal tissue.

BACKGROUND OF THE INVENTION

The field of gastrointestinal endoscopy has for many years focused on diagnostic and therapeutic techniques to observe, modify and remove tissues located in the digestive tract. For example, prior to a procedure to remove or otherwise modify tissue, a method referred to in the art as "lift and cut" involves the injection of saline or other biocompatible solution beneath the submucosa in an attempt to elevate and/or expand the submucosa, thereby changing the geometry to make it suitable for treatment, for example resection of tissue. In some cases, an injection catheter is used to deliver the fluid within the submucosal layer, which does not readily dissipate, throughout the target area, and once the target resection area has been elevated and/or expanded, the tissue can be treated.

However, the current devices, systems and methods for expanding submucosal and other tissue layers are cumbersome, inaccurate, and have a limited effected tissue area. Therefore, there is a need for improved devices, systems and methods for expanding submucosal and other tissue layers that provide simplified use, larger expansion areas, and reduced procedure time.

SUMMARY OF THE INVENTION

According to one aspect of the present inventive concepts, a device for expanding tissue comprises at least one fluid delivery tube comprising a proximal end, a distal end and a lumen therebetween; and at least one fluid delivery element in fluid communication with the at least one fluid delivery tube lumen where the device is configured to expand one or more tissue layers, such as a to perform a near full circumferential expansion of luminal wall tissue.

In some embodiments, the device is configured to perform near full circumferential expansion of luminal wall tissue. The near circumferential expansion can be performed with a single operator step of fluid delivery, for example where the at least one fluid delivery element comprises two or more fluid delivery elements and fluid delivery from the two or more fluid delivery elements occurs simultaneously or sequentially. Alternatively, the near circumferential expansion can be performed with multiple operator steps of fluid delivery.

In some embodiments, the device is configured to narrow a lumen surrounded by luminal wall tissue, for example narrowed to a diameter 85% or less of the diameter prior to luminal wall tissue expansion, or in some cases 75% or less In some embodiments, the device is configured to smooth the inner surface of luminal wall tissue, for example plicae of the gastrointestinal tract.

In some embodiments, the device is configured to deliver a pre-determined volume of fluid into tissue. The volume of fluid delivered can range from approximately 0.5 ml to 4.0 ml which can be delivery between 2 and 10 times. The volume of fluid delivered can range from approximately 1.0 ml to 3.0 ml which can be delivered between 2 and 10 times.

In some embodiments, the device is configured to provide pressure-controlled delivery of fluid into tissue. The device can deliver fluid until a maximum pressure is reached, or until the pressure is above a minimum level.

In some embodiments, the device is configured to expand a first layer of tissue while avoiding expansion of a second, deeper layer of tissue. Conversely, the device can be configured to expand a first layer of tissue while avoiding expansion of a second, more shallow layer of tissue.

In some embodiments, the device is configured cause the at least one fluid delivery element to initially penetrate the plicae of the gastrointestinal tract.

The one or more tissue layers to be expanded can comprise luminal wall tissue. The one or more tissue layers to be expanded can comprise submucosal tissue, for example duodenal submucosal tissue. The device can be configured to avoid expansion of tissue selected from the group consisting of mucosal layer tissue; muscularis layer tissue; serosal layer tissue; and combinations of these. Other types of tissue that can be expanded by the device are selected from the group consisting of a gastrointestinal tissue layer; a duodenal tissue layer; an esophageal tissue layer; a jejunum tissue layer; an ileum tissue layer; a colon tissue layer; a stomach tissue layer; a bladder tissue layer; an oral cavity tissue layer; a uterus tissue layer; and combinations of these.

The at least one fluid delivery element can comprise two or more fluid delivery elements, for example a first and a second fluid delivery element. The first and the second fluid delivery elements can be similar or dissimilar. The first fluid delivery element and the second fluid delivery element can be configured to deliver fluid simultaneously and/or sequentially. The at least one fluid delivery tube can comprise a single fluid delivery tube where the first fluid delivery element and the second fluid delivery element are fluidly connected to the single fluid delivery tube. Alternatively, the at least one fluid delivery tube can comprise at least two fluid delivery tubes where the first fluid delivery element is fluidly connected to a first fluid delivery tube and the second fluid delivery element is fluidly connected to a second fluid delivery tube.

The at least one fluid delivery element can comprise three or more fluid delivery elements positioned in a relatively circumferential array. In some embodiments, the device comprises a support assembly where the three or more fluid delivery elements are positioned on and/or in the support assembly. The support assembly can comprise a support structure selected from the group consisting of: at least one balloon; two or more support arms; a radially deployable structure; and combinations of these. The support assembly can comprise two or more support arms where a first fluid delivery element is positioned proximate a first support arm and wherein a second fluid delivery element is positioned proximate a second support arm. The at least one delivery element can comprise at least four fluid delivery elements where the support assembly comprises at least four support arms, and where a fluid delivery element is positioned proximate each of the four support arms. The support assembly can comprise a radially expandable support assembly that is expandable via a retractable shaft. The support assembly can comprise a support assembly configured to be biased in a radially expanded state, and also configured to be radially compacted. The support assembly can comprise two or more tubes where each of the two or more tubes surrounds a fluid delivery element, for example where the two or more tubes slidingly engage a fluid delivery element. Each of the two or more tubes can comprise an exit port through which a fluid delivery element can be advanced. Each of the two or more tubes can comprise a vacuum port configured to apply tension to tissue. Each of the two or more tubes can comprise an entry port configured to allow tissue to pass through. The support assembly can comprise two or more exit ports through which a fluid delivery element can be advanced and a vacuum can be applied to the two or more exit ports. The support assembly can comprise at least one vacuum port.

The device can further comprise at least one exit port where the at least one fluid delivery element is configured to be operably advanced out of the at least one exit port. The device can be configured to apply a vacuum to the at least one exit port. The device can further comprise an elongate shaft which slidingly receives the at least one fluid delivery tube, and where the at least one exit port is positioned at a side portion of the elongate shaft, and the device can be configured to allow an operator to adjust the trajectory of the at least one fluid delivery element out of the at least one exit port.

The at least one fluid delivery element can comprise an advanceable fluid delivery element. For example, the fluid delivery element can be advanced by an operator. The device can comprise a control configured to advance the at least one fluid delivery element where the control can be positioned on a handle of the device. The control can be configured to allow an operator to modify the advancement of the at least one fluid delivery element. The device can comprise a guide surface configured to cause and/or maintain a predetermined trajectory for the at least one fluid delivery element. The device can comprise a surface positioned such as to limit the advancement of the at least one fluid delivery element. The at least one fluid delivery element can be advanced a fixed distance, for example a distance set by an operator. The distance can range from approximately 1 mm to 10 mm, or from approximately 3 mm to 7 mm. The device can comprise an elongate shaft comprising a recess portion surrounding the at least one fluid delivery tube where the at least one fluid delivery element is configured to advance into the recess portion. The device can comprise an elongate shaft with a distal end surrounding the at least one fluid delivery tube where the at least one fluid delivery element is configured to advance out of the shaft distal end. The at least one fluid delivery element can be resiliently biased in a retracted state, for example via a spring element. The at least one fluid delivery element can comprise a first fluid delivery element and a second fluid delivery element where each of the fluid delivery elements are biased in a retracted state.

The at least one fluid delivery element can comprise at least two fluid delivery elements, each comprising advanceable fluid delivery elements. For example, a first fluid delivery element can be independently advanceable from a second fluid delivery element. Alternatively, the first and second fluid delivery elements can be advanced simultaneously.

The device can further comprise a spring-loaded fluid delivery advancement assembly. The assembly can be configured to be activated by an operator. The assembly can be configured to advance multiple fluid delivery elements, and in some cases, the multiple fluid delivery elements can be advanced independently of one another.

The at least one fluid delivery element can be configured to move laterally as the tissue is expanded.

The at least one fluid delivery element can comprise at least one element selected from the group consisting of; a needle; a water jet; an iontophoretic element; a porous element; and combinations of these. In an embodiment where the at least one fluid delivery comprises a needle, the device can comprise an elongate shaft with a recess where the needle is constructed and arranged to be maintained within the elongate shaft recess. The needle diameter can range from approximately 20 to 35 gauge, for example from approximately 23 to 27 gauge. The needle can comprise a solid tip needle comprising an exit port selected from the group consisting of: at least one side hole; a porous section; and combinations of these. The needle can comprise at least one side hole. The needle can be configured to penetrate through mucosal tissue and into submucosal tissue but not penetrate muscularis tissue. The needle can be configured to penetrate through mucosal tissue and into submucosal tissue but not penetrate serosal tissue. The needle can comprise an exposed length of less than or equal to 10 mm, for example an exposed length less than or equal to 7 mm. The needle can extend from an expandable support, for example an expandable support selected from the group consisting of: a balloon; a cage; one or more radially extending arms; and combinations of these.

The at least one fluid delivery element can comprise a sharpened distal end. The at least one fluid delivery element can comprise a beveled distal end, for example where the bevel angle ranges from 10° and 60° such as a bevel angle of approximately 30°.

The at least one fluid delivery element can comprise a water jet where the water jet can comprise a nozzle configured to cause fluid to penetrate one or more tissue layers.

The device can further comprise fluid configured to be delivered to the tissue through the at least one fluid delivery element. The fluid can be a fluid selected from the group consisting of: a liquid; a gas; and combinations of these. For example, the fluid can be selected from the group consisting of: water; saline such as hypertonic saline; air; $CO_2$; one or more hydrogels; epinephrine; hypertonic dextrose water; hyaluronic acid; glycerol solutions; and combinations of these. The fluid can be one that provides a visual image corresponding to the amount of tissue expansion, for example a fluid selected from the group consisting of: methylene blue or other dye; radiopaque fluid; MR visualizable fluid; ultrasonically visualizable fluid; and combinations of these. The fluid can comprise a magnetic fluid. The fluid can change color as the fluid temperature changes. The fluid can comprise at least two fluids, for example a first fluid with a first reflectance color and a second fluid with a second reflectance color where the device is configured to deliver the first fluid through a first fluid delivery element and the second fluid through a second fluid delivery element. The fluid can comprise a fluid that is heated prior to delivery into tissue. The fluid can comprise a fluid configured to change viscosity after delivery into tissue, for example the fluid can increase or decrease in viscosity after delivery into tissue.

The fluid can comprise a fluid of similar osmolarity to the tissue. The fluid can comprise a fluid configured as an insulator. The fluid can comprise glycerol and saline, for example heated glycerol and saline. The fluid can be configured to provide a bioactive function, for example a function selected from the group consisting of: sclerosant; an anti-inflammatory agent; an anti-microtubule or other mitotic inhibitors; an alkylating agent; an antimetabolite; an anthracycline; a plant alkaloids; a topoisomerase inhibitor; an anti-proliferative; and combinations of these.

The device can further comprise a manipulating assembly configured to manipulate one or more of: tissue; fluid; delivered fluid; and combinations of these. The manipulating assembly can comprise a vacuum port. The vacuum port can comprise a width that is less than or equal to 2.0 mm, or less than or equal to 1.5 mm, or less than or equal to 1.0 mm. The vacuum port can comprise a length that is less than or equal to 5.0 mm, or less than or equal to 4.0 mm, or less than or equal to 3.0 mm. The vacuum port can comprise a width of approximately 1.5 mm and a length of approximate 4.0 mm. The device can further comprise a lumen in fluid communication with the vacuum port. The device can further comprise a vacuum generator in fluid communication with the vacuum port. The vacuum port can be configured to move the tissue toward the at least one fluid delivery element. The device can be configured to apply a vacuum of approximately 5 cmHg to 45 cmHg below atmospheric pressure to the vacuum port, for example a vacuum of approximately 5 cmHg to 20 cmHg below atmospheric pressure to the vacuum port. The device can be configured to allow an operator to adjust the pressure applied at the vacuum port. The manipulating assembly can be configured to prevent motion of a portion of tissue as the at least one fluid delivery element penetrates into that portion of tissue. The manipulating assembly can be configured to prevent motion of a portion of tissue as the at least one fluid delivery element delivers fluid into that portion of tissue. The manipulating assembly can be configured to move fluid previously delivered into tissue, for example via a vacuum and/or via the application of a translating force across the tissue. The manipulating assembly can be configured to direct the flow of fluid being delivered into tissue. The manipulating assembly can comprise one or more components selected from the group consisting of: a balloon; an expandable ring; a vacuum port; a grasper such as a pair of articulating jaws; a radially expandable cage; a radially deployable arm; and combinations of these.

The device can further comprise a luminal sealing element configured to at least partially occlude the lumen of the at least one fluid delivery tube surrounded by the tissue. For example, the luminal sealing element can comprise a balloon positioned proximal to or distal to the at least one fluid delivery element.

The device can further comprise a pressure monitoring assembly configured to monitor pressure prior to, during and/or after expansion of the tissue.

The device can further comprise a diagnostic assembly configured to perform an assessment of the tissue expansion. For example, the diagnostic assembly can assess the amount of tissue expansion; the thickness of one or more tissue layers; the penetration of the at least one fluid delivery element into tissue; and combinations of these. The diagnostic assembly can comprise a visualization assembly. The visualization assembly can be configured to monitor the color density of fluid delivered into tissue. The visualization assembly can comprise a component selected from the group consisting of: a visible light camera; an ultrasound imager; an OCT device; an OCDR device; confocal endomicroscopy via either scanning or structured illumination; and combinations of these. The visualization assembly can further comprise a light emitting source configured to monitor the depth of penetration of the at least one fluid delivery element into tissue. The diagnostic assembly can comprise a tissue analyzer, for example an ultrasonic tissue analyzer configured to provide tissue thickness information. The diagnostic assembly can comprise an impedance measurement element. The diagnostic assembly can be configured to deliver heated and/or chilled fluid and to assess tissue expansion based on a measured change in temperature.

The device can further comprise at least one sensor. The at least one sensor can comprises a sensor selected from the group consisting of: temperature sensor; impedance sensor; optical sensor; pressure sensor; strain gauge; force sensor; and combinations of these. The sensor can be configured to perform a function selected from the group consisting of: quantify or otherwise assess one or more of: amount of tissue expansion; current tissue thickness (e.g. pre, during and/or post expansion); tissue layer thickness; penetration distance of a fluid delivery element; color density of a delivered fluid; impedance of tissue; temperature of tissue such as temperature of tissue that has received a heated or chilled fluid via needle; and combinations of these.

The device can further comprise an expanding element. The expanding element can be configured to minimize migration of fluid delivered to tissue. For example, the expanding element can comprise a balloon. The expanding element can comprise a first balloon and a second balloon where the at least one fluid delivery element is positioned between the first and the second balloon. The expanding element can comprise a tapered profile. The expanding element can comprise a dog-bone profile. The expanding element can comprise at least one recess. The at least one fluid delivery element can be configured to be positioned and/or advanced in the at least one recess. A vacuum port can be positioned in the at least one recess.

The device can further comprise an elongate shaft surrounding the at least one fluid delivery tube.

The at least one fluid delivery element can comprise a first fluid delivery element and a second fluid delivery element where the at least one fluid delivery tube comprises a first fluid delivery tube in fluid communication with the first fluid delivery tube and a second fluid delivery tube in fluid communication with the second fluid delivery tube. The device can further comprise a shaft surrounding the first fluid delivery tube and the second fluid delivery tube and wherein the first fluid delivery tube and the second fluid delivery tube are positioned in a side-by-side arrangement.

The at least one fluid delivery element can comprise at least three fluid delivery elements. The at least one fluid delivery tube can comprise at least three fluid delivery tubes singly connected to the at least three fluid delivery elements. Alternatively, the at least one fluid delivery tube can comprise a single fluid delivery tube where the device further comprises a manifold configured to operably connect the single fluid delivery tube to the first fluid delivery element, the second fluid delivery element and the third fluid delivery element.

The at least one fluid delivery element can comprise at least four fluid delivery elements. The at least one fluid delivery tube can comprise at least four fluid delivery tubes singly connected to the at least four fluid delivery elements. Alternatively, the at least one fluid delivery tube can comprise a single fluid delivery tube where the device further comprises a manifold configured to operably connect the single fluid delivery tube to the first fluid delivery element, the second fluid delivery element, the third fluid delivery element and the fourth fluid delivery element.

In some embodiments, the device is configured to be inserted through an endoscope. In some embodiments, the device is configured to be inserted through a lumen of 13 mm or less, or a lumen of 8 mm or less, or a lumen of 6 mm or less.

In some embodiments, the device comprises a workable insertion length of at least 25 cm, or at least 35 cm, or at least 100 cm, or at least 140 cm.

In some embodiments, the device is configured for over-the-wire delivery into the gastrointestinal tract. The device can comprise a lumen configured to slidingly receive a guidewire. Additionally or alternatively, the device can comprise a sidecar configured to rapid exchange delivery over a guidewire.

The device can further comprise an elongate shaft surrounding the at least one fluid delivery tube wherein the at least one fluid delivery element is configured to be advanced from the elongate shaft, for example where the elongate shaft comprises an endoscope shaft.

The device can further comprise an elongate shaft surrounding the at least one fluid delivery tube and comprising a distal portion and an opening positioned in the distal portion. The at least one fluid delivery element can be positioned in the distal portion opening. The at least one fluid delivery element can be configured to be advanceable into the distal portion opening. The device can be configured to apply a vacuum to the distal portion opening. The distal portion opening can comprise a recess in the elongate shaft distal portion.

According to another aspect of the present inventive concepts, a method comprises providing a tissue expansion device comprising at least one fluid delivery tube comprising a proximal end, a distal end, and a lumen therebetween; and at least one fluid delivery element in fluid communication with the at least one fluid delivery tube lumen; and delivering fluid through the at least one fluid delivery element into a first tissue location to expand one or more layers of tissue.

Delivering fluid through the at least one fluid delivery element into a first tissue location to expand one or more layers of tissue can comprise delivering the fluid via at least two fluid delivery elements simultaneously.

The one or more layers of tissue can be expanded to move an inner layer of tissue toward a treatment element.

The method can further comprise delivering a second volume of fluid. The second volume of fluid can be delivered to the first tissue location, or to a second, different tissue location.

The method can further comprise moving delivered fluid residing in the tissue. The fluid residing in the tissue can be moved as fluid is being delivered through the fluid delivery element.

The method can further comprise applying a force to tissue prior to and/or during the delivering of fluid. The force can be applied by two expandable elements, for example two expandable balloons.

The method can further comprise manipulating the first tissue location and/or tissue proximate the first tissue location prior to delivering the fluid into the first tissue location. The manipulating can comprise applying a vacuum. The at least one fluid delivery element can be advanced into the vacuum manipulated tissue, for example where the at least one fluid delivery element comprises a needle. Alternatively or additionally, the manipulating can comprise grasping the tissue with a tool.

The method can further comprise monitoring the expansion of tissue. For example, the monitoring can comprise monitoring tissue expansion for sufficiency.

The method can further comprise ablating tissue proximate the expanded tissue.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

FIG. 1 is a side view of a tissue expanding device including multiple fluid delivery elements in a retracted state, consistent with the present inventive concepts.

FIG. 1A is a side view of the tissue expanding device of FIG. 1, with the multiple fluid delivery elements advanced, consistent with the present inventive concepts.

FIG. 2 is a flow chart of a method for tissue expansion, consistent with the present inventive concepts.

FIG. 10 is a side sectional view of a distal portion of a tissue expansion device comprising a side recess portion and protected needle exit port, consistent with the present inventive concepts.

FIG. 10A is a side sectional view of the tissue expansion device of FIG. 10 after the device has been positioned proximate tissue, consistent with the present inventive concepts.

FIG. 10B is a side sectional view of the tissue expansion device of FIGS. 10 and 10A after a needle has been axially advanced into the tissue, consistent with the present inventive concepts.

FIG. 11 is a side sectional view of a distal portion of a tissue expansion device comprising an end recess portion and protected needle exit port, consistent with the present inventive concepts.

FIG. 17 is a side sectional view of a distal portion of a tissue expansion device including a fluid delivery element with an operator adjustable needle trajectory guide, consistent with the present inventive concepts.

FIG. 17A is the tissue expansion device of FIG. 17 after the adjustable guide has been rotated to cause the trajectory taken by the needle to tend toward a distal end of the device, consistent with the present inventive concepts.

FIG. 17B is the tissue expansion device of FIG. 17 after the adjustable guide has been rotated to cause the trajectory taken by the needle to tend toward a proximal end of the device, consistent with the present inventive concepts.

DETAILED DESCRIPTION OF THE INVENTION

Figure 3A:
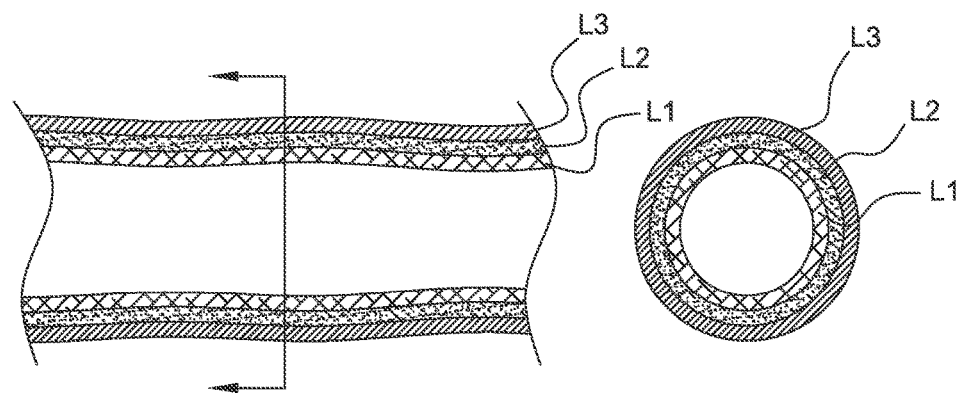
FIGS. 3A, 3B and 3C are a series of sectional side and end views of a segment of luminal wall tissue, prior to, during and after full circumferential tissue expansion, respectively, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

It is an object of the present inventive concepts to provide devices, systems, and methods to safely and effectively expand an area of tissue, such as one or more layers of a portion of tubular or solid tissue, such as tissue of an organ or tissue of the gastrointestinal tract of a patient. The devices and systems of the present inventive concepts include one or more fluid delivery elements, such as needles or water jets configured to deliver one or more fluids to the tissue to be expanded. Needles may comprise hollow or partially hollow needles, such as needles with one or more openings at the distal end and/or at a side wall location. One or more visualization assemblies may be included, such as to allow an operator to visualize or otherwise assess the tissue expansion procedure. One or more tissue manipulation assemblies may be included, such as to apply a force to enhance or otherwise modify the tissue expansion.

In some embodiments, a vacuum or other negative pressure may be used to manipulate tissue and/or to maintain proximity between a portion of a tissue expansion device or assembly, and tissue. This vacuum or other negative pressure can comprise a pressure below another pressure, such as a pressure below the environment of the patient, hereinafter referred to as a "vacuum" or "vacuum pressure". The vacuum may be provided by one or more vacuum sources, such as via one or more operator adjustable vacuum sources.

In some embodiments, the tissue expansion is performed prior to treatment of tissue, such as ablation of a target volume of tissue. The devices and systems of the present invention may further include one or more ablation devices, such as ablation devices configured to treat a layer of tissue above a previously expanded tissue layer, such as to prevent damage to one or more tissue layers below the expanded tissue layer. In these embodiments, the expanded tissue layer acts as a safety volume of tissue, reducing the specificity of the ablation and/or protecting the underlying tissue from damage.

Referring now to FIG. 1, a side view of a device for expanding tissue is illustrated, including multiple fluid delivery elements, consistent with the present inventive concepts. Device 100 includes handle 110, which is fixedly attached to a hollow tube, outer sheath 109, typically a flexible tube made of one or more biocompatible materials. Sheath 109 surrounds and slidingly receives inner shaft 101, also typically a flexible tube made of one or more biocompatible materials. Inner shaft 101 includes distal end 102. In some alternative embodiments, device 100 does not include sheath 109, and inner shaft 101 is fixedly attached to handle 110. Attached on a distal portion of shaft 101 is expandable assembly 130, typically a radially expandable and/or radially compressible assembly such as an inflatable balloon, a flexible basket or cage, or a series of radially deployable arms. In alternative embodiments, assembly 130 can be directed or otherwise brought to tissue through deflection, advancement or other manipulation, with or without expansion, such as is described in reference to FIGS. 6, 7, 8, 9, 10, 11, 12, 14, 15, 16, 17 and 18 herebelow. Expandable assembly 130 is configured to allow one or more fluid delivery elements to be brought in proximity to tissue, such as to penetrate tissue or otherwise be positioned to allow fluid to be delivered to tissue and cause one or more layers of tissues to expand. Expandable assembly 130 can include one or more openings 131, such as openings 131a and 131b through 131n as shown. Assembly 130 can be constructed and arranged to apply force to tissue. Assembly 130 can be constructed and arranged to orient fluid delivery elements 140 and/or openings 131, such as to position openings 131 relatively perpendicular to luminal wall tissue. The tissue may comprise one or more locations within a patient's body, such as tissue comprising a body lumen such as one or more portions of the gastrointestinal tract. Typical tissue locations are described in detail in reference to FIGS. 3A, 3B and 3C herebelow.

Handle 110 can include a varied number of controls and/or groups of controls configured to advance, deploy or otherwise activate one or more assemblies or components of device 100. Typical controls include one or more mechanical and/or electrical controls such as knobs, levers, switches, solenoids and the like. Controls may be connected to electrical wires such as to deliver power to an assembly or component of device 100. Controls may be connected to one or more mechanical linkages such as linkages including advanceable and retractable shafts or cables, cams and pivots. Controls can be configured to activate a hydraulic or pneumatic supply.

Knob 114 is a control configured to be rotated to advance and/or retract inner shaft 101 within outer sheath 109. In FIG. 1, inner shaft 101 has been advanced such that expandable assembly 130 has exited sheath 109. Expandable assembly 130 may comprise an assembly that is resiliently biased in the radially expanded condition shown, such as an assembly comprising a Nitinol cage biased in the radially expanded condition shown that expands at it exits sheath 109. In these embodiments, retraction of shaft 101 can be performed to draw expandable assembly 130 within sheath 109, expandable assembly 130 being radially compressed during its insertion into sheath 109. Alternatively, expandable assembly 130 may be deployable to the radially expanded condition after exiting sheath 109, such as when expandable assembly 130 comprises a balloon that can be inflated or a deployable cage or array of arms that can be deployed by retraction of a shaft.

Figure 19:
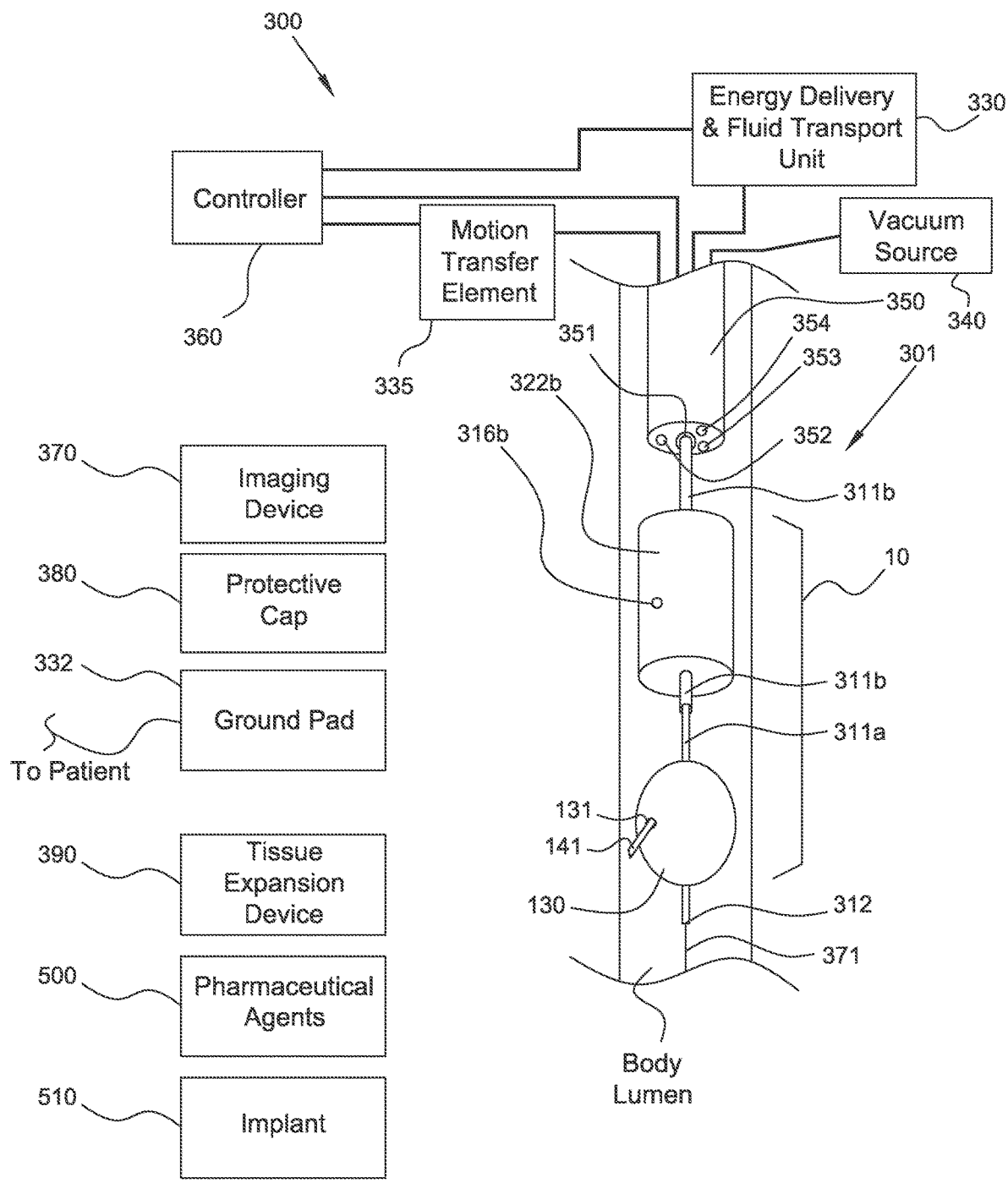
FIG. 19 is a system for expanding tissue as well as for ablating or otherwise treating target tissue, consistent with the present inventive concepts.

Handle 110 can include one or more controls 111, such as controls 111a and 111b through 111n as shown, such as to electrically and/or mechanically activate one or more components or assemblies of device 100, such as to activate flow of fluid and/or application of a vacuum, such as by activating one or more fluid valves as described in reference to FIG. 19 herebelow. Handle 110 can include an array of knobs 112 and receiving slots 113, such as knobs 112a and 112b through 112n and receiving slots 113a and 113b through 113n. Knobs 112a and 112b through 112n are operably connected to one or more linkages, not shown but configured to individually or collectively control the advancement and retraction of one or more fluid delivery elements 140, such as fluid delivery elements 140a and 140b through 140n that advance through openings 131a and 131b through 131n, respectively. Alternatively or additionally, one or more fluid delivery elements 140 may be constructed and arranged to penetrate tissue by entering into an opening 131, without exiting opening 131, such as when a vacuum is applied to the opening 131 and tissue is drawn into opening 131, as is described herebelow. A numerous range of vacuum pressure levels can be applied, such as a vacuum of 5 to 45 cmHg below atmospheric pressure, such as a vacuum between 5 and 20 cmHg below atmospheric pressure. Fluid delivery elements 140 can be of numerous forms configured to deliver fluid to tissue, including but not limited to: a needle; a water jet comprising a nozzle; an iontophoretic element; a porous element; and combinations of these. Knobs 112 can be configured to allow axial travel of fluid delivery elements 140 through a range of distances, such as distances between 1 mm and 10 mm, or distances between 3 mm and 7 mm. In some embodiments, fluid delivery extension is limited to a maximum of 10 mm or 7 mm. Fluid delivery elements 140 can be advanced axially and/or radially. In some embodiments, fluid delivery elements 140 are advanced axially and radially, such as to radially advance to be proximate and/or within (e.g. penetrating into) tissue. Alternatively, fluid delivery elements 140 may be advanced into a protective recess, such as the openings 131 described in reference to FIGS. 5, 5A, 5B, 5C, 10 and 11 herebelow, such as after tissue that has been drawn via a vacuum into the recess.

In some embodiments, one or more adjustable mechanical stops may be included, such as adjustable stop 118, configured to allow an operator to limit the advancement of knob 112 to the right of the page as shown. Handle 110 may include one or more markings corresponding to the travel of fluid delivery elements 140 through advancement of knobs 112, markings not shown. Magnitude of advancement of fluid delivery elements 140, both linear distance as well as radial displacement from a central axis, may be configured to expand a first tissue layer, while avoiding expansion of a second, deeper tissue layer. The fluid delivery elements 140 may be constructed and arranged, and positioned, such as to expand a first tissue layer, while avoiding expansion of a second, more shallow tissue layer. The fluid delivery elements 140 may be configured to penetrate (e.g. when in the form of a needle) and/or to cause fluid to penetrate (e.g. when in the form of a water jet) tissue of various properties and shapes. In some embodiments, a fluid delivery element 140 is configured to penetrate the plicae of the gastrointestinal tract.

Fluid delivery elements 140 may be of similar or dissimilar types, such as in an embodiment in which fluid delivery element 140*a* is a needle and fluid delivery element 140*b* is a water jet. Multiple fluid delivery elements 140 may be configured to deliver fluid simultaneously and/or sequentially. Multiple fluid delivery elements 140 may be connected to individual supplies of fluid, such as fluid delivery tubes 121*a* and 121*b* through 121*n*, or one or more fluid delivery elements 140 may be attached to a single supply of fluid, such as is described in reference to FIG. 13 herebelow.

Fluid delivery elements 140 may comprise a symmetric circumferential array of fluid delivery elements, such as an array of 2, 3, 4, 5, 6, 7, 8, 9 or 10 fluid delivery elements 140. In some embodiments, fluid delivery elements 140 can comprise a linear or axial array of fluid delivery elements, such as an array of 2, 3, 4, 5, 6, 7, 8, 9 or 10 fluid delivery elements 140. In some embodiments, multiple fluid delivery elements 140 can be in an asymmetric pattern, along a single circumference or at varied axial locations along device 100. Fluid delivery elements 140 may be positioned singly, on or within two or more support arms of expandable assembly 130, not shown but such as the support arms described in detail in reference to FIGS. 4 and 5 herebelow. Alternatively, multiple fluid delivery elements can be positioned on or within a single support arm. Arrays of multiple fluid delivery elements 140 may be arranged in a spiral pattern, and can comprise a pre-deployment and/or post-deployment spiral pattern of fluid delivery elements 140 that may be similar or different. Spiral patterns of fluid delivery elements 140 can be positioned to allow efficient compacting of an expandable assembly 130, such as to be insertable into a small lumen of a body access device such as an endoscope. Arrays of multiple fluid delivery elements 140 can be configured to deliver fluid simultaneously or sequentially. Fluid injections may comprise a single injection in a single location; multiple injections in a single location (e.g. multiple injections without repositioning assembly 130); or multiple injections in multiple locations. Repositioning of assembly 130 between injections can comprise axial advancement or retraction, as well as rotation.

In some embodiments, a vacuum is applied to openings 131, such as via a vacuum pump or other negative pressure source fluidly attached to openings 131, such as via vacuum source 340 connected to one or more internal components of handle 110 via connection 341 as shown. A vacuum can be applied to one or more lumens of handle 110 and/or shaft 101, not shown but lumens that are fluidly connected to one or more lumens of connection 341, and then travel distally to fluidly connect to one or more openings 131. Vacuum applied to openings 131, or another opening of expandable assembly 130 or another component of device 100, can be used to maintain contact with tissue and/or to manipulate tissue. In some embodiments, the applied vacuum is constructed and arranged to cause tissue to be drawn into openings 131, such as is described in reference to FIGS. 5 and 10 herebelow. Alternatively or additionally, vacuum source 340 can apply a vacuum to one or more fluid delivery elements 140, such as vacuum intermittently applied to one or more needles between fluid delivery periods. Vacuum source 340 can provide a fixed vacuum and/or it may provide a vacuum whose pressure or other performance parameter is adjustable by an operator. In some embodiments, one or more of controls 111 may comprise a control configured to connect vacuum source 340 to one or more of openings 131. In a particular embodiment, one or more of controls 111 comprises a hole or other opening that is fluidly connected to a lumen that fluidly connects vacuum source 340 and one or more openings 131. This opening of control 111 prevents any significant vacuum pressure from reaching the one or more connected openings 131. However, covering of the opening of control 111, such as by the finger of an operator, causes the vacuum pressure to increase at the one or more associated openings 131, such as to cause tissue to be withdrawn into these one or more openings 131.

In some embodiments, assembly 130, one or more fluid delivery elements 140, and/or another component of device 100 comprise a flexibility and radial support that allow flexing without luminal collapse, such that one or more fluid delivery elements 140 can automatically translate radially (e.g. toward the center of a lumen) as one or more tissue layers expand. Alternatively or additionally, assembly 130, one or more fluid delivery elements 140, and/or another component of device 100 may be configured to manually be translated and/or radially compacted to similarly translate radially as one or more tissue layers expand.

In some embodiments, fluid delivery is performed during advancement and/or retraction of one or more fluid delivery elements 140. Alternatively or additionally, fluid delivery is performed after one or more fluid delivery elements 140 are positioned at a target tissue location. Fluid delivery elements 140 can comprise a component selected from the group consisting of: a needle; a water jet; an iontophoretic element; and combinations of these, such as those described in reference to FIGS. 7, 8 and 9 and other figures described herebelow. Fluid delivery elements 140 are shown in a retracted state in FIG. 1. The multiple fluid delivery elements 140 and associated openings 131 may be distributed evenly along a relatively singular axial location of shaft 101. For example, two fluid delivery elements 140 may be separated by 180°, three fluid delivery elements 140 may be separated by 120°, four fluid delivery elements 140 may be separated by 90°, five fluid delivery elements 140 by be separated by 72°, and so on. In alternative embodiments, one or more fluid delivery elements 140 and associated openings 131 can be separated by different separation angles, and can be positioned at a single axial position (i.e. a single circumferential pathway), or along multiple axial locations.

Handle 110 may include or be attached to one or more sources of fluid, such as reservoirs 125 including reservoir 125*a* and 125*b* through 125*n* as shown. Reservoirs 125 may comprise a supply of fluid, such as a liquid filled chamber, or they may comprise a port, such as a luer, for attachment to a supply of fluid, such as a fluid filled syringe. Fluid delivery elements 140*a* and 140*b* through 140*n* are fluidly connected to fluid delivery tubes 121*a* and 121*b* through 121*n* respectively, such that fluid can be delivered from each reservoir 125, through each associated fluid delivery tube 121 to each respective fluid delivery element 140. While fluid delivery tubes 121*a* and 121*b* through 121*n* are shown exiting the side of handle 110, alternative exit points can be used including exiting the distal end of handle 110 such as to ease in rotation of handle 110.

Numerous forms of one or more fluids can be delivered through fluid delivery elements 140 to expand tissue. The fluid may comprise a liquid, a gas, or a combination of one or more liquids and gases. In some embodiments, the injected fluid is selected from the group consisting of: water; saline such as hypertonic saline; air; $CO_2$; one or more hydrogels; epinephrine; hypertonic dextrose water; hyaluronic acid; glycerol solutions; and combinations of these. In some embodiments, the injected fluid comprises a colorant or is otherwise configured to be visible during injection, such as via an endoscope camera or other visualization device such that the tissue expansion can be quantified or otherwise assessed. Typical fluids to be visualized include but are not limited to: methylene blue or other dye; radiopaque fluid; MR visualizable fluid; ultrasonically visualizable fluid; and combinations of these. The injected fluid may comprise a fluid selected from the group consisting of: a magnetic fluid; a hydrogel; a fluid configured to increase in viscosity after injection; a fluid configured to decrease in viscosity after injection; a fluid that is heated prior to injection such as a mixture of glycerol and saline that is heated prior to injection; a fluid with a similar osmolarity to the tissue in which it is being injected; a fluid configured to act as an thermal or electrical insulator; and combinations of these. Colored (e.g. non-clear) fluids or fluids that change color may be injected. In some embodiments, a liquid changes color due to a temperature change of the fluid, such as to assess the presence or quantity of tissue expansion. In some embodiments, a first color fluid is injected during a first injection, and a second color fluid is injected during a second injection, such as with the same or a different fluid delivery element. In some embodiments, an injected fluid provides a bioactive function, such as a bioactive function selected form the group consisting of: sclerosant; an anti-inflammatory agent; an antimicrotubule or other mitotic inhibitors; an alkylating agent; an antimetabolite; an anthracycline; a plant alkaloids; a topoisomerase inhibitor; an anti-proliferative; and combinations of these.

Handle 110 may include or be attached to a functional element, such as functional element 119 shown, which comprises a functional element or assembly selected from the group consisting of: a vacuum source; a hydraulic source; a pneumatic source; a source of electrical energy such as a battery or a radiofrequency energy generator; a rotating drive mechanism such as a drive mechanism configured to rotate an imaging element such as an ultrasound crystal or an optical fiber; and combinations of these. Functional element 119 may be fluidly, electrically or otherwise operably connected to one or more components of device 100, such as an operably connection to fluid delivery elements 140, expandable assembly 130, openings 131, and/or another component of device 100.

In some embodiments, device 100 comprises one or more sensors 135, such as one or more sensors selected from the group consisting of: a pressure sensor; a force sensor; a strain gauge; an electrode; an impedance sensor; a visualization sensor such as an ultrasound crystal, an optical visible light, OCT or OCDR fiber; a light sensor array such as a CCD; a physiologic sensor; a magnetic sensor; a light sensor; and combinations of these. In some embodiments, a pressure sensor is included, such as to monitor pressure of tissue expansion. Sensor 135 may be used to perform a diagnostic, such as in a diagnostic assembly in combination with one or more components integral to or external to handle 110, such as one or more electronic components configured to analyze a signal received from sensor 135 and produce a diagnostic output. Sensor 135 can be used to quantify or otherwise assess one or more of: amount of tissue expansion; current tissue thickness (e.g. pre, during and/or post expansion); tissue layer thickness; penetration distance of a fluid delivery element; color density of an injected fluid; impedance of tissue; temperature of tissue such as temperature of tissue that has received a heated or chilled fluid via a needle such as needle 141 of FIGS. 4-4B; and combinations of these. Alternatively or additionally, sensor 135 may comprise a transducer, such as a transducer selected from the group consisting of: a heat transducer; a cooling transducer; a source of light such as an LED; and combinations of these.

Device 100 may be configured to be advanced through a separate body introduction device, such as an endoscope in which device 100 is introduced through a lumen also known as a "working channel" of the endoscope. In these embodiments, device 100 may not include outer sheath 109, and shaft 101 may be fixedly attached to handle 110. Expandable assembly 130 can be expanded automatically or manually, as it exits or after it exits, respectively, the distal end of the endoscope. Device 100 is introduced such that fluid delivery elements 140 are in proximity to one or more tissue layers to be expanded, such as the tissue described in reference to FIGS. 3A, 3B and 3C herebelow. Shaft 101 may comprise a diameter configured for insertion through lumen of a limited size, such as a shaft with a maximum diameter or otherwise configured to be inserted through a lumen with a diameter less than or equal to 6 mm. In some embodiments, shaft 101 is inserted into a patient's anatomy along the side of an endoscope, such as when shaft 101 has a relatively continuous diameter of approximately 8 mm or less. In other embodiments, shaft 101 is inserted into the patient anatomy void of an endoscope, such as when shaft 101 has a relatively continuous diameter of approximately 13 mm or less.

Shaft 101 may comprise an insertable or "working" length configured to provide access to one or more body locations such as one or more gastrointestinal body locations. In some embodiments, device 100 is configured to expand tissue in the esophagus and shaft 101 is configured to be inserted through the mouth and have a working length of greater than or equal to approximately 25 cm. In some embodiments, device 100 is configured to expand tissue in the stomach and shaft 101 is configured to be inserted through the mouth and have a working length of greater than or equal to approximately 35 cm. In some embodiments, device 100 is configured to expand tissue in the duodenum and shaft 101 is configured to be inserted through the mouth and have a working length of greater than or equal to approximately 100 cm. In some embodiments, device 100 is configured to expand tissue in the jejunum and shaft 101 is configured to be inserted through the mouth and have a working length of greater than or equal to approximately 140 cm. In some embodiments, device 100 is configured to expand tissue in the ileum and shaft 101 is configured to be inserted through the mouth and have a working length of less than or equal to approximately 300 cm. Device 100 may be configured for delivery over a guidewire, such as via a lumen along the majority of length of shaft 101 (such as is described in reference to FIG. 4 herebelow), or via a sidecar lumen configured for rapid exchange guidewire delivery, such as is described in reference to FIG. 10 herebelow. Device 100 can include one or more markers, not shown, but typically comprising one or more markers selected from the group consisting of: radiopaque markers; electromagnetic markers; ultrasonically visible markers; and combinations of these.

Referring now to FIG. 1A, knobs 112 have each been advanced to the right of the page as shown, such as to individually cause fluid delivery elements 140a and 140b through 140n to exit openings 131a and 131b through 131n, respectively. In an alternative embodiment, one or more knobs 112 are configured to advance two or more fluid delivery elements 140. The amount of extension of each fluid delivery element 140 may be controlled manually and/or automatically by the amount of advancement of knob 112, such as to control depth of penetration of fluid delivery element 140 into tissue. Handle 110 can include one or more markings, not shown but delineated to indicate axial advancement and/or radial displacement of each fluid delivery element 140. One or more needle stops can be included to ensure precise advancement of each fluid delivery element 140, needle stops not shown but such as those described in reference to FIG. 10 herebelow.

In some embodiments, sheath 109, shaft 101, expandable assembly 130 and/or another component of device 100 is constructed and arranged to be displaced as tissue is expanded, such as a radial displacement toward the center of a lumen such as a lumen of the duodenum. Alternatively or additionally, expandable assembly 130 and/or another component of device 100 may be constructed and arranged to radially compress as tissue is expanded.

Referring now to FIG. 2, a flow chart of a method for tissue expansion is illustrated, consistent with the present inventive concepts. In STEP 200, a tissue expansion device of the present inventive concepts is inserted into a patient, such as a patient receiving a gastrointestinal diagnostic or therapeutic procedure. The tissue expansion device may be inserted through a lumen of a body access device, such as an endoscope. Alternatively or additionally, the tissue expansion device may be inserted over a guidewire, such as a guidewire passing through a lumen of the device, or a rapid exchange segment near the distal end of the tissue expansion device.

In STEP 210, one or more fluid delivery elements of the tissue expansion device are positioned in proximity to tissue to be expanded. This positioning may be performed using a visualization apparatus, such as a visualization apparatus selected from the group consisting of: an imaging device integral to or inserted through an endoscope; an imaging assembly integral to the tissue expansion device; an imaging device external to the patient such as a fluoroscope, a CT scanner, an MR scanner; an ultrasound imager; an imaging device inserted into the patient, such as a visual camera and/or an ultrasound probe or catheter; and combinations of these.

In STEP 220, an optional step is performed in which one or more fluid delivery elements of the tissue expansion device are advanced, such as an advancement in which the one or more fluid delivery elements make contact with tissue and/or penetrate an outer layer of tissue. In some embodiments, the one or more fluid delivery elements penetrate the mucosal layer of the gastrointestinal tract and enter the submucosal layer, such as in a segment of the duodenum. In some embodiments, an expandable assembly including one or more fluid delivery elements may be expanded, typically during or prior to the performance of STEP 220, such as to contact luminal wall tissue such as luminal wall tissue of the duodenum. The expandable assembly can be resiliently biased in a radially expanded state, such as a resiliently biased basket or cage supporting one or more fluid delivery elements and attached fluid delivery tubes. Alternatively or additionally, STEP 220 may include a tissue manipulation step in which tissue is moved, such as a movement toward a fluid delivery element and/or into an opening. In some embodiments, vacuum is applied to a port or other opening, such as to draw tissue into the opening, such as is described in reference to FIGS. 10, 10A and 10B herebelow. Once positioned in the opening, a fluid delivery element can be advanced and/or fluid delivered to the captured tissue. The applied vacuum and opening size can be constructed and arranged to preferentially move certain tissue into the opening, such as to preferentially move one or more inner layers of tissue into the opening while avoiding one or more deeper layers being moved into the opening. In some embodiments, mucosal and submucosal tissue layers are drawn into the opening while the muscularis layer remains outside the opening or is otherwise positioned to avoid being expanded by the fluid delivery element. After application of the vacuum, one or more other tissue manipulations may be performed (e.g. to "tent" the tissue), such as via advancement, retraction and/or rotation of the tissue expansion device and/or a component of the device.

In STEP 230, one or more fluids are delivered by the one or more fluid delivery elements, into tissue, to cause one or more layers of the tissue to expand. In some embodiments, one or more fluid delivery elements are moved (e.g. advanced or retracted), during the fluid delivery of STEP 230. Fluid is delivered through one or more fluid delivery tubes of the tissue expansion device, to the one or more fluid delivery elements. The one or more fluid delivery tubes can be attached to one or more sources of fluids, such as one or more syringes, pumping assemblies and/or reservoirs of fluids.

In STEP 240, an optional step of assessing tissue expansion is performed. The tissue expansion assessment can be performed using one or more visualization devices as has been described above, such as a device used in a visualization procedure performed at a time after fluid injection, such as 10, 20 or 30 seconds after fluid injection has initiated or ceased. In some instances, a visualization procedure may be performed at a time immediately prior to the performance of an ablation procedure, such as 15, 30, or 45 minutes after fluid injection has initiated or ceased. If insufficient expansion is achieved, an optional STEP 245 may be performed, in which one or more fluid delivery elements are retracted, and one or more portions of the tissue expansion device is repositioned. STEP 245 may include various repositioning maneuvers including but not limited to: rotating a shaft of the fluid delivery device and/or a support structure containing one or more fluid delivery elements; advancing one or more fluid delivery elements axially and/or radially; retracting one or more fluid delivery elements axially and/or radially; and combinations of these. STEP 245 may further include advancing fluid delivery elements, such as the advancement described in reference to STEP 220 hereabove, such as when one or more fluid delivery elements were previously retracted during STEP 245. STEP 230 is subsequently repeated, with or without the retraction and/or repositioning of STEP 245, in which one or more fluids are injected into tissue to cause expansion of one or more layers of tissue. The optional step of STEP 240 can be subsequently repeated, assessing the sufficiency of tissue expansion.

STEP 250 is performed after the injection of fluid into tissue in STEP 230, with or without the assessment performed in STEP 240 and/or the repositioning performed in STEP 245. In STEP 250, the fluid delivery device can be removed, remain in place for subsequent tissue expansion at a later time, or relatively immediately be advanced to a new tissue expansion location, such as by returning to STEP 210 and repeating STEPS 210 through 250 as illustrated.

The tissue expansion methods of the present inventive concepts may comprise a single step of injecting fluid, such as from one or more fluid delivery elements. Alternatively, the tissue expansion may be performed with multiple fluid injection steps, such as a first injection at a first location, followed by a second injection at a different location. The tissue expansion devices and their assemblies are typically configured to be rotated, such as to inject at multiple tissue locations along a relatively uniform circumference of luminal wall tissue. Fluid may be injected by multiple fluid delivery elements simultaneously and/or sequentially.

The fluid injected to cause tissue expansion may be of a pre-determined volume, such as a pre-determined volume per injection and/or cumulative volume of multiple injections delivered to a single site (e.g. a single injection of a needle or an amount of fluid delivered by a water jet's nozzle to a single location). In some embodiments, this pre-determined volume of fluid per injection and/or site comprises a volume of 0.5 ml to 4.0 ml, or 1.0 ml to 3.0 ml. These pre-determined volumes may be injected at different sites, such as between 2 to 10 sites along a relative circumference of luminal wall tissue. Complete tissue expansion can comprise one or more axial and/or circumferential injections, performed simultaneously and/or sequentially. Injections may be performed by one or more fluid delivery elements, such as two or more fluid delivery elements delivering fluid simultaneously and/or sequentially. Between injections, the tissue expansion device can be axially advanced and/or retracted, and it can be rotated. In some embodiments, fluid is delivered at a first location causing tissue expansion in a first expansion location. A second injection can be performed proximate the first expansion location, such as proximate an edge of the first expansion location. Repeated injections proximate previously expanded locations can be used to ease injection as well as reduce likelihood of perforation or failed tissue expansion.

Figure 3B:
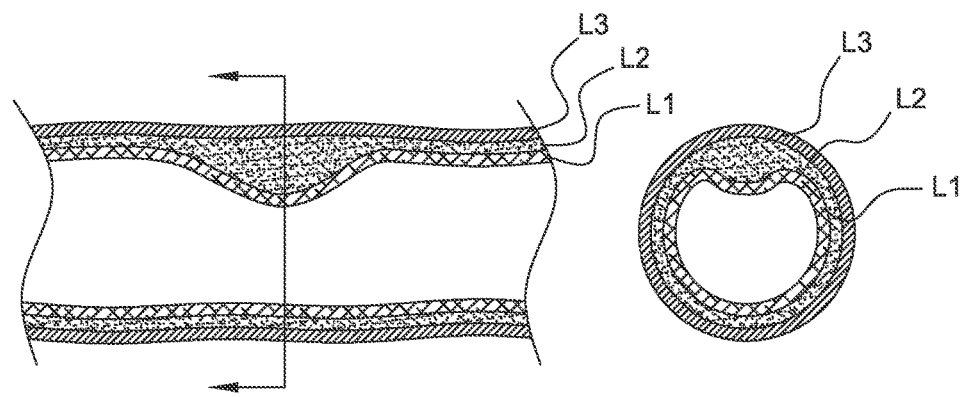
Figure 3C:
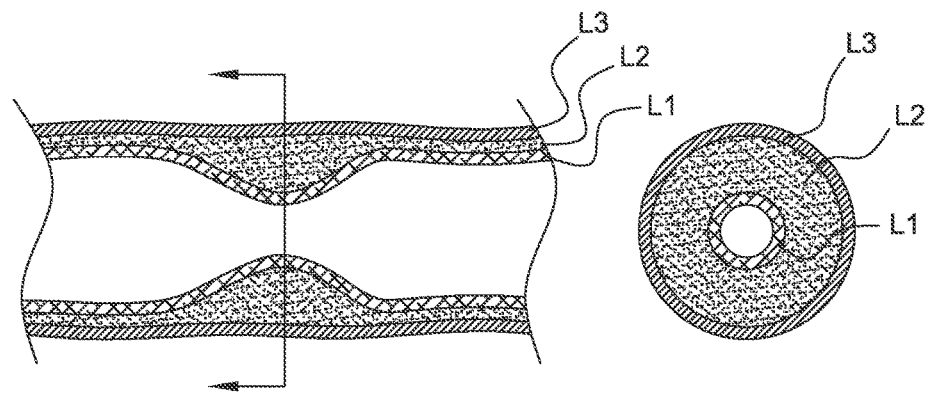

Referring now to FIGS. 3A, 3B and 3C, sectional side and end views of a segment of luminal wall tissue are illustrated, prior to, during and after full circumferential tissue expansion, respectively, consistent with the present inventive concepts. In FIG. 3A, a side and end sectional view of a segment of luminal wall tissue includes inner layer L1, mid layer L2 and outer layer L3, prior to any expansion by a tissue expansion device of the present inventive concepts. In FIG. 3B, a tissue expansion has occurred at a single location toward the top of the page as shown, within tissue layer L2. In FIG. 3C, a tissue expansion has occurred for a full 360° segment of layer L2. In some embodiments, a full or near full circumferential expansion (e.g. greater than approximately 300° of tissue expansion, greater than approximately 320° of tissue expansion, or greater than approximately 330° of tissue expansion), is performed in a relatively single step, such as from multiple fluid delivery elements. In other embodiments, a full or near full circumferential expansion is performed in multiple steps, such as from one or more fluid delivery elements that are configured to inject fluid in a first step and be rotated in one or more subsequent steps, each rotation followed by an injection of fluid into tissue.

The expansion of a tissue layer, such as layer L2 of FIGS. 3A through 3C, may be performed to cause a reduction in cross sectional area of the lumen, such as a reduction to 85% of the pre-expansion cross sectional area (e.g. a 35 mm lumen reduced to a 30 mm lumen), or a reduction to 75% of the pre-expansion cross-sectional area. Some body lumens comprise an inner layer including a non-smooth surface, such as the lining of the duodenum or jejunum including one or more folds known as the plicae. In some embodiments, the tissue expansion causes folds such as plicae to be smoothed and/or widened. This modification can be useful in subsequent treatments of the lumen's inner lining, such as to improve the results of one or more ablation procedures.

Numerous forms and locations of patient tissue can be expanded by the devices, systems and methods of the present inventive concepts. In some embodiments, the tissue to be expanded comprises submucosal tissue, such as submucosal tissue of the duodenum. The devices systems and methods of the present inventive concepts may be constructed and arranged to avoid expanding one or more layers of tissue, such as when the muscularis or serosal layer of the duodenum is prevented from being expanded. Applicable tissue may comprise luminal wall tissue or other tissue layers. Applicable tissue locations to be expanded can include luminal wall tissue selected from the group consisting of: a gastrointestinal tissue layer; a duodenal tissue layer; an esophageal tissue layer; a jejunal tissue layer; an ileal tissue layer; a colonic tissue layer; and combinations of these. Alternatively or additionally, tissue to be expanded may comprise tissue selected from the group consisting of: a stomach tissue layer; a bladder tissue layer; an oral cavity tissue layer; a uterine tissue layer; and combinations of these.

Figure 4:
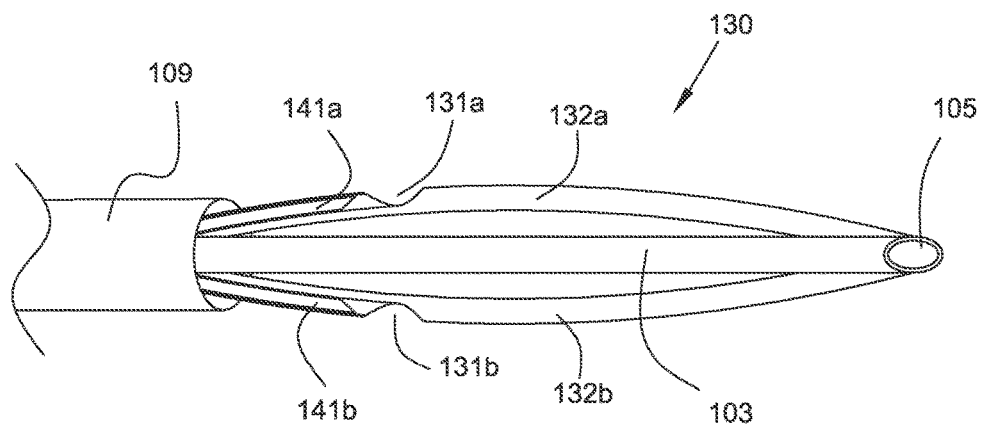
FIG. 4 is a side view of a distal portion of a tissue expansion device, including a manually deployable expandable assembly, consistent with the present inventive concepts.

Referring now to FIG. 4, a side view of a distal portion of a tissue expansion device is illustrated, including a manually deployable expandable assembly, consistent with the present inventive concepts. A tissue expansion device, such as a tissue expansion device similar to device 100 of FIG. 1, includes an expandable assembly 130 in a pre-deployment (e.g. prior to radial expansion) state. Expandable assembly 130 is shown to have been axially advanced to exit sheath 109, such as via one or more controls on a handle mounted on the proximal end of sheath 109. In some embodiments, sheath 109 comprises an endoscope, such as when expandable assembly 130 is advanced through a working channel of the endoscope. Expandable assembly 130 comprises at least two support arms, arms 132a and 132b typically a hollow or partially hollow tube such as a metal tube or a plastic tube. Arms 132a and 132b include openings 131a and 131b, respectively. The distal ends of arms 132a and 132b are attached to a control cable, cable 103, typically a metal or non-metallic cable which travels proximally and attaches to one or more controls on a proximal handle, such as those described in reference to handle 110 of FIG. 1 and configured to advance or retract cable 103. Cable 103 can comprise a hollow tube, such as a cable including a guidewire lumen 105, configured to allow over-the-wire delivery of expandable assembly 130 and sheath 109.

Two fluid delivery elements, needles 141a and 141b are shown positioned within arms 132a and 132b, respectively. Needles 141a and 141b typically comprise metal needles, such as needles with a gauge between 20 and 35 gauge, or between 23 and 27 gauge. Needles 141a and/or 141b may comprise a beveled end, such as an end with a bevel angle between 10° and 60°, such as a bevel angle of approximately 30°. Needles 141a and 141b are fluidly attached to one or more fluid delivery tubes, such as fluid delivery tubes 121 described in reference to FIG. 1, such that one or more fluids can be delivered to needles 141a and 141b via the fluid delivery tubes. Needles 141a and/or 141b may comprise a particular sharpness or other penetration characteristic such as to preferably penetrate one form of tissue, such as the submucosa, while avoiding or minimizing penetration of a deeper layer of tissue, such as the muscularis or serosal layers. Needles 141a and/or 141b may be constructed and arranged to be advanced to an exposed length of less than 10 mm, such as less than 7 mm. Needles 141a and 141b may be constructed and arranged to remain within openings 131a and 131b, respectively, as is described in reference to FIGS. 5 and 10 herebelow. Vacuum can be applied to openings 131a and 131b such as to draw tissue toward and/or into openings 131a and 131b. Alternatively or additionally, needles 141a and 141b may be constructed and arranged to advance out of openings 131a and 131b, respectively, as is described in reference to FIG. 4B herebelow.

Figure 4A:
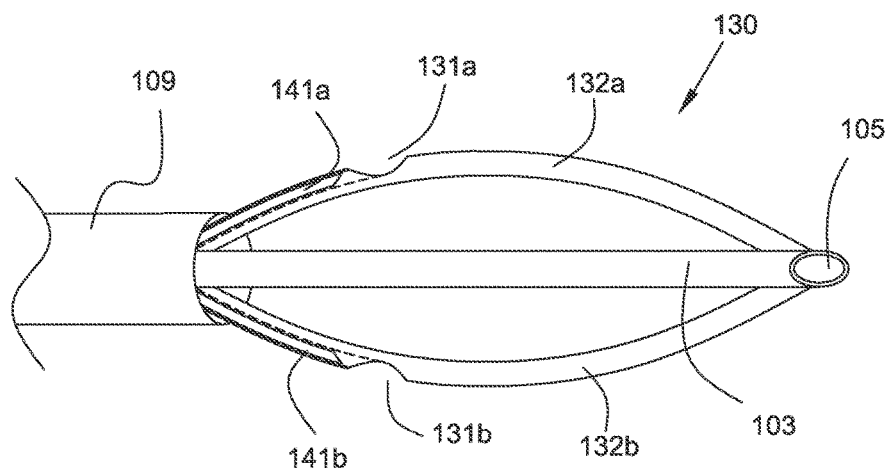
FIG. 4A is a side view of the tissue expansion device of FIG. 4, after radial expansion of the deployable assembly, consistent with the present inventive concepts.

Referring now to FIG. 4A, cable 103 has been retracted such that the mid portions of arms 132a and 132b extend radially from the axis of sheath 109. Openings 131a and 131b correspondingly extend radially as shown. Needles 141a and 141b remain in the pre-deployed position shown.

Figure 4B:
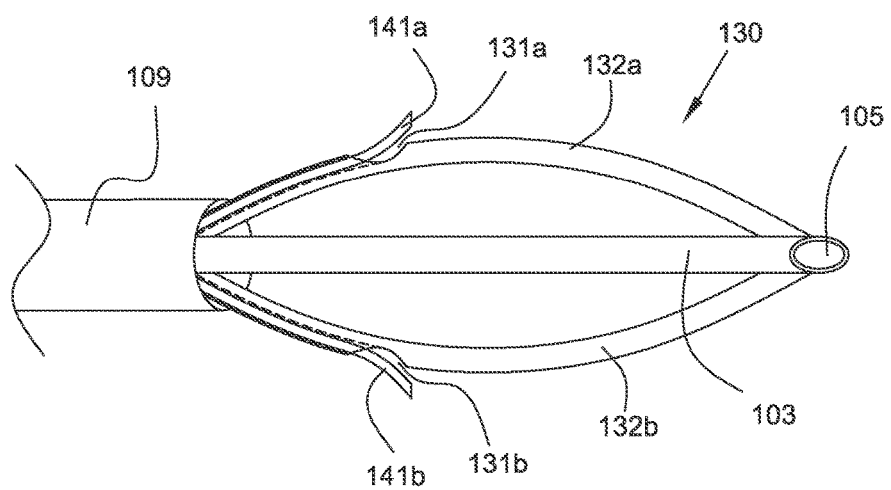
FIG. 4B is a side view of the tissue expansion device of FIGS. 4 and 4A, after radial expansion of the deployable assembly and advancement of fluid delivery elements, consistent with the present inventive concepts.

Referring now to FIG. 4B, needles 141a and 141b have been advanced to exit openings 131a and 131b, such that when expandable assembly 130 is positioned against tissue, such as luminal wall tissue, needles 141a and 141b penetrate into one or more tissue layers. Advancement of needles 141a and 141b may be done in combination or independently, such as via one or more controls on a proximal handle, not shown but such as is described in reference to handle 110 of FIG. 1. In alternative embodiments, needles 141a and 141b do not exit openings 131a and 131b, respectively, during advancement, such as is described in reference to the tissue expansion devices of FIGS. 5 and 10 herebelow. In these embodiments, a vacuum is applied to draw tissue into openings 131a and 131b and needles 141a and 141b penetrate the captured tissue when advanced.

Figure 5:
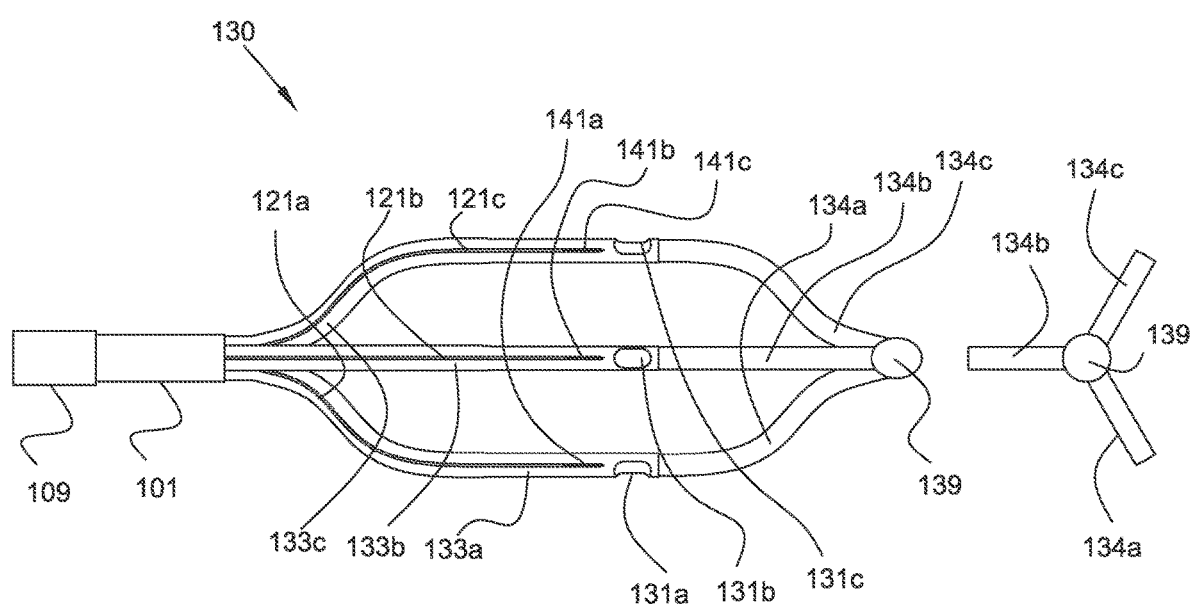
FIG. 5 is a side and end view of a distal portion of a tissue expansion device, including a self-expanding assembly, consistent with the present inventive concepts.

Referring now to FIG. 5, a side and end view of a distal portion of a tissue expansion device are illustrated, including a self-expanding assembly, consistent with the present inventive concepts. A tissue expansion device, such as a tissue expansion device similar to device 100 of FIG. 1, includes an expandable assembly 130 in a deployed (e.g. a radially expanded) state. Expandable assembly 130 is attached to the distal end of shaft 101, which has been axially advanced to exit sheath 109, such as via one or more controls on a handle mounted on the proximal end of sheath 109. In some embodiments, sheath 109 comprises an endoscope, such as when expandable assembly 130 is advanced through a working channel of the endoscope. Expandable assembly 130 comprises at least three support arms, such as three support arms comprising proximal segments 133a, 133b and 133c, and attached distal segments 134a, 134b and 134c respectively. Proximal segments 133a, 133b and 133c are typically a hollow or partially hollow tube such as a metal tube or a plastic tube, and configured to slidingly receive a fluid delivery element and include openings 131a, 131b and 131c, respectively. Distal segments 134a, 134b and 134c are typically resiliently biased in the orientation shown in FIG. 5, such as to cause expandable assembly 130 to be in a radially expanded condition when not surrounded by a compressing tube, such as sheath 109. Expandable assembly may be constructed of a resiliently biased metal, such as stainless steel and/or Nitinol that is resiliently biased in an expanded or contracted geometry. In some embodiments, assembly 130 is configured to transition to a radially compacted state, such as when inserted within a lumen of a tube such as sheath 109 and/or a working channel of an endoscope. Distal segments 134a, 134b and 134c can comprise an elastic, biocompatible material such as Nitinol or stainless steel formed in a curved orientation. Distal segments 134a, 134b and 134c may comprise a flat sheet material or a round tube. The distal end of distal segments 134a, 134b and 134c are attached to tip 139 which surrounds and maintains the position of the distal end of segments 134a, 134b and 134c. In alternative embodiments, distal segments 134a, 134b and 134c may be fabricated of a single sheet or otherwise fabricated such that their distal ends are connected, with or without a tip 139. Tip 139 may be covered by an atraumatic material, such as silicone or other biocompatible polymer.

Each proximal segment 133a, 133b and 133c contains a single fluid delivery element, needle 141a, 141b and 141c, respectively. Needles 141a, 141b and 141c are each attached to a single fluid delivery tube, 121a, 121b and 121c, respectively. In some embodiments, each fluid delivery tube travels proximally to a handle, such as to be attached to individual supplies of fluid for injection into tissue, such as reservoirs 125a, 125b and 125c, respectively described in reference to FIG. 1. In other embodiments, one or more of fluid delivery tubes 121a, 121b and/or 121c fluidly attach to each other, such as to attach to a source of fluid, such that fluid is simultaneously injected through one or more of fluid delivery tubes 121a, 121b and/or 121c. In some embodiments, a vacuum is applied, such as via a proximal handle port, such as a vacuum applied at one or more of openings 131a, 131b and 131c, around needles 141a, 141b and 141c, respectively, such as through a vacuum delivery tube, such as is described in reference to FIGS. 5A and 5C herebelow. Applied vacuum may be configured to maintain tissue position during penetration of tissue by needles 141a, 141b and/or 141c, and/or to manipulate tissue into openings 131a, 131b and 131c for subsequent needle advancement. In some embodiments, a second opening is provided on one or more of support arms 133a, 133b and/or 133c, openings not shown but configured to be fluidly attached to a source of vacuum and to apply one or more forces to tissue.

Figure 5A:
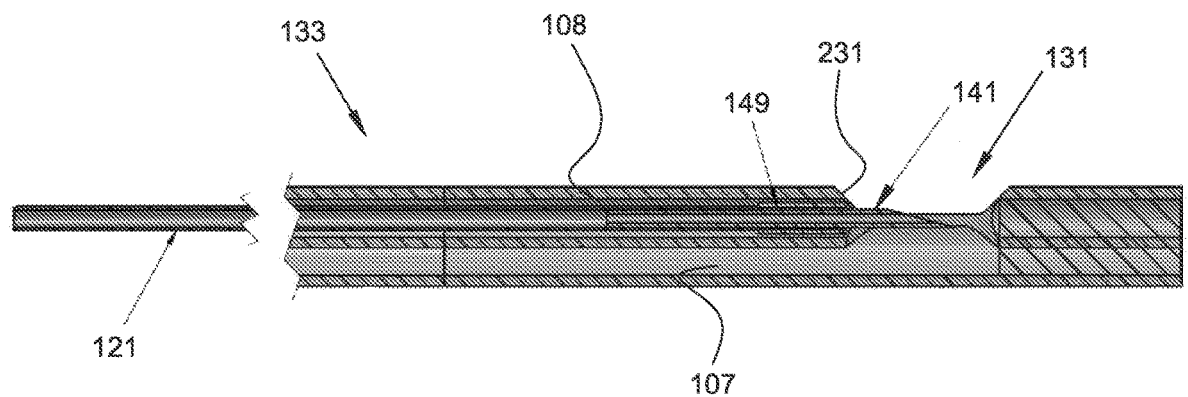
FIG. 5A is a side sectional view of a segment of a support arm of a tissue expansion device, including a support member for a fluid delivery element, consistent with the present inventive concepts.

Referring now to FIG. 5A, a side sectional view of a segment of a support arm of a tissue expansion device is illustrated, consistent with the present inventive concepts. A fluid delivery element is shown in an advanced position and a support member surrounds the fluid delivery element. A segment of a support arm 133 is shown, such as a segment of proximal support arm 133a, 133b and/or 133c of FIG. 5. Support arm 133 comprises two lumens, lumen 107 and lumen 108, and may be constructed of a rigid or flexible material, such as a metal material such as stainless steel or Nitinol, or a plastic material such as a Pebax® with a durometer between 50D and 80D. Lumen 108 slidingly receives needle 141. The distal end of fluid delivery tube 121 is fluidly and mechanically attached to the proximal end of needle 141, such as via a sealed bond and/or frictionally engaging interface (e.g. the interface between a proximal outer diameter portion of needle 141 and a distal inner diameter portion of tube 121). This attachment provides a fluid seal yet allows fluid to pass through fluid delivery tube 121 into needle 141. Needle 141 is constructed and arranged to be advanced into a recess in support arm 133, opening 131, such as to the advanced position shown. Needle 141 can comprise a needle between 25 and 30 gauge, such as a 27 gauge stainless steel needle with a beveled tip. Fluid delivery tube 121 can comprise a flexible shaft, such as a shaft comprising a plastic material including a braid, such as a polyimide shaft including a stainless steel braid.

On its proximal end, lumen 107 is fluidly attached to an operator activatable supply of vacuum, not shown but such as vacuum source 340 of FIG. 1. Lumen 107 is fluidly attached on its distal end to opening 131. Opening 131 can comprise sloped side walls 231, such as to cause tissue drawn into opening 131 to have a preferred shape and/or a preferred array of tensional force vectors imparted on the tissue. In use, needle 141 is in a retracted state (e.g. not entering opening 131), and a vacuum can be applied to opening 131. After tissue is drawing into opening 131, needle 141 is advanced (to the right of the page) to the position shown in FIG. 5A, penetrating tissue and ready for fluid to be delivered through fluid delivery tube 121 to expand one or more tissue layers drawing the tissue into opening 131.

A support and/or guiding element, ferrule 149 may be included to provide support to needle 141 as it penetrates tissue. Ferrule 149 can be configured to prevent undesired rotation, bending and or twisting to needle 141, such as when needle 141 is advanced into tissue. Ferrule 149 can comprise a round tube that is bonded to or frictionally engages a distal portion of needle 141. Ferrule 149 can comprise an outer diameter that approximates the inner diameter of lumen 108, such as when ferrule 149 comprises an outer diameter between 0.020" and 0.036" (e.g. a diameter approximating 0.028"), and lumen 108 comprises a diameter between 0.027" and 0.043" (e.g. a diameter approximating 0.035"). Ferrule 149 can comprise a tubular construct with a length between 1.5 mm and 2.5 mm, such as a length approximating 2.0 mm. Ferrule 149 can comprise a rigid material such as a metal such as stainless steel. Ferrule 149 can be axially positioned on needle 141 such that a majority of ferrule 149 remains within lumen 108 as the distal end of needle 141 travels axially to the position shown in FIG. 5A.

Figure 5B:
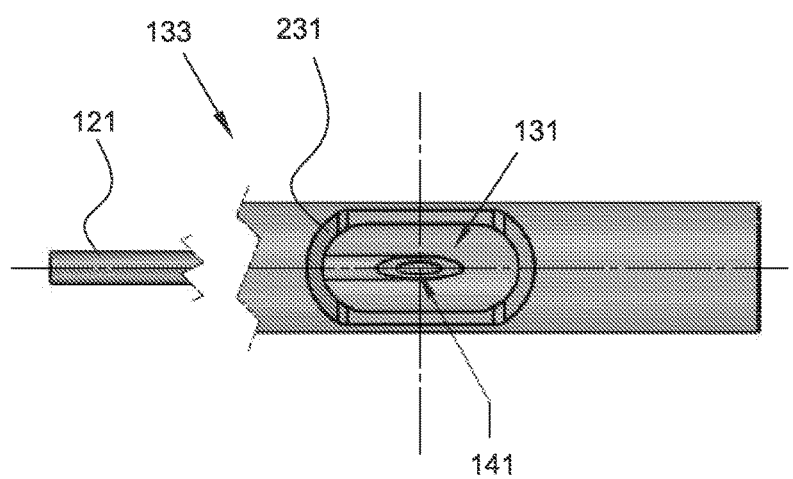
FIG. 5B is a top view of an opening of a support arm of a tissue expansion device, consistent with the present inventive concepts.

Referring now to FIG. 5B, a top view of an opening of a support arm of a tissue expansion device is illustrated, with a fluid delivery element in an advanced position, consistent with the present inventive concepts. A segment of a support arm 133 is shown, such as a segment of proximal support arm 133a, 133b and/or 133c of FIG. 5, and/or a segment of support arm 133 of FIG. 5A. Support arm 133 slidingly receives fluid delivery tube 121 and needle 141. Needle 141 is constructed and arranged to be advanced into a recess in support arm 133, opening 131, such as to the advanced position shown. Opening 131 can comprise sloped walls 231 such as to cause tissue drawn into opening 131 to have a preferred shape and/or a preferred array of tensional force vectors imparted on the tissue. Needle 141 and support shaft 133 can be constructed and arranged to maintain the relatively aligned position shown in FIG. 5B (e.g. aligned to a central axis of support arm 133 and/or opening 131), such as when needle 141 is advanced through tissue drawn into opening 131. Alignment can be achieved through a needle support and/or aligning component, such as ferrule 149 of FIG. 5A. In some embodiments, one or more components of the tissue expansion device, such as one or more of needle 141 and support arm 133, are constructed and arranged such that when needle 141 is fully advanced, the opening in the distal end of needle 141 is centered in opening 131, as is shown in FIG. 5B. Control of this positioning can be accomplished through the use of a needle stop, such as is described in reference to FIG. 10 herebelow and/or via one or more controls integral to a handle, such as handle 110 and associated controls described in reference to FIG. 1 hereabove.

In some embodiments, opening 131 comprises an axial length of approximately 4 mm, and needle 141 is constructed and arranged such that 3 mm of length resides in opening 131 when needle 141 is fully advanced, and the opening in the end of needle 141 is centered in opening 131 as shown. In some embodiments, opening 131 comprises an axial length up to 5 mm. In some embodiments, opening 131 comprises a width up to 2 mm.

Figure 5C:
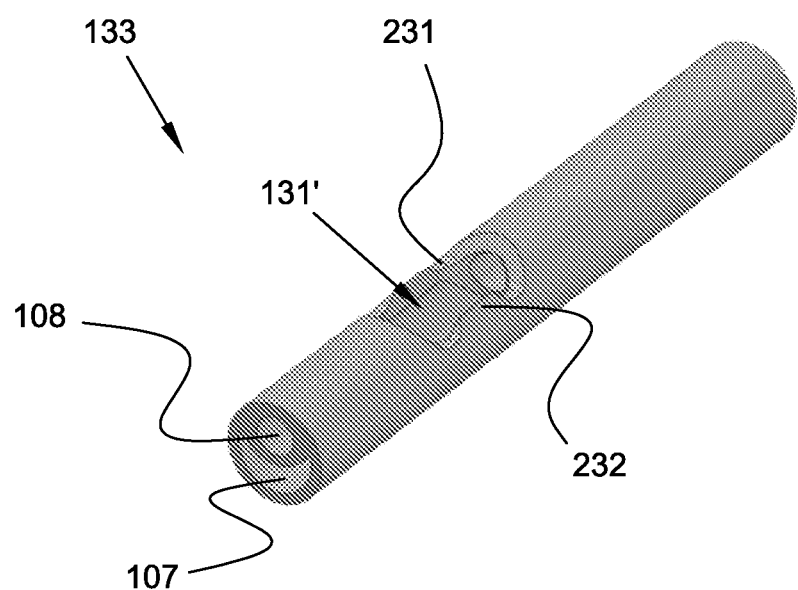
FIG. 5C is a perspective view of an alternative opening of a support arm, consistent with the present inventive concepts.

Referring now to FIG. 5C, a perspective view of an alternative opening of a support arm is illustrated, consistent with the present inventive concepts. A segment of a support arm 133 is shown, such as a segment of proximal support arm 133a, 133b and/or 133c of FIG. 5. Support arm 133 includes lumen 108 which is configured to slidingly receive a fluid delivery tube and a fluid delivery element such as a needle, fluid delivery tube and fluid delivery element removed for illustrative clarity. Support arm 133 can comprise a diameter between 0.070" and 0.100", such as a diameter approximating 0.090". Support arm 133 may be constructed of a rigid or flexible material, such as a metal material such as stainless steel or Nitinol, or a plastic material such as a Pebax® material. Lumen 108 can comprise a circular cross section, as is shown in FIG. 5C, such as a circular cross section with a diameter between 0.020" and 0.040", or approximately 0.035". Support arm 133 further includes lumen 107, which is configured to be fluidly attached to a supply of vacuum pressure such as vacuum pressure supplied by an operator adjustable vacuum source, such as vacuum source 340 of FIG. 1. Lumen 107 fluidly applies the vacuum to a recess or opening in support arm 133, such as opening 131', such as to cause tissue to be drawn into opening 131'. Lumen 107 may comprise a crescent shaped cross section, as is shown in FIG. 5C. Opening 131' is further constructed and arranged to receive a fluid delivery element such as a needle.

Opening 131' comprises projections 232 along the side walls of opening 131' such as projections configured to limit the amount of tissue drawn into opening 131' when a vacuum is applied to opening 131' via lumen 107. In some embodiments, projections 232 are constructed and arranged to allow sufficient tissue to be drawn into opening 131' such that one or more fluids delivered by a fluid delivery element such as a needle into tissue, causes tissue expansion to occur in a submucosal layer of gastrointestinal tissue, while avoiding expansion of deeper layers such as the muscularis or serosal layers. Additionally, opening 131' comprises sloped walls 231 such as to cause tissue drawn into opening 131' to have a preferred shape and/or a preferred array of tensional force vectors imparted on the tissue.

Figure 6:
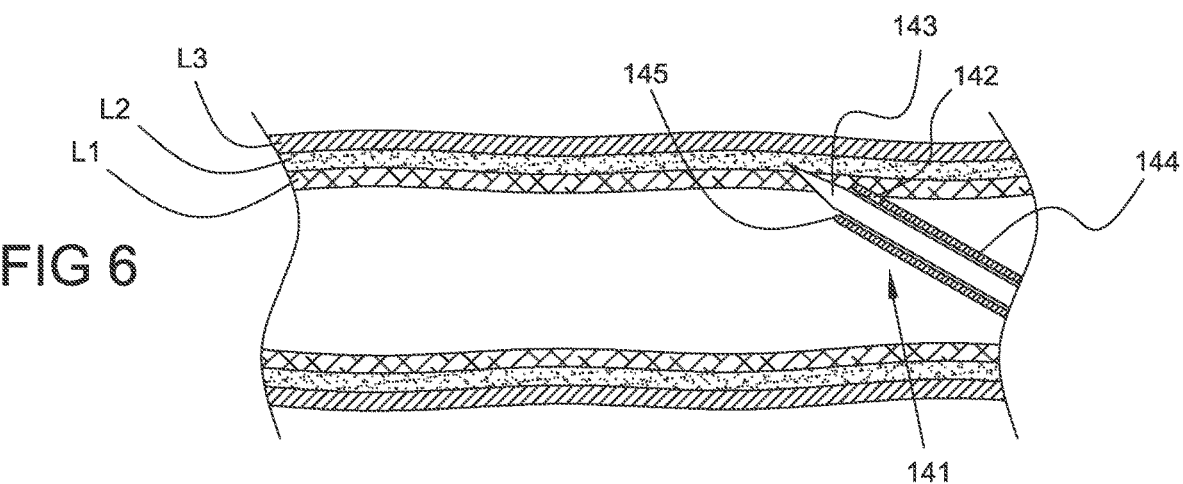
FIG. 6 is a side sectional view of a distal portion of a fluid delivery element comprising a penetrator and an atraumatic surrounding tube and positioned in a body lumen, consistent with the present inventive concepts.

Referring now to FIG. 6, a side sectional view of a fluid delivery element comprising a penetrator and an atraumatic surrounding tube is illustrated, consistent with the present inventive concepts. Fluid delivery element 141 has been positioned in a lumen of tissue, such as a lumen of the duodenum or other gastrointestinal lumen. The tissue comprises multiple layers, such as innermost layer L1, deeper layer L2 and yet deeper layer L3. In some embodiments, L1 comprises a mucosal layer, L2 comprises a submucosal layer, and L3 comprises a muscular layer with or without an overlying serosal layer. Fluid delivery element 141 comprises a hollow tube 144 that includes a rounded or otherwise atraumatic distal end 145, which slidingly receives a sharpened tube, penetrator 143, typically a hollow or solid tube, such as a metallic hypotube with a sharpened distal end. Tube 144 includes a hole in its wall, opening 142, positioned relatively proximate end 145. Tube 144 and penetrator 143 are sized such that fluid can be delivered in the space between tube 144 and penetrator 143, such as via one or more fluid delivery tubes, not shown but traveling proximally and fluidly connected to a supply of injectable fluid, such as is described in reference to FIG. 1 hereabove. Fluid can be delivered to tissue out of the distal end of tube 144 and/or via opening 142, such as when the distal end of tube 144 is occluded, such as by a less expansive layer of deeper tissue.

Fluid delivery element 141 is configured to allow initial penetration into tissue by penetrator 143, after which tube 144 can be advanced into tissue, as is illustrated and described in reference to FIGS. 6A and 6B hereinbelow. In FIG. 6, penetrator 143 has been advanced through tissue layer L1 and into tissue layer L2. Injection of fluid during advancement of tube 144 while penetrator 143 is also advanced (as in FIG. 6) can be performed, with fluid preferentially exiting through port 142, causing tissue expansion of layer L2 during advancement.

Figure 6A:
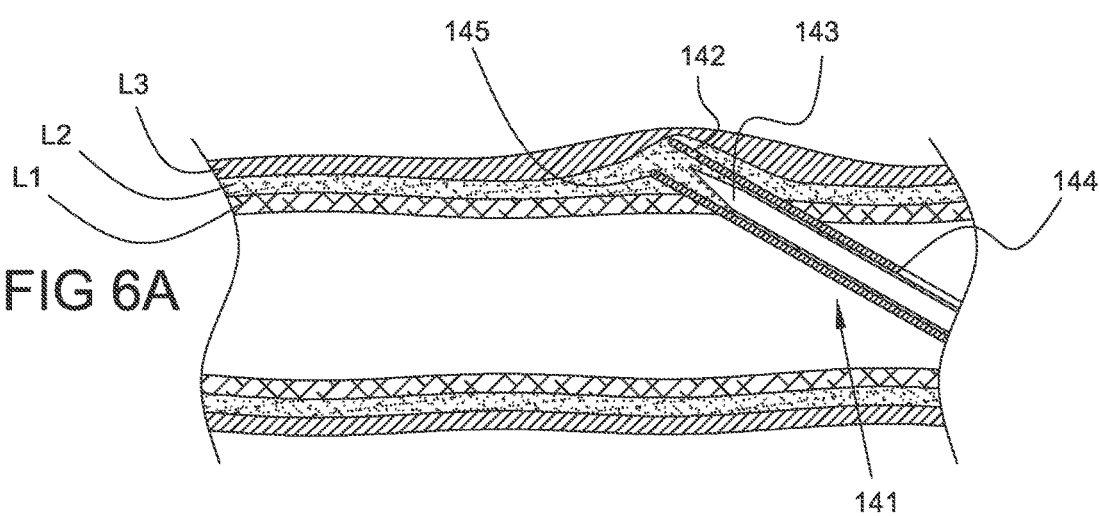
FIG. 6A is a side sectional view of the fluid delivery element of FIG. 6 after the tube has been advanced over the penetrator and into tissue, consistent with the present inventive concepts.

Referring now to FIG. 6A, tube 144 has been advanced, over penetrator 143, through tissue layer L1 and into tissue layer L2. Penetrator 143 is positioned, via advancement of tube 144 and/or retraction of penetrator 143, such that the distal end of penetrator 143 is contained within tube 144, such as to prevent further advancement of fluid delivery element 141 into deeper layers of tissue such as into tissue layer L3.

Figure 6B:
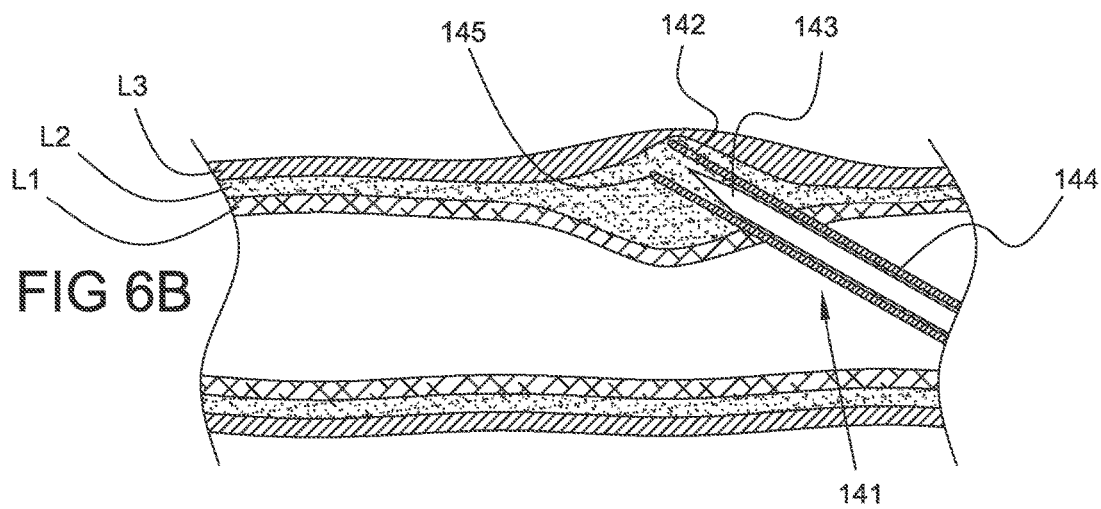
FIG. 6B is a side sectional of the fluid delivery element of FIGS. 6 and 6A after fluid has been injected into a layer of tissue, consistent with the present inventive concepts.

Referring now to FIG. 6B, fluid has been injected in the space between penetrator 143 and tube 144, such as to exit the distal end 145 of tube 144 and/or through opening 142, causing tissue layer L2 to expand.

Figure 7:
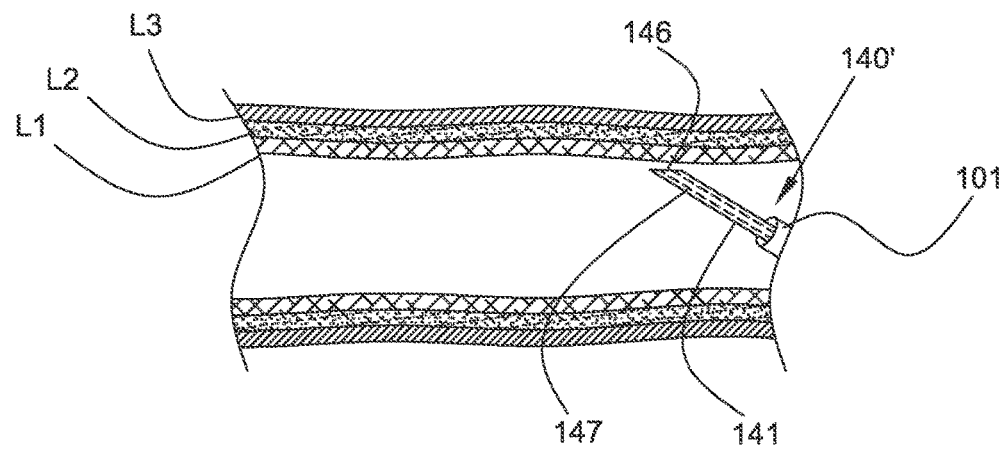
FIG. 7 is a side sectional view of a fluid delivery element comprising a needle with an internal lumen and positioned in a body lumen, consistent with the present inventive concepts.

Referring now to FIG. 7, a side sectional view of a fluid delivery element comprising a needle with an internal lumen is illustrated, consistent with the present inventive concepts. Fluid delivery element 140' has been positioned in a lumen of tissue, such as a lumen of the duodenum or other gastrointestinal lumen. The tissue comprises multiple layers, such as innermost layer L1, deeper layer L2, and yet deeper layer L3. Fluid delivery element 140' comprises a needle 141, including a lumen 147. Needle 141 comprises a sharpened distal tip 146, typically comprising a beveled end, and may be configured to be operably advanceable from shaft 101, such as via one or more controls on a proximal handle, as is described in reference to FIG. 1 hereabove. Needle 141 can be constructed and arranged to be rotated (e.g. when retracted), such as to perform multiple fluid delivery events around a circumference of tissue, such as to create a full or near full circumferential tissue expansion. Lumen 147 is fluidly connected to one or more fluid delivery tubes, not shown but traveling proximally and fluidly connected to a supply of injectable fluid. Fluid can be delivered to tissue out of distal end 146 of needle 141, such as via one or more controls on a proximal handle or on a device connected to a proximal handle, such as is described in reference to FIG. 1 hereabove.

Figure 8:
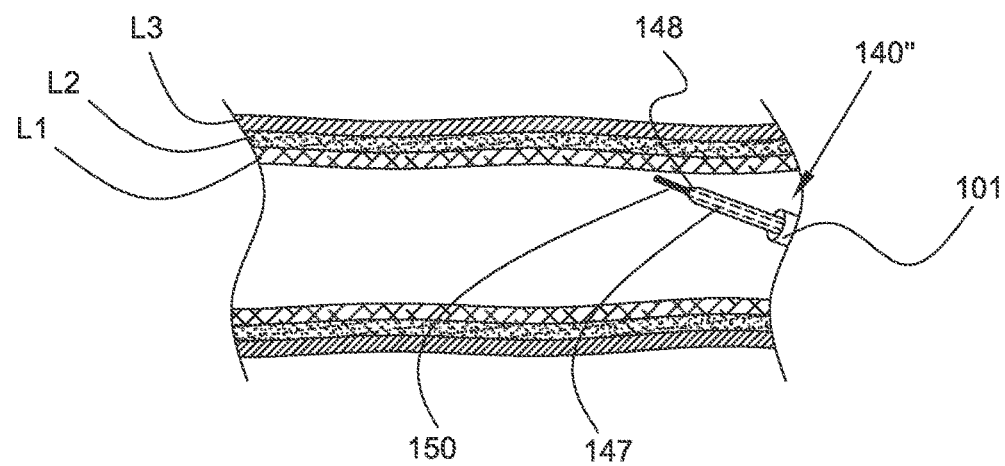
FIG. 8 is a side sectional view of a fluid delivery element comprising a water jet including a nozzle and an internal lumen and positioned in a body lumen, consistent with the present inventive concepts.

Referring now to FIG. 8, a side sectional view of a fluid delivery element comprising a water jet including a nozzle and an internal lumen is illustrated, consistent with the present inventive concepts. Fluid delivery element 140" has been positioned in a lumen of tissue, such as a lumen of the duodenum or other gastrointestinal lumen. The tissue comprises multiple layers, such as innermost layer L1, deeper layer L2 and yet deeper layer L3. Fluid delivery element 140" comprises a nozzle 148, fluidly connected to lumen 147. Nozzle 148 can be configured to allow a high-pressure delivery of fluid, injectate 150, shown in a collimated stream comprising sufficient pressure to penetrate one or more tissue surfaces, such as to deliver tissue to a deeper layer of tissue, such as a water nozzle as is used in the Erbejet 2 manufactured by Erbe Elektromedizin GmbH of Tubingen, Germany. Nozzle 148 can be configured to be operably advanceable from shaft 101, such as via one or more controls on a proximal handle, as is described in reference to FIG. 1 hereabove. Nozzle 148 can be constructed and arranged to be rotated, such as to perform multiple fluid delivery events around a circumference of tissue, such as to create a full or near full circumferential tissue expansion. While nozzle 148 is shown in an orientation along the axis of shaft 101, nozzle 148 can be oriented off-axis, such as at an angle between 1° and 179°, typically between 10° and 170°. While nozzle 148 is shown as a single nozzle, multiple nozzles can be employed. Lumen 147 is fluidly connected to one or more fluid delivery tubes, not shown but traveling proximally and fluidly connected to a supply of injectable fluid. Fluid can be delivered to tissue from nozzle 148, such as via one or more controls on a proximal handle or on a device connected to a proximal handle, such as is described in reference to FIG. 1 hereabove.

Figure 9:
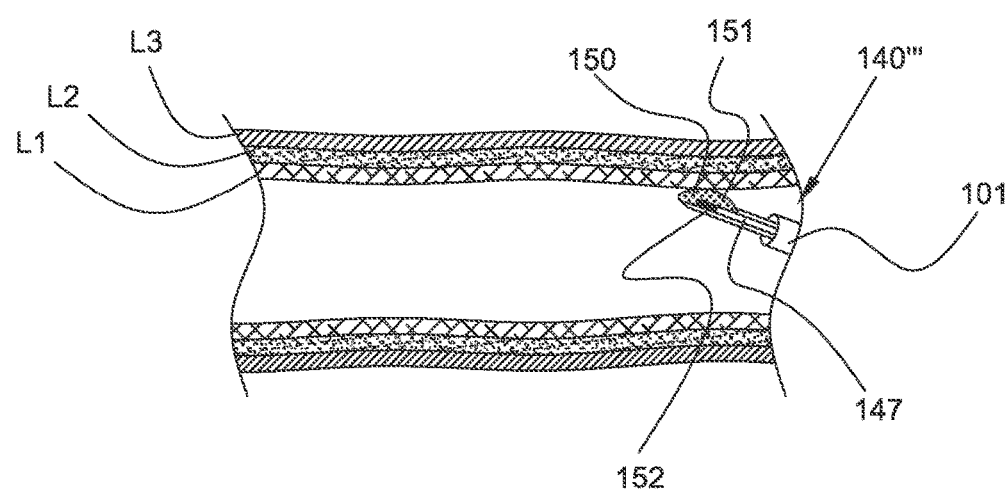
FIG. 9 is a side sectional view of a fluid delivery element comprising an iontophoretic fluid delivery assembly and positioned in a body lumen, consistent with the present inventive concepts.

Referring now to FIG. 9, a side sectional view of a fluid delivery element comprising an iontophoretic fluid delivery assembly is illustrated, consistent with the present inventive concepts. Fluid delivery element 140''' has been positioned in a lumen of tissue, such as a lumen of the duodenum or other gastrointestinal lumen. The tissue comprises multiple layers, such as innermost layer L1, deeper layer L2 and yet deeper layer L3. Fluid delivery element 140''' comprises an iontophoretic delivery element comprising reservoir 151 and electrode 152. Reservoir 151 is fluidly connected to lumen 147. Reservoir 151 and electrode 152 can be configured to be operably advanceable from shaft 101, such as via one or more controls on a proximal handle, as is described in reference to FIG. 1 hereabove. Reservoir 151 can be constructed and arranged to be rotated, such as to perform multiple fluid delivery events around a circumference of tissue, such as to create a full or near full circumferential tissue expansion. Lumen 147 is fluidly connected to one or more fluid delivery tubes, not shown but traveling proximally and fluidly connected to a supply of injectable fluid. Electrode 152 is connected to one or more wires, not shown but traveling proximally to a control unit configured to cause electrode 152 to apply an electric field in and/or around reservoir 151. While electrode 152 is shown as a single electrode, multiple electrodes may be employed. Injectate 150 comprises an ionic fluid capable of being driven into at least tissue layers L1 and L2, by the electrical fields created by electrode 152, such as via iontophoretic delivery well known to those of skill in the art. Activation of electrode 152 can be accomplished via one or more controls on a proximal handle or on a device connected to a proximal handle, such as is described in reference to FIG. 1 hereabove.

Referring now to FIG. 10, a side sectional view of a distal portion of a tissue expansion device comprising a side recess portion and protected needle exit port is illustrated, consistent with the present inventive concepts. Device 100 includes shaft 101 with integral side car 106, positioned at or near distal end 102 of shaft 101. Side car 106 comprises a guidewire lumen 106', such that shaft 101 can be advanced and/or exchanged over a guidewire via rapid exchange delivery, as is known to those of skill in the art. Shaft 101 further comprises two lumens, a first lumen 108 which can slidingly receive a fluid delivery element, needle 141, and a second lumen 107, configured to carry a vacuum. Shaft 101 comprises a recess in its side wall, recess 155, relatively proximate distal end 102 of shaft 101. Recess 155 can be positioned in a lumen of tissue, such as a lumen of the duodenum or other gastrointestinal lumen, such as to expand one or more layers of tissue, such as the submucosal layer of the duodenum. An opening 158 is positioned between lumen 107 and recess 155, such that an applied vacuum can be introduced to recess 155 via lumen 107, such as to draw tissue into recess 155 as shown as described in reference to FIGS. 10A and 10B hereinbelow.

Needle 141 includes lumen 147, which is fluidly connected to one or more fluid delivery tubes, not shown but such as one or more fluid delivery tubes in fluid communication with a supply of fluid, such as is described in reference to device 100 of FIG. 1 hereabove. Needle 141 is configured to be operably advanceable along the axis of shaft 101 and lumen 108, such as via one or more controls on a proximal handle, also as is described in reference to FIG. 1 hereabove, such as to have its distal end exit lumen 108 and enter recess 155. A mechanical stop 157 is positioned within lumen of 108. A collar 156 is attached to needle 141, such that advancement of needle 141 is limited when collar 156 makes contact with mechanical stop 157. In some embodiments, the position of collar 156 and/or stop 157 can be adjusted, such as via one or more controls positioned on a proximal handle, such as to adjust the permitted travel of needle 141. In some embodiments, the length of needle 141 is chosen such that it is longer than the axial length of recess 155, such as to prevent needle 141 from exiting device 100 if needle 141 were to become detached.

In some embodiments, device 100 includes an imaging component, visualization element 165 which is connected to cables 166. Imaging component 165 is configured to provide an image to the operator, such as via one or more visual displays, not shown but connected to cables 166 and positioned in view of one or more operators of device 100. Imaging component 165 may comprise an imaging element selected from the group consisting of: an ultrasound imager; an optical coherence domain reflectometry (OCDR) imager; an optical coherence tomography (OCT) imager; confocal endomicroscopy via either scanning or structured illumination; and combinations of these. Cables 166 may comprise electrical wires, optical fibers and/or one or more rotating shafts, such as to provide power or otherwise enable imaging component 165 to provide an image. Images provided by imaging component 165 can be used to determine sufficiency or otherwise assess the tissue expansion caused by delivering fluid to one or more tissue layers via needle 141.

Referring now to FIG. 10A, the distal portion of shaft 101 and recess 155 have been positioned proximate tissue, such as gastrointestinal tissue, and a vacuum has been applied to recess 155 via port 158 and lumen 107, such as via a vacuum source within and/or attached to a proximal handle. As the vacuum is applied, tissue proximate recess 155 is drawn into recess 155 as illustrated in FIG. 10A. In some embodiments, recess 155 comprises a geometry and size to precisely cause tissue expansion of specific layers of the intestinal anatomy. For example, recess 155 may comprise a geometry and size to cause the mucosal layer (<1 mm thick) to enter recess 155 without including the muscularis layer. In these embodiments, the spongy submucosal layer stretches and enlarges as tissue is drawn into recess 155, creating a larger target for needle 141 insertion. Minimizing the recess 155 width can be used to prevent drawing the full thickness of tissue into recess 155 by vacuum applied through lumen 107. In some embodiments, recess 155 comprises a width less than 2.0 mm, such as a width less than 1.5 mm or less than 1.0 mm. Minimizing recess 155 axial length can be used to improve needle 141 penetration into tissue drawn into recess 155, such as when the distal end of recess 155 provides a normal force in reaction to needle 141 tissue penetration. In some embodiments, recess 155 length is less than 5.0 mm, such as a length less than 4.0 mm or less than 3.0 mm. In some embodiments, recess 155 comprises a width approximating 1.5 mm and a length approximating 4.0 mm. In some embodiments, lumen 107 and needle 141 are each contained in a single tube, such as the dual lumen tube described in reference to FIG. 5C hereabove.

Referring now to FIG. 10B, while maintaining a vacuum in lumen 107, needle 141 has been axially advanced into the tissue, as illustrated. Advancement of needle 141 can be accomplished by one or more controls on the proximal end of shaft 101, such as controls integral to a handle such as are described in reference to handle 110 of FIG. 1. After insertion of needle 141 into the tissue contained within recess 155, such as via fluid delivery tubes which travel proximally to one or more sources of fluid on the proximal end of shaft 101. In some embodiments, recess 155 is sized and configured to limit the excursion distance between the location where the tip of needle 141 enters recess 155 and the location where needle 141 first penetrates tissue. Minimizing this distance can prevent bunching or stretching of tissue or otherwise improve needle 141 penetration into tissue captured within recess 155.

Shaft 101 and recess 155 of FIGS. 10, 10A and 10B can be constructed and arranged to be rotated. In these embodiments, multiple fluid delivery events can be performed around a circumference of tissue, such as to draw a series of tissue sections via vacuum into recess 155, followed by multiple advancements of needle 141 and delivery of fluid, such as to create a full or near full circumferential tissue expansion.

Referring now to FIG. 11, a side sectional view of a distal portion of a tissue expansion device comprising an end recess portion and protected needle exit port is illustrated, consistent with the present inventive concepts. Shaft 101' and recess portion 155' are similar to shaft 101 and recess 155 of FIG. 10 except recess portion 155' is positioned at the distal end 102 of shaft 101'.

Shaft 101' further comprises a first lumen 108 which slidingly receives fluid delivery tube 121 and a fluid delivery element, needle 141. Shaft 101' further comprises a second lumen 107, configured to carry a vacuum. Recess 155' and lumen 107 are constructed and arranged to withdraw tissue into recess 155' and apply tension to this tissue to resist forces encountered during penetration of the tissue by needle 141.

Recess 155' can be positioned in a lumen of tissue, such as a lumen of the duodenum or other gastrointestinal lumen, such as to expand one or more layers of tissue, such as the submucosal layer of the duodenum. An opening 158' is positioned between lumen 107 and recess 155', such that an applied vacuum can be introduced to recess 155' via lumen 107, such as to draw tissue into recess 155' as shown as described in reference to FIGS. 10A and 10B hereabove.

Needle 141 includes lumen 147, which is fluidly connected to fluid delivery tube 121 which attaches at its proximal end to one or more supplies of fluid, such as is described in reference to device 100 of FIG. 1 hereabove. Needle 141 is configured to be operably advanceable along the axis of shaft 101' and lumen 108, such as via one or more controls on a proximal handle, also as is described in reference to FIG. 1 hereabove, such as to exit lumen 108 and enter recess 155'. In typically use, distal end 102 of shaft 101 is positioned proximate tissue, vacuum is applied via opening 158', after which needle 141 is advanced into the capture tissue and one or more fluids are injected into the tissue via lumen 108 and fluid delivery tube 121, causing one or more tissue layers to expand.

Figure 12:
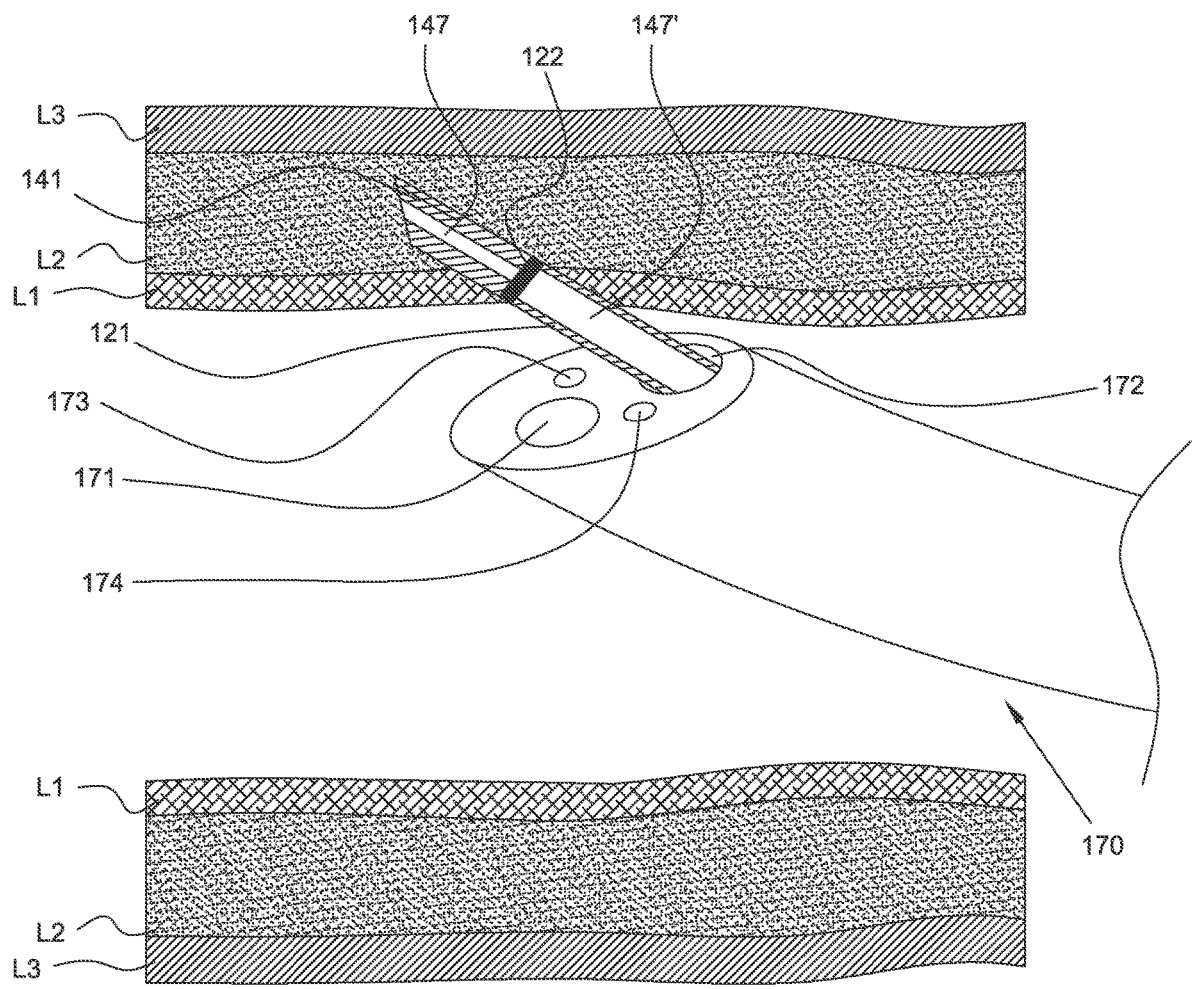
FIG. 12 is a side sectional view of the distal portion of a tissue expansion device comprising an endoscope and an advanceable needle and positioned in a body lumen, consistent with the present inventive concepts.

Referring now to FIG. 12, a side sectional view of the distal portion of a tissue expansion device comprising an endoscope and an advanceable needle is illustrated, consistent with the present inventive concepts. Endoscope 170 has been advanced through luminal tissue, such as through the gastrointestinal tract such as to a location in the duodenum. The tissue comprises multiple layers, such as innermost layer L1, deeper layer L2 and yet deeper layer L3. Endoscope 170 has had its distal end deflected, via one or more steering controls common to endoscope devices, such that needle 141 can be axially advanced to penetrate layer L1 and L2 of tissue, while avoiding penetration of layer L3, such as to penetrate a mucosal and submucosal layer of the gastrointestinal tract, while avoid penetrating deeper layers such as the serosa.

Needle 141, including a lumen 147, may be configured to be operably advanceable from working channel 172 of endoscope 170, such as via one or more controls. Endoscope 170 can be constructed and arranged to be rotated (e.g. when needle 141 is retracted), such as to perform multiple fluid delivery events around a circumference of tissue, such as to create a full or near full circumferential tissue expansion. Needle 141 and lumen 147 are fluidly connected to fluid delivery tube 121 (e.g. a hypotube) via bond joint 122. Lumen 147 is fluidly attached to lumen 147' of fluid delivery tube 121. In some embodiments, lumen 147' is a larger diameter than lumen 147 as shown in FIG. 12, such as to reduce the pressure required to deliver fluid through fluid delivery tube 121. Fluid delivery tube 121 travels proximally and fluidly connected to a supply of injectable fluid, such as a syringe or pumping assembly. Fluid can be delivered to tissue out of distal end of needle 141, such as via one or more controls on a proximal handle or on a device connected to a proximal handle, such as is described in reference to FIG. 1 hereabove.

In some embodiments, needle 141 and/or fluid delivery tube 121 comprise a flexibility and radial support that allow flexing without luminal collapse, such that needle 141 can translate toward the center of the lumen as tissue layer L2 expands.

Endoscope 170 includes a camera 171, positioned to allow an operator to visualize penetration of needle 141 into tissue, as well as the expansion of one or more tissue layers such as layer L2 shown. In some embodiments, the injected fluid comprises a dye or other visualizable colorant that can be used to quantify or otherwise assess the amount of tissue expansion (e.g. the deeper the color visualized at a location, the thicker the expansion at that location). Alternatively or additionally, endoscope 170 may comprise another visualization device, such as a device selected from the group consisting of: an ultrasound imager; an optical coherence domain reflectometry (OCDR) imager; an optical coherence tomography (OCT) imager; and combinations of these. Endoscope 170 can further comprise a source of light, such as LED 173, such as to deliver visible light and/or infrared light. Endoscope 170 can further comprise a second working channel 174, such as a working channel sized to slidingly receive a tissue manipulating device, such as a tissue manipulating device described in reference to FIG. 18 herebelow.

Figure 13:
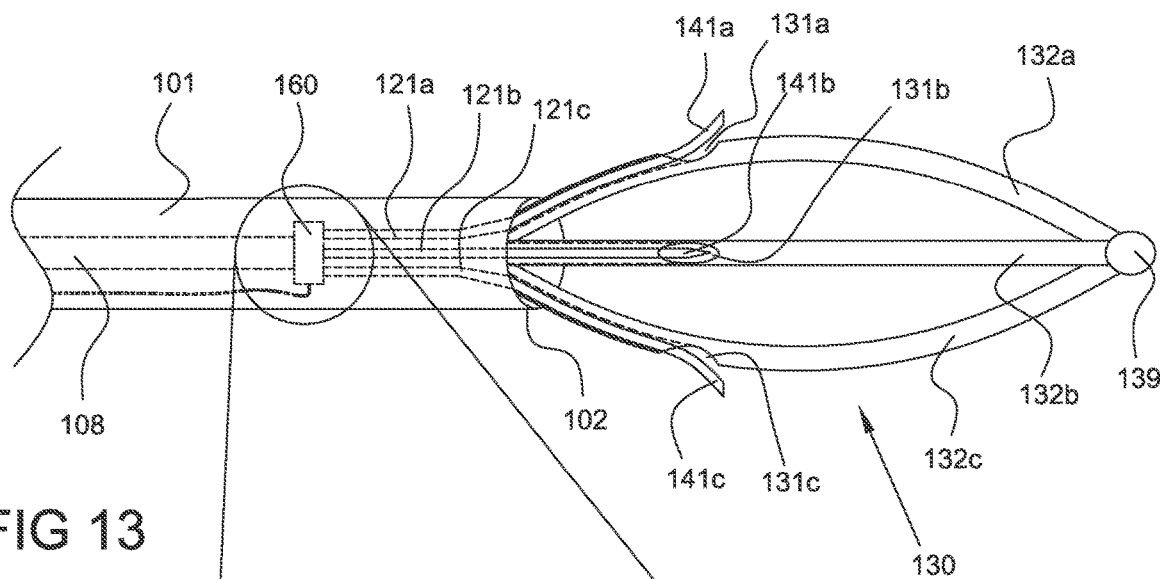
FIG. 13 is a side view of the distal portion of a tissue expansion device comprising multiple needles and a fluid dispersion manifold, consistent with the present inventive concepts.

Referring now to FIG. 13, a side view of the distal portion of a tissue expansion device comprising multiple needles and a fluid dispersion manifold is illustrated, consistent with the present inventive concepts. Expandable assembly 130 is shown distal to distal end 102 of shaft 101. Expandable assembly 130 comprises at least three support arms, such as support arms 132a, 132b and 132c shown. Support arms 132a, 132b and 132c can be resiliently biased in the radially expanded condition shown in FIG. 13. In some embodiments, expandable assembly 130 is slidingly received by shaft 101, such that retraction of expandable assembly 130 into shaft 101 causes expandable assembly 130 to radially compress. In other embodiments, expandable assembly 130 may be fixed relative to shaft 101, such as when expandable assembly 130 is inserted through an endoscope whose working channel radially compresses expandable assembly. Tip 139 can connect and/or surround the distal ends of support arms 132a, 132b and 132c, and tip 139 may include an atraumatic covering such as an elastomer or other relatively soft material. In an alternative embodiment, expandable assembly 130 comprises two support arms, such as two support arms 132a and 132b positioned 180° from each other.

Support arms 132a, 132b and 132c each comprise a radially outward facing opening, openings 131a, 131b and 132c respectively. A fluid delivery element, such as needles 141a, 141b and 141c, are slidingly received by arms 132a, 132b and 132c, respectively. Needles 141a, 141b and 141c are constructed and arranged to be operably advanced out of openings 131a, 131b and 131c, respectively, such as has been described in detail hereabove.

Needles 141a, 141b and 141c are each attached to a fluid delivery tube, fluid delivery tubes 121a, 121b and 121c respectively. Fluid delivery tubes 121a, 121b and 121c are fluidly attached to a fluid dispersion manifold, valve assembly 160, which in turn is fluidly attached to a single fluid delivery tube, lumen 108. Lumen 108 travels proximally and is fluidly connected to one or more sources of injectable fluid, such as has been described in detail hereabove.

Figure 13A:
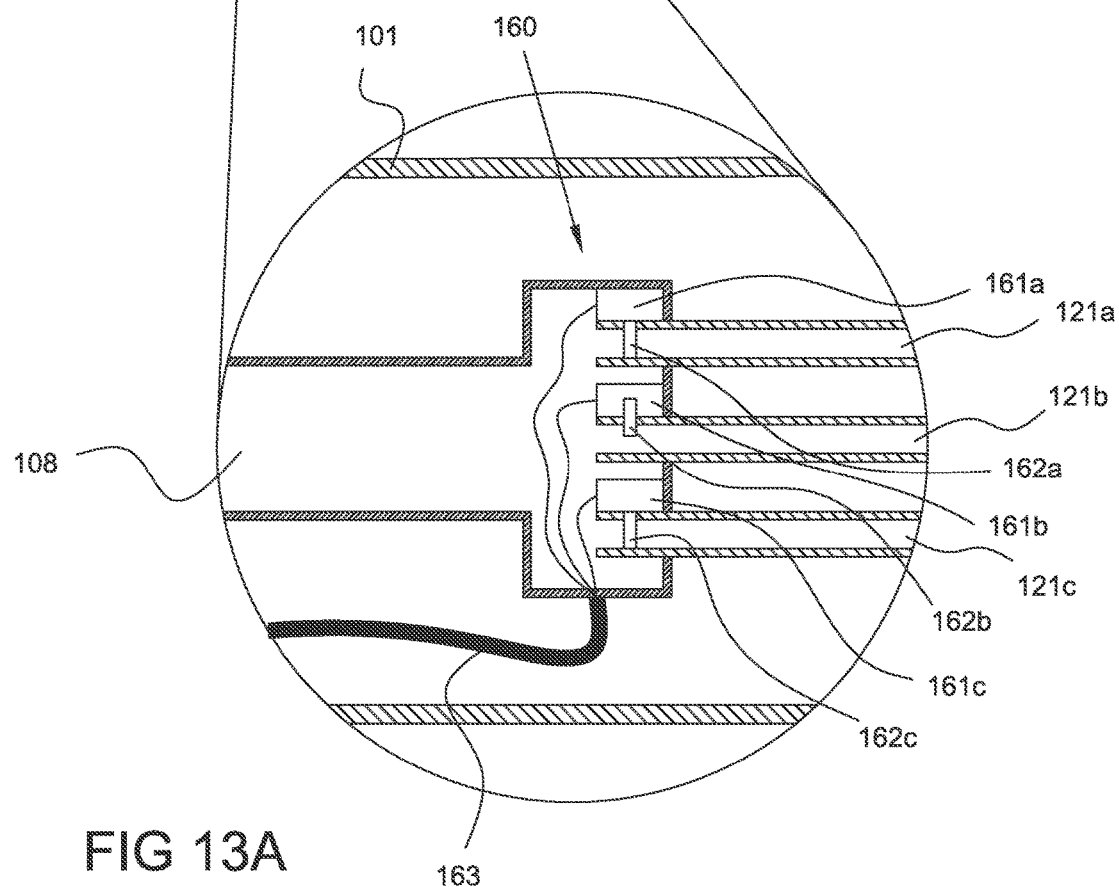
FIG. 13A is a magnified view of the fluid dispersion manifold of FIG. 13, consistent with the present inventive concepts.

Referring now to FIG. 13A, a magnified sectional view of the valve assembly 160 of FIG. 13 is illustrated, consistent with the present inventive concepts. Valve assembly 160 is connected at its proximal end to lumen 108. Valve assembly 160 comprises three sets of solenoids and pistons, including solenoids 161a, 161b and 161c, which advance and retract pistons 162a, 162b and 162c, respectively. Pistons 162a, 162b and 162c are positioned in fluid delivery tubes 121a, 121b and 121c, such as to cause a flow path between each tube and lumen 108 to be open or closed. A cable of wires 163 is attached on its distal end to solenoids 161a, 161b and 161c. Wires 163 travel proximally, such as to a control circuit included in a handle and configured to allow an operator to independently cause fluid to flow to any or all of fluid delivery tubes 121a, 121b and 121c.

Figure 13B:
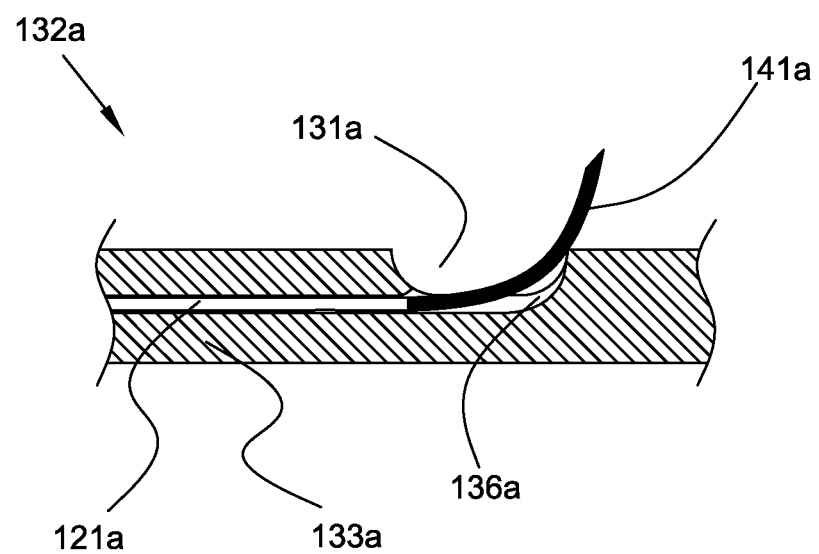
FIG. 13B is a magnified sectional view of a support arm of FIG. 13, consistent with present inventive concepts.

Referring now to FIG. 13B, a magnified sectional view of a support arm of FIG. 13 is illustrated, consistent with the present inventive concepts. Support arm 132a comprises proximal segment 133a, configured to slidingly receive a fluid delivery element, needle 141a, and includes opening 131a, Needle 141a and attached fluid delivery tube 121a have been advanced, such as via one or more controls on a proximal handle, such as handle 110 of FIG. 1, configured to allow an operator to advance needle 141a, In some embodiments, as needle 141a is advanced, it makes contact with ramp 136a, positioned proximate opening 131a and typically a hard surface configured to direct needle 141a at a pre-determined trajectory, such as to penetrate one or more layers of tissue, such as one or more layers of gastrointestinal tissue.

Figure 14:
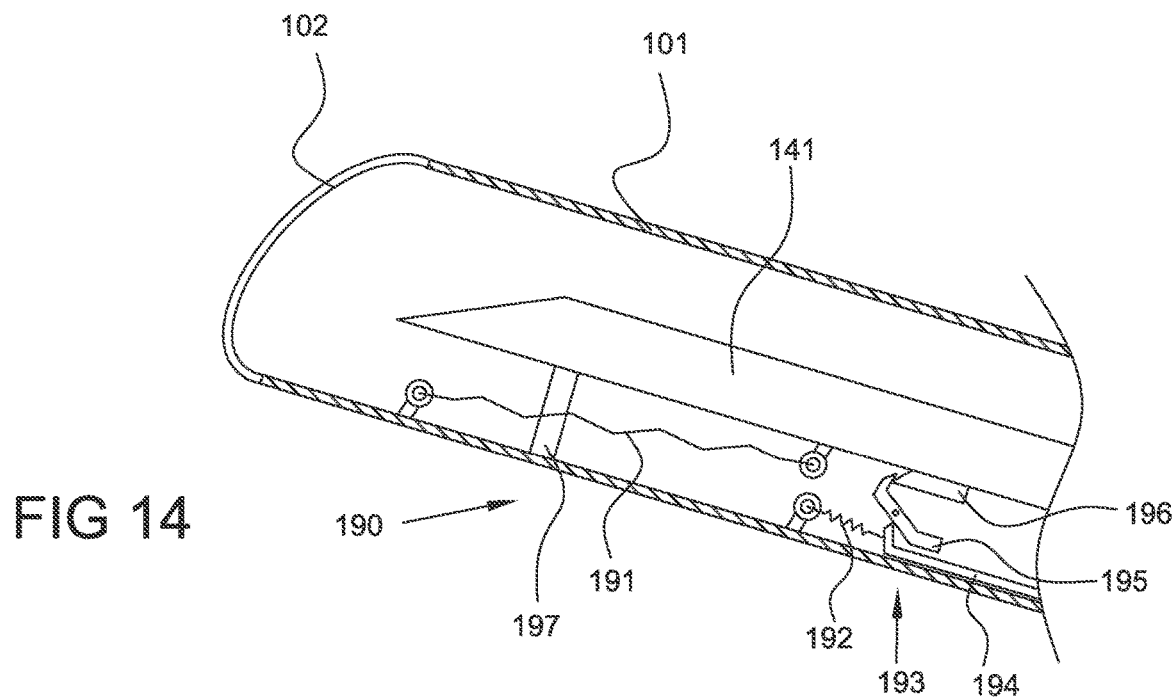
FIG. 14 is a side sectional view of a distal portion of a tissue expansion device comprising a spring-loaded needle injector, consistent with the present inventive concepts.

Referring now to FIG. 14, a side sectional view of a distal portion of a tissue expansion device comprising a spring-loaded needle injector is illustrated, consistent with the present inventive concepts. Shaft 101 includes distal end 102 and surrounds a fluid delivery element, such as needle 141. An injection assembly 190 is included and configured to allow an operator to cause a spring-force driven advancement of needle 141, such as an automated advancement of a predetermined distance and/or pre-determined force into tissue. An optional mechanical stop may be included, projection 197, attached to an inner wall of shaft 101.

Injection assembly 190 includes a spring 191, which is attached on one end to needle 141 and on its other end to an inner wall of shaft 101. Spring 191 is positioned to exert an advancing force (i.e. to the left of the page as shown) on needle 141 when needle 141 is in the retracted state shown in FIG. 14. Injection assembly 190 further includes a latching assembly 193 comprising control rod 194 which is attached to one end of biasing spring 192. The other end of biasing spring 192 is attached to an inner wall of shaft 101, such as to create a biasing force on rod 194 toward the left of the page as shown. Control rod 194 travels proximally and is typically attached to an advancement and retraction control on a handle on the proximal end of shaft 101, such as has been described in detail in reference to FIG. 1 hereabove. Control rod 194 operably engages a pivoting latch 195, which releasably engages a radial extending portion of needle 141, projection 196. When positioned as shown in FIG. 14, pivoting latch 195 applies a force to needle 141 via projection 196 that prevents spring 191 from advancing needle 141 out of the distal end 102 of shaft 101.

Figure 14A:
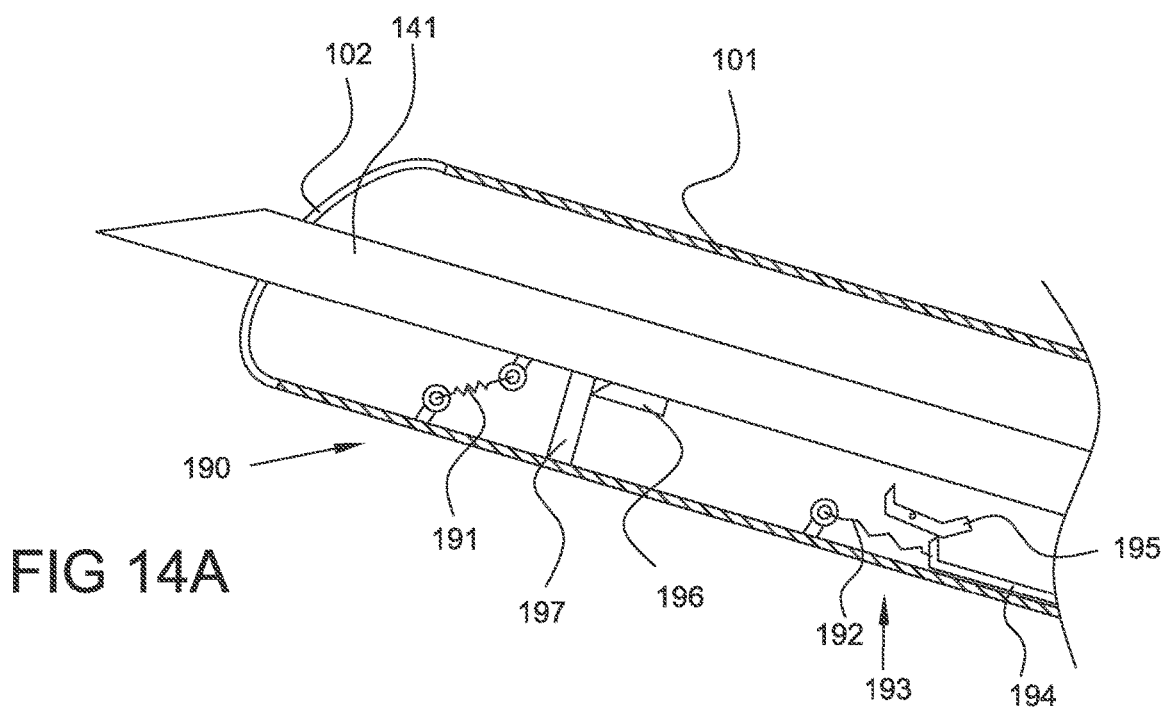
FIG. 14A is a side sectional view of the distal portion of the tissue expansion device of FIG. 14, after advancement of the needle by the spring-loaded injector, consistent with the present inventive concepts.

Referring now to FIG. 14A, control rod 194 has been retracted, causing pivoting latch 194 to pivot and release engagement with projection 196. The force applied by spring 191 causes needle 141 to advance to the left of the page as shown. In some embodiments, a mechanical stop is included, projection 197, causing needle 141 to advance a maximum distance, such as to a target tissue layer and/or target tissue depth. After advancement, one or more fluids can be delivered to one or more tissue layers as has been described in detail hereabove.

In some embodiments, projection 197 can be moved along the axis of shaft 101, such as when slidingly received by a slot and securement mechanism, each not shown but configured to allow operator adjustment of the position of projection 197. Subsequent retraction of needle 141, such as by one or more controls on a proximal handle as has been described in detail hereabove, will cause injection assembly 190 and latching assembly 193 to reset to the condition shown in FIG. 14, ready for repositioning of the device, and additional spring-loaded advancement of needle 141 into tissue to support tissue expansion via fluid delivery. Injection assembly 190 may be included in one or more of the tissue expansion devices described herein, such as to allow automated fluid delivery advancement, e.g. advancement of needle 141 and/or to allow controlled force of tissue penetration and/or controllable advancement distance.

Figure 15:
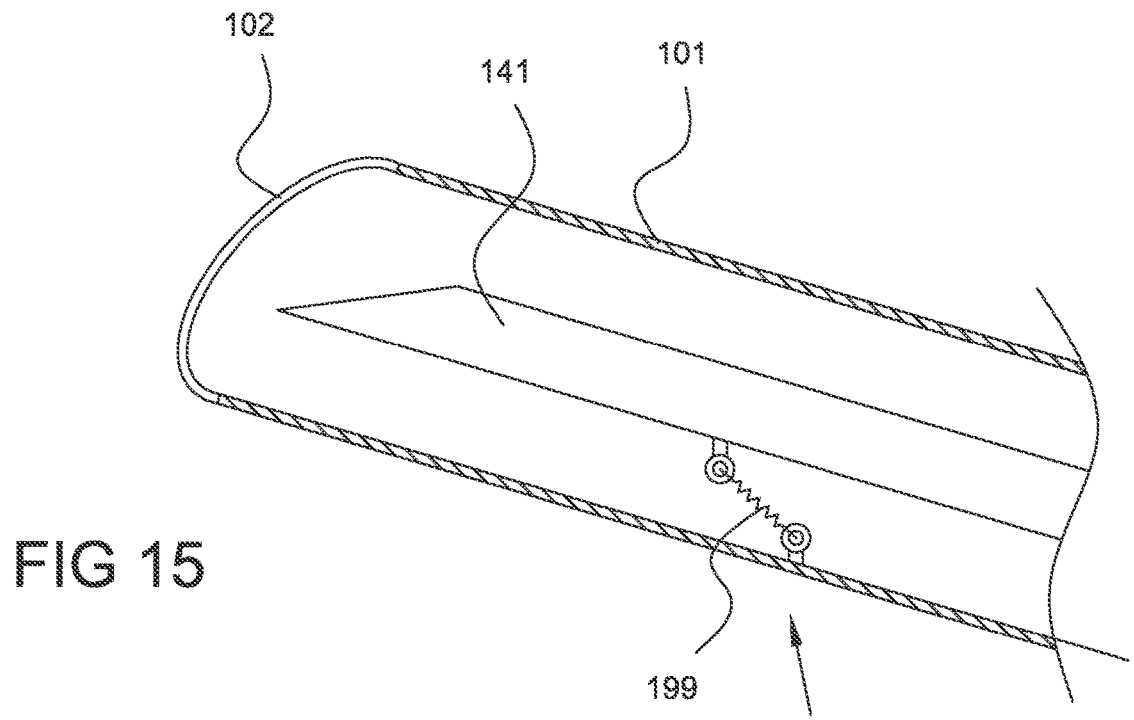
FIG. 15 is a side sectional view of a distal portion of a tissue expansion device comprising a needle biased in a retracted state, consistent with the present inventive concepts.

Referring now to FIG. 15, a side sectional view of a distal portion of a tissue expansion device comprising a needle biased in a retracted state is illustrated, consistent with the present inventive concepts. Shaft 101 includes distal end 102 and surrounds a fluid delivery element, such as needle 141. A biasing assembly 198 includes a spring 199 connected on one end to needle 141 and on its other end to an inner wall of shaft 101. Spring 199 is attached and oriented to provide a biasing force tending needle 141 to be in a retracted state, such as the retracted state shown in FIG. 15.

Figure 15A:
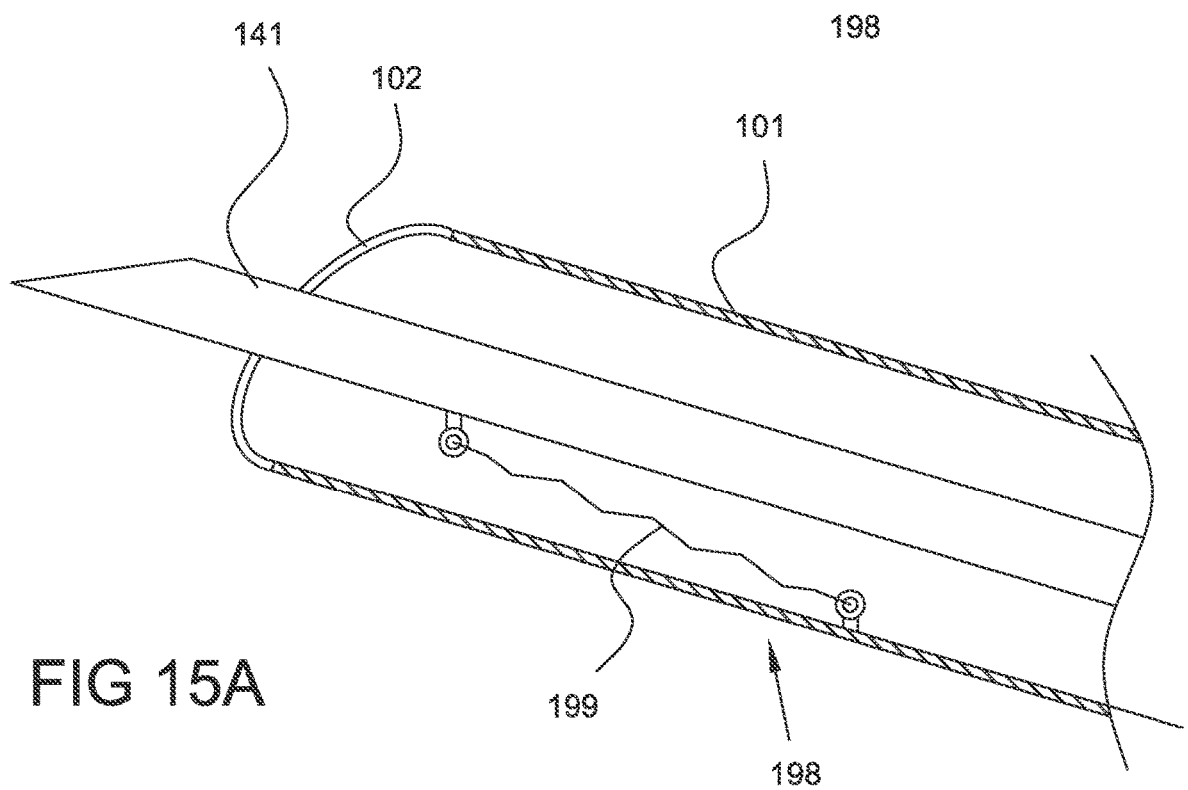
FIG. 15A is a side sectional view of the distal portion of the tissue expansion device of FIG. 15, after advancement of the needle, consistent with the present inventive concepts.

Referring now to FIG. 15A, needle 141 has been advanced (to the left of the page as shown), such as via one or more controls included in a proximal handle as has been described in detail hereabove. Spring 199 is extended, placing a biasing force tending to cause needle 141 to retract. Biasing assembly 198 may be included in one or more of the tissue expansion devices described herein, such as to prevent an operator from inadvertently leaving a fluid delivery element, such as needle 141, in an advanced position.

Figure 16:
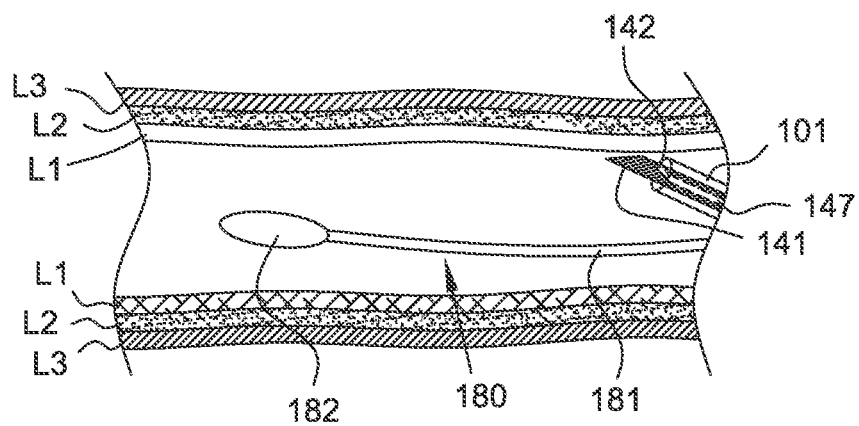
FIG. 16 is a side sectional view of a distal portion of a tissue expansion device comprising a luminal occlusion assembly and a fluid delivery element comprising a needle, each positioned in a body lumen, consistent with the present inventive concepts.

Referring now to FIG. 16, a side sectional view of a luminal occlusion assembly and fluid delivery element comprising a needle is illustrated, consistent with the present inventive concepts. A fluid delivery element, needle 141 has been positioned in a lumen of tissue, such as a lumen of the duodenum or other gastrointestinal lumen. The tissue comprises multiple layers, such as innermost layer L1, deeper layer L2 and yet deeper layer L3. Needle 141, including a side exit port, opening 142 which is fluidly attached to lumen 147, can be configured to be operably advanceable from shaft 101, such as via one or more controls on a proximal handle, as is described in reference to FIG. 1 hereabove. Shaft 101 can be constructed and arranged to be rotated (e.g. when needle 141 retracted), such as to perform multiple fluid delivery events around a circumference of tissue, such as to create a full or near full circumferential tissue expansion. Lumen 147 is fluidly connected to one or more fluid delivery tubes, not shown but traveling proximally and fluidly connected to a supply of injectable fluid. Fluid can be delivered to tissue out of the distal end of needle 141, such as via one or more controls on a proximal handle or on a device connected to a proximal handle, such as is described in reference to FIG. 1 hereabove.

An assembly for fully or partially occluding a lumen, occlusion assembly 180 is positioned relatively proximate needle 141, such as to occlude flow of one or more fluids in the lumen surrounded by layer L1 (e.g. insufflation fluids), and/or to occlude flow of fluid within one or more of tissue layers L1, L2 and/or L3 (e.g. the fluid injected by needle 141, blood and/or other fluids within layers L1, L2 and/or L3). Occlusion assembly 180 includes an expandable device, such as balloon 182 which can be operably expanded, such as via the delivery of one or more fluids such as air, $CO_2$ and/or saline into balloon 182 via inflation tube 181. Inflation tube 181 travels proximally and connects to an inflation port or other supply of fluids, such as on a handle as has been described hereabove. In FIG. 16, balloon 182 has yet to be expanded, and needle 141 has not yet penetrated tissue layer L1. In alternative embodiments, occlusion assembly 180 may comprise another expandable element, such as an expandable cage or basket configured to apply force to one or more layers of tissue.

Figure 16A:
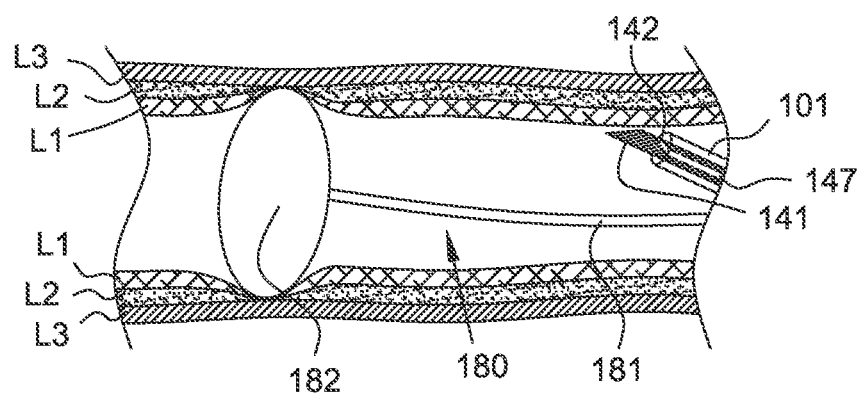
FIG. 16A is a side sectional view of the luminal occlusion assembly and fluid delivery element of FIG. 16, after the luminal occlusion assembly has been brought into contact with tissue, consistent with the present inventive concepts.

Referring now to FIG. 16A, balloon 182 is inflated to contact tissue layer L1, such as with a full or partial circumferential contact. The level of expansion may be chosen to compress one or more tissue layers such as L1, L2 and/or L3, as shown.

Figure 16B:
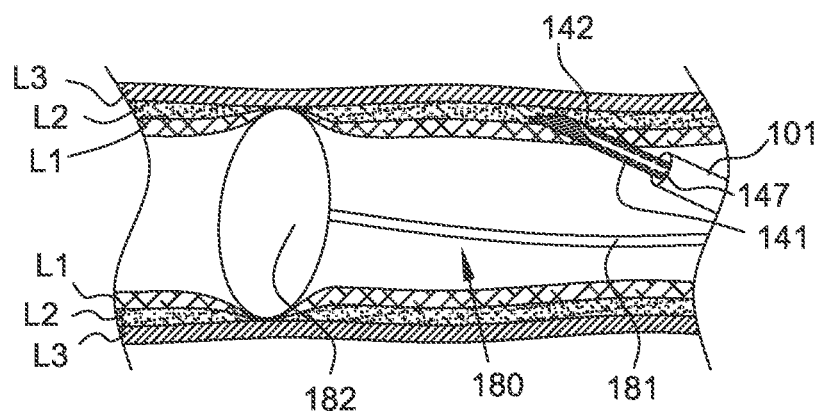
FIG. 16B is a side sectional view of the luminal occlusion assembly and fluid delivery element of FIGS. 16 and 16A, after the needle has been advanced into tissue, consistent with the present inventive concepts.

Referring now to FIG. 16B, needle 141 has been advanced through tissue layer L1 and into tissue layer L2, positioning opening 142 in tissue layer L2. Balloon 182 has been maintained in its inflated state.

Figure 16C:
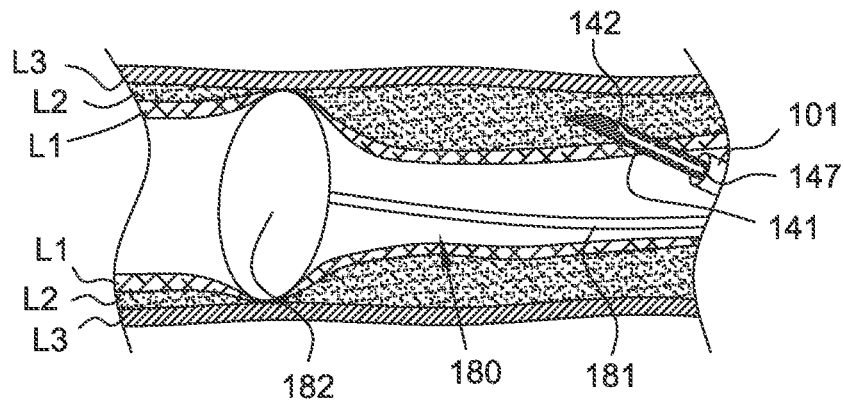
FIG. 16C is a side sectional view of the luminal occlusion assembly and fluid delivery element of FIGS. 16, 16A and 16B, after a fluid has been advanced through an opening in the needle and into the tissue, consistent with the present inventive concepts.

Referring now to FIG. 16C, fluid has been advanced through opening 142 into tissue layer L2, causing tissue layer L2 to expand as shown. Maintenance of balloon 182 in the inflated state reduces and/or prevents migration of fluid beyond the position of balloon 182, such as to direct the expansion of tissue circumferentially and/or in a direction to the right of balloon 182 as shown on the page.

While balloon 182 is shown positioned distal to the penetration site of needle 141 into tissue, in alternative methods balloon 182 can be placed proximally to needle 141. While occlusion assembly 180 is illustrated have a single balloon 182, in alternative embodiments, multiple balloons or other inflatable elements may be included, such as to be positioned distal and/or proximal to the penetration site of needle 141. In these multiple balloon embodiments, a fluid delivery element such as needle 141 may be configured to be deployed between a first balloon and a second balloon.

Referring now to FIG. 17, the distal portion of a tissue expansion device including a fluid delivery element with an operator adjustable needle trajectory guide is illustrated, consistent with the present inventive concepts. Shaft 101 includes distal end 102 and an opening 131 proximate distal end 102. Shaft 101 surrounds a fluid delivery element, needle 141, configured to be advanced into one or more tissue layers to support fluid delivery to expand the one or more tissue layers. Needle 141 passes through a needle guide assembly 115. Needle guide assembly 115 comprises needle guide 117, typically a metal or other rigid material configured to slidingly receive needle 141 and direct a distal portion of needle 141 into tissue. Needle guide assembly 115 further comprises a pivot point, pin 116, which is slidingly received by guide 117 and about which needle guide 117 can pivot. Needle guide 117 is attached to cable 104, which travels proximally to a control, not shown but typically an operator control on a handle configured to advance and/or retract cable 104. Cable 104 can be advanced and/or retracted to cause needle guide 117 to pivot, such as to change the trajectory that needle 141 exits opening 131 of shaft 101. In FIG. 17, cable 104 and needle guide 117 are positioned such that needle 141 exits shaft 101 at approximately 90°.

Referring now to FIG. 17A, cable 104 has been retracted, causing the trajectory taken by needle 141 to tend toward distal end 102 of shaft 101.

Referring now to FIG. 17B, cable 104 has been advanced, causing the trajectory taken by needle 141 to tend away from distal end 102 of shaft 101 (e.g. toward the proximal end of shaft 101.

Figure 18:
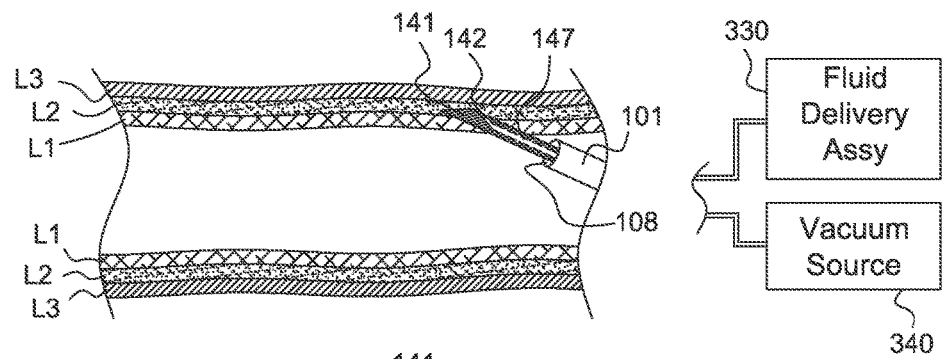
FIG. 18 is a side sectional view of a fluid delivery element comprising a needle with a side hole and positioned with the needle penetrating into a second tissue layer of a body lumen, consistent with the present inventive concepts.

Referring now to FIG. 18, a side sectional view of a fluid delivery element comprising a needle with a side hole is illustrated, consistent with the present inventive concepts. The needle has been advanced to penetrate into a second layer of a body lumen. A fluid delivery element comprises needle 141, which includes a solid tip, a lumen 147, and a side hole, opening 142 as shown. Lumen 147 is fluidly connected to one or more fluid delivery tubes, not shown but traveling proximally to connect to a fluid delivery assembly, such as fluid delivery assembly 330 described herein. The fluid delivery assembly 330 is configured to deliver one or more fluids, as has been described hereabove. Shaft 101 includes lumen 108, through which needle 141 is slidingly advanced. In some embodiments, lumen 108 and/or another lumen of shaft 101 is fluidly attached to a source of vacuum, such as vacuum source 340 described herein. The vacuum source 340 may be set to a pre-determined vacuum pressure and/or it may be operator adjustable. In FIG. 18, needle 141 and shaft 101 have been inserted into a body lumen comprising layers L1, L2 and L3, such as through the working channel of an endoscope or other body access device, or over a guidewire, neither shown but described in reference to other embodiments herein. Needle 141 has been advanced into tissue layer L2. A vacuum may have been applied to lumen 108 by vacuum source 340 as needle 141 was advanced into tissue.

Figure 18A:
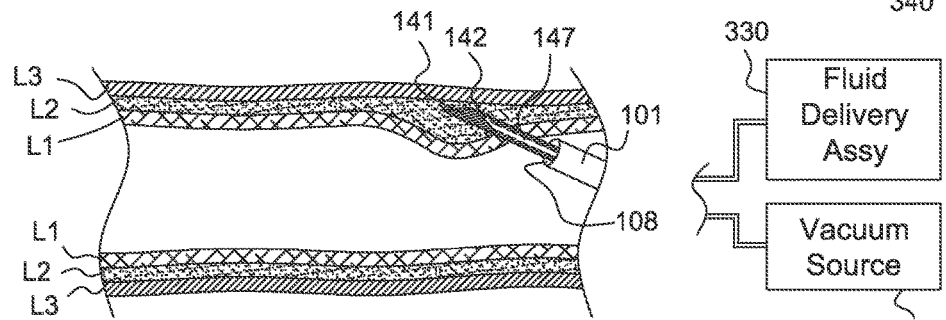
FIG. 18A is a side sectional view of the fluid delivery element of FIG. 18 after injected fluid has expanded the second layer of tissue, consistent with the present inventive concepts.

Referring now to FIG. 18A, fluid has been injected from a fluid delivery assembly, through lumen 147 and opening 142 to cause expansion of tissue layer L2. During injection, a vacuum may have been applied to lumen 108 via vacuum source 340.

Figure 18B:
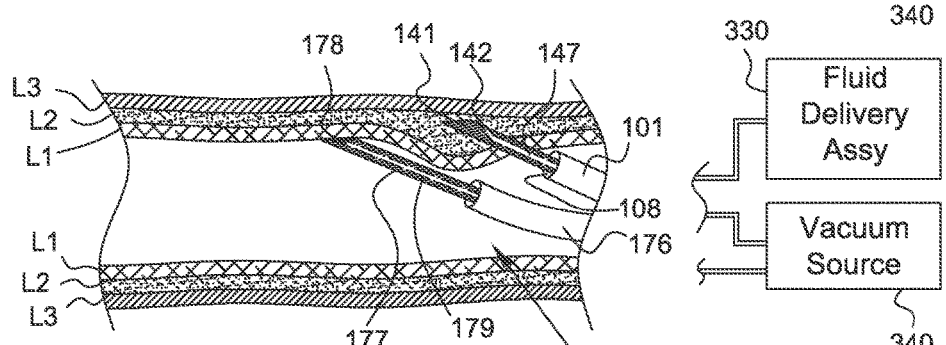
FIG. 18B is a side sectional view of the fluid delivery element of FIGS. 18 and 18A, after the introduction into the body lumen of a tissue manipulating assembly which has been brought into contact with a luminal wall proximate the injection site, consistent with the present inventive concepts.

Referring now to FIG. 18B, a tissue manipulating assembly 175 has been introduced to a site proximate the tissue penetration site of needle 141. Tissue manipulating assembly 175 comprises an elongate tube, shaft 176 through which probe 177 has been advanced such that its distal end, including opening 178, is in contact with tissue. A vacuum is applied by vacuum source 340 through lumen 179 to opening 178. A vacuum may have simultaneously been applied to lumen 108 of shaft 101.

Figure 18C:
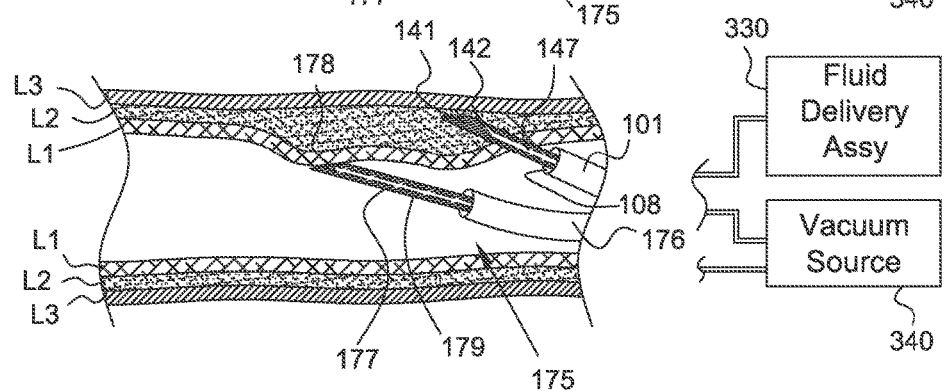
FIG. 18C is a side sectional view of the fluid delivery element and tissue manipulating assembly of FIG. 18B, after a force has been applied to the luminal wall causing modification to the tissue expansion, consistent with the present inventive concepts.

Referring now to FIG. 18C, tissue manipulating assembly 175 has been repositioned, while a vacuum remains applied via lumen 179 and opening 178, causing a force to be applied to the contacted tissue. The applied force causes the geometry of the expanded tissue and/or the fluid contained within the expanded tissue, to be operator adjusted. In some embodiments, tissue manipulation is performed during injection of fluid into tissue via needle 141, such as to direct the flow of fluid within the tissue. The applied force can be used to cause the tissue to "tent", such as to adjust the expanded tissue area and/or to create a greater target for penetration by needle 141.

In some embodiments, a visualization device, such as a camera integral to or inserted through an endoscope, such as the visualization element described in reference to FIG. 10 hereabove, is used to adjust the expanded tissue geometry. In some embodiments, fluid is continuously or intermittently injected as various forces are applied to tissue by tissue manipulating assembly 175. In some embodiments, a vacuum is applied to lumen 108 of shaft 101 to provide a second tissue manipulating probe.

While the tissue manipulating assembly 175 of FIGS. 18B and 18C comprises a vacuum assisted device, numerous forms and configurations of devices that can apply a force to tissue are to be considered within the spirit and scope of the present inventive concepts. In some embodiments, the tissue manipulator comprises one or more of: a balloon; an expandable ring; a vacuum port; a grasper such as a pair of articulating jaws; a radially expandable cage; a radially deployable arm; and combinations of these.

Referring now to FIG. 19, a system for expanding tissue as well as for ablating or otherwise treating target tissue is illustrated, consistent with the present inventive concepts. System 300 is constructed and arranged to treat target tissue 10, including one or more tissue portions. System 300 may include one or more ablation devices or ablation elements, such as those described in International PCT Application Serial Number PCT/US2012/01739, entitled "Devices and Methods for the Treatment of Tissue", filed Jan. 18, 2012; and International PCT Application Serial Number PCT/US2013/28082, entitled "Heat Ablation Systems, Devices and Methods for the Treatment of Tissue", filed Feb. 27, 2013; the contents of which are each incorporated herein by reference in their entirety. In the embodiment of FIG. 19, system 300 includes a multiple filament elongate device 301 comprising shafts 311a and 311b. In some embodiments, device 301 comprises a flexible portion with a diameter less than 6 mm and a length of 100 cm or longer, such as a length of up to 300 cm or other length configured to allow treatment of gastrointestinal tissue including the duodenum, the jejunum and/or the ileum. Shaft 311a has a distal end 312. Shafts 311a and 311b are sized and configured such that shaft 311a is slidingly received by shaft 311b. Shafts 311a and 311b have been inserted through a working channel (e.g. a 6 mm working channel), lumen 351, of endoscope 350. Shafts 311a and 311b may be inserted over a guidewire, such as guidewire 371 shown exiting distal end 312.

Device 301 includes fluid delivery assembly 130, which may comprise an expandable or other fluid delivery assembly comprising one or more fluid delivery elements such as has been described hereabove. Fluid delivery assembly 130 includes at least one fluid delivery element, needle 141, constructed and arranged to deliver fluid to expand one or more layers of tissue. Alternatively or additionally, fluid delivery assembly 130 can comprise additional or alternative fluid delivery elements, such as water jets or other fluid delivery elements described hereabove. In some embodiments, needle 141 is constructed and arranged to deliver fluid to tissue by exiting opening 131 and penetrating tissue, such as has been described in reference to FIG. 4B hereabove. In other embodiments, a vacuum can be applied to opening 131, such as to draw tissue into opening 131 allowing needle 141 to penetrate tissue without exiting opening 131, such as is described in reference to FIGS. 5 and 10 hereabove. System 300 can include source of vacuum, such as vacuum source 340 which can be fluidly attached to an opening or recess of fluid delivery assembly 130, such as a vacuum applied by vacuum source 340 to opening 131.

Fluid delivery assembly 130 can include one or more support arms, such as the various support arms included in the tissue expansion devices of FIGS. 4, 5 and 13 described hereabove. Fluid delivery assembly 130 can comprises a resiliently biased cage or other assembly biased in a radially expanded condition by radially compactable, such as to be inserted through a lumen of an endoscope. Alternatively, fluid delivery assembly 130 may be expandable from a radially compact state to a radially expanded state. Fluid delivery assembly 130 can include an expandable balloon such as a balloon used to position one or more fluid delivery elements proximate tissue to be expanded.

Device 301 further includes an expandable tissue treatment element, expandable treatment element 322b, mounted to shaft 311b. Treatment element 322b may be configured in various forms to treat the target tissue, such as in one or more of the treatment element forms, such as a balloon configured to contain a hot or cold fluid, an array of electrodes configured to deliver RF energy, or other treatment forms. In one embodiment, element 322b comprises an expandable balloon, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In another embodiment, treatment element 322b comprises one or more of an abrasive element configured for abrading tissue; and an energy delivery element such as an energy delivery element configured to deliver RF energy. Shafts 311a and 311b may include one or more lumens passing therethrough, and may comprise wires or optical fibers for transfer of data and/or energy. Shaft 311b may comprise one or more shafts, such as one or more concentric shafts configured to deliver and/or recirculate hot fluid through treatment delivery element 322b, such as to deliver a bolus of hot fluid energy or other thermal dose. Device 301 may comprise multiple treatment elements, such as two or more treatment elements configured to deliver similar and/or dissimilar forms of energy or other treatment. In an alternative embodiment, fluid delivery assembly 130 is not expandable, simply comprising a fluid delivery element capable of delivering fluid to expand one or more layer of tissue.

Endoscope 350 may be a standard endoscope, such as a standard gastrointestinal endoscope, or a customized endoscope, such as an endoscope including sensor 353 configured to provide information related to the tissue treatment of the present inventive concepts. Sensor 353 and the other sensors of system 300 may be a sensor selected from the group consisting of: heat sensors such as thermocouples; impedance sensors such as tissue impedance sensors; pressure sensors; blood sensors; optical sensors such as light sensors; sound sensors such as ultrasound sensors; electromagnetic sensors such as electromagnetic field sensors; and combinations of these. Sensor 353 may be configured to provide information to one or more components of system 300, such as to monitor the treatment of target tissue 10 and/or to treat target tissue 10 in a closed loop fashion. Energy delivery may be modified by one or more sensor readings. In one embodiment, an algorithm processes one or more sensor signals to modify amount of energy delivered, power of energy delivered and/or temperature of energy delivery.

A sensor such as a chemical detection sensor may be included, such as to confirm proper apposition of treatment element 322b, fluid delivery assembly 130 and/or needle 141. In this configuration, a chemical sensor such as a carbon dioxide sensor can be placed distal to treatment element 322b and/or fluid delivery assembly 130, and a fluid such as carbon dioxide gas is introduced proximal to the treatment element 322b and/or fluid delivery assembly 130. Detection of the introduced fluid may indicate inadequate apposition of treatment element 322b, fluid delivery assembly 130 and/or needle 141, such as to prevent inadequate transfer of energy to the target tissue and/or to prevent inadequate tissue expansion.

Endoscope 350 may include camera 352, such as a visible light, ultrasound and/or other visualization device used by the operator of system 300 prior to, during or after the treatment of target tissue 10, such as during insertion or removal of endoscope 350 and/or shafts 311a and 311b. Camera 352 may provide direct visualization of internal body spaces and tissue, such as the internal organs of the gastrointestinal tract. Endoscope 350 may be coupled with or otherwise include a guidewire, such as to allow insertion of endoscope 350 into the jejunum.

System 300 may be configured to perform insufflation of the body lumen. The body lumen may be pressurized, such as by using one or more standard insufflation techniques. Insufflation fluid can be introduced through lumen 354 of endoscope 350. Lumen 354 travels proximally and connects to a source of insufflation liquid or gas, not shown, but typically a source of air, $CO_2$ and/or water. Alternatively or additionally, insufflation fluid may be delivered by device 301, such as through shaft 311a and/or 311b, or through a port in treatment element 322a and/or 322b, ports not shown but fluidly attached to a source of insufflation liquid or gas, also not shown. Alternatively or additionally, a separate device, configured to be inserted through endoscope 350 or to be positioned alongside endoscope 350, may have one or more lumens configured to deliver the insufflation fluid. System 300 may include one or more occlusive elements or devices, such as expandable treatment element 322b, fluid delivery assembly 130, or another expandable device, not shown but configured to radially expand such as to fully or partially occlude the body lumen, such that insufflation pressure can be achieved and/or maintained over time (e.g. reduce or prevent undesired migration of insufflation fluid). The one or more occlusive elements or devices may be positioned proximal to and/or distal to the luminal segment to be insufflated.

The treatment elements and fluid delivery assemblies of the present inventive concepts, such as treatment element 322b and fluid delivery assembly 130, respectively, of FIG.

19, may have a fixed diameter or they may be expandable. Expandable elements may comprise inflatable balloons, expandable cages, radially deployable arms, and the like. Treatment elements may include an energy delivery element or arrays of elements, such as an array of balloon lobes for delivery of thermal energy from a hot fluid. Energy delivery elements may be configured to deliver one or more different forms of energy. Energy may be delivered in constant or varied magnitudes or other energy levels. Energy may be continuous or pulsed, and may be delivered in a closed-loop fashion. Energy delivery may be varied from a first tissue location to a second location, such as a decrease in energy from a first treated location to a second treated location when the second treated location is thinner than the first treated location. Alternatively or additionally, energy delivery may be varied during a single application to a single tissue location, such as by adjusting the amount of energy delivered, or by moving a portion of the energy delivery element, such as by deflating an energy delivery element as has been described in detail hereabove.

Treatment element 322b may be configured to cause the complete or partial destruction of the target tissue, such as the complete or partial destruction of the duodenal mucosa. Treatment element 322b may be configured to remove previously treated and/or untreated tissue. Pressure maintained within treatment element 322b can be set and/or varied to adjust the treatment being performed such as to: adjust the depth of treatment; adjust the force applied by a mechanical abrasion device; adjust the amount of energy applied during thermal energy delivery (e.g. by changing tissue contact); and combinations of these.

Treatment element 322b may include one or more sensors 316b. Sensor 316b may be one or more sensors as described hereabove. Sensor 316b may be a sensor configured to provide information related to the tissue treatment performed by treatment element 322b, such as a visualization sensor mounted to treatment element 322b that is configured to differentiate tissue types that are proximate treatment element 322b, such as to differentiate mucosal and submucosal tissue. Alternatively or additionally, sensor 316b may be a sensor configured to provide information related to the tissue treatment performed by treatment element 322b, such as a temperature sensor mounted to treatment element 322b and configured to monitor the temperature of treatment element 322b and/or tissue proximate treatment element 322b.

Energy Delivery and Fluid Transport Unit (EDU) 330 may be configured to deliver and extract one or more fluids from treatment element 322b, as well as deliver one or more forms of energy to target tissue. In one embodiment, EDU 330 is configured to deliver one or more supplies of hot fluid, such as hot water or saline to a balloon treatment element. In these embodiments, EDU 330 typically includes one or more fluid pumps, such as one or more peristaltic, displacement or other fluid pumps; as well as one or more heat exchangers or other fluid heating elements internal or external to device 301. EDU 330 may be constructed and arranged to rapidly deliver and/or withdraw fluid to and/or from treatment element 322b with one or more fluid transport means. Fluid transport means may include a pump configured to deliver fluid at a flow rate of at least 50 ml/min and/or a pump or vacuum source configured to remove fluid at a flow rate of at least 50 ml/min. A pump or vacuum source may be configured to continuously exchange hot fluid and/or to perform a negative pressure priming event to remove fluid from one or more fluid pathways of device 301. EDU 330 and/or device 301 may include one or more valves in the fluid delivery and/or fluid withdrawal pathways in fluid communication with treatment element 322b. Valves may be configured to control entry of fluid into an area and/or to maintain pressure of fluid within an area. Valves may be used to transition from a heating fluid, such as a fluid of 90° C. maintained in a treatment element for approximately 12 seconds, to a cooling fluid, such as a fluid between 4° C. and 10° C. maintained in the treatment element for approximately 30 to 60 seconds. Typical valves include but are not limited to: duck-bill valves; slit valves; electronically activated valves; pressure relief valves; and combinations of these. EDU 330 may be configured to rapidly inflate and/or deflate treatment element 322b. EDU 330 may be configured to purge the fluid pathways of device 301 with a gas such as air, such as to remove cold or hold fluid from device 301 and/or to remove gas bubbles from device 301.

In another embodiment, EDU 330 is configured to deliver at least radiofrequency (RF) energy, and system 300 includes ground pad 332 configured to be attached to the patient (e.g. on the back of the patient), such that RF energy can be delivered in monopolar delivery mode. Alternatively or additionally, EDU 330 may be configured to deliver energy in a bipolar RF mode, such as when treatment element 322b is configured to deliver RF energy and/or system 300 includes a second energy delivery element, not shown but typically including one or more electrodes or electrically conductive surfaces.

Alternatively or additionally, EDU 330 may be constructed and arranged to deliver fluid to tissue, such as fluid delivered to one or more fluid delivery elements such as needle 141, to cause expansion of one or more tissue layers, such as one or more layers of submucosal layers of the gastrointestinal tract. Fluid can be delivered simultaneously and/or sequentially to multiple fluid delivery elements. EDU may provide fluid in a controlled matter, such as at a controlled pressure or flow rate, or at a pre-determined volume, such as at a pre-determined volume per injection.

System 300 may include controller 360, which typically includes a graphical user interface, not shown but configured to allow one or more operators of system 300 to perform one or more functions such as entering of one or more system input parameters and visualizing and/or recording of one or more system output parameters. Typical system input parameters include but are not limited to: temperature of a fluid to be delivered to a treatment element such as a balloon; temperature of a cooling fluid to be delivered; flow rate of a hot fluid to be delivered; volume of a hot fluid to be delivered; type of energy to be delivered such as RF energy, thermal energy and/or mechanical energy; quantity of energy to be delivered such as a cumulative number of joules of energy to be delivered or peak amount of energy to be delivered; types and levels of combinations of energies to be delivered; energy delivery duration; pulse width modulation percentage of energy delivered; number of reciprocating motions for an abrasive device to transverse; temperature for a treatment element such as target temperature or maximum temperature; insufflation pressure; insufflation duration; fluid flow rate for tissue expansion; flow volume for tissue expansion; vacuum duration for capture into a recess such as recess 155 of FIG. 10; vacuum pressure level such as vacuum level applied to a recess such as recess 155 of FIG. 10; and combinations of these. System input parameters may include information based on patient anatomy or conditions such as pre-procedural or peri-procedural parameters selected from the group consisting of: mucosal density and/or thickness; mucosal "lift" off of submucosa after a submucosal injection; longitudinal location of target tissue within the GI tract; tissue layer thickness such as thickness of a layer pre-expansion, during expansion and/or after expansion by a fluid delivery element such as needle 141; and combinations of these. Typical system output parameters include but are not limited to: temperature information such as tissue and/or treatment element temperature information; pressure information such as balloon pressure information or insufflation pressure information; force information such as level of force applied to tissue information; patient information such as patient physiologic information recorded by one or more sensors; and combinations of these.

Controller 360 and/or one or more other components of system 300 may include an electronics module, such as an electronics module including a processor, memory, software, and the like. Controller 360 is typically configured to allow an operator to initiate, modify and cease treatment of tissue by the various components of system 300, such as by energy delivery unit 330 and/or vacuum source 340. Controller 360 may be configured to adjust the temperature, flow rate and/or pressure of fluid delivered to expandable treatment element 322*b* and/or one or more fluid delivery elements, such as needle 141. Controller 360 may be configured to initiate insufflation and/or to adjust insufflation pressure. Controller 360 may be configured to deliver energy (e.g. from EDU 330) or other tissue treatment in a closed-loop fashion, such as by modifying one or more tissue treatment parameters based on signals from one or more sensors of system 300. Controller 360 may be programmable such as to allow an operator to store predetermined system settings for future use. System 300, EDU 330 and/or controller 360 may be constructed and arranged to modify the temperature, flow rate and/or pressure of a fluid delivered to one or more treatment elements and/or to one or more fluid delivery elements based a parameter selected from the group consisting of: one or more measured properties of delivered fluid; one or more measured properties of the treatment element; one or more properties of the fluid delivery element; one or more measured properties of tissue to be treated; one or more measured properties of tissue to be expanded; and combinations of these.

Controller 360 and EDU 330 may be configured to deliver energy in constant, varied, continuous and discontinuous energy delivery profiles. Pulse width modulation and/or time division multiplexing (TDM) may be incorporated to achieve precision of energy delivery, such as to ensure ablation of target tissue while leaving non-target tissue intact.

System 300 may include a mechanism configured to apply motion to treatment element 322*b* and/or fluid delivery assembly 130, such as motion transfer element 335. Motion transfer element 335 may be configured to rotate and/or axially translate shafts 311*a* and/or 311*b* such that treatment element 322*b* and/or fluid delivery assembly 130, respectively, are rotated and/or translated. Motion transfer element 335 may be configured to rotate treatment element 322*b* and fluid delivery assembly 130 independently or in unison. Motion transfer element 335 may include one or more rotational or linear drive assemblies, such as those including rotational motors, magnetic and other linear actuators, and the like which are operably connected to shaft 311*a* and/or 311*b*. Shafts 311*a* and/or 311*b* are constructed with sufficient column strength and/or torque transfer properties to sufficiently rotate and/or translate treatment element 322*b* and/or fluid delivery assembly 130, respectively, during associated tissue treatment and/or tissue expansion. Motion transfer element 335 may be in communication with controller 360, such as to activate, adjust and/or otherwise control motion transfer element 335 and thus the motion of treatment element 322*b* and/or fluid delivery assembly 130. Motion transfer element 335 may be manually driven and/or automatically (e.g. motor) driven. Alternatively or additionally, motion transfer element 335 may be used to advance or retract treatment element 322*b* and/or fluid delivery assembly 130 from a first position to treat or expand a first portion of target tissue, to a second position to treat or expand a second portion of target tissue. In this embodiment, repositioning of treatment element 322*b* and/or fluid delivery assembly 130 may be configured to provide overlapping treatments and/or tissue expansions.

Controller 360 may be configured to control energy delivery, such as controlling energy delivery to treatment element 322*b*. For example, if treatment element 322*b* is an RF electrode array, and EDU 330 comprises an RF generator, controller 360 may be programmed to provide a specific amount of RF energy for a defined period of time. In another example, if treatment element 322*b* is a heated saline balloon, then controller 360 can be configured to provide and withdraw heated saline to treatment element 322*b*, such as through an energy transfer tube not shown, at a desired temperature and for a desired time period. Controller 360 may be configured for manual control, so that the operator first initiates the energy delivery, then allows the treatment element 322*b* to ablate the tissue for some time period, after which the operator terminates the energy delivery.

System 300 may further include one or more imaging devices, such as imaging device 370. Imaging device 370 may be configured to be inserted into the patient and may comprise a visual light camera; an ultrasound imager; an optical coherence domain reflectometry (OCDR) imager; and/or an optical coherence tomography (OCT) imager, such as when integral to, attached to, contained within and/or proximate to shaft 311*a* and/or 311*b*. Imaging device 370 may be inserted through a separate working channel of endoscope 350, lumen not shown. In one embodiment, imaging device 370 is an ultrasound transducer connected to a shaft, not shown but surrounded by shaft 311*a* and typically rotated and/or translated to create a multi-dimensional image of the area surrounding imaging device 370. Alternatively or additionally, imaging device 370 may be external to the patient, such as an imaging device selected from the group consisting of: an X-ray; a fluoroscope; an ultrasound image; an MRI; a PET Scanner; and combinations of these.

System 300 may further include protective cap 380, configured to be positioned proximate tissue to prevent damage to certain tissue during energy delivery or other tissue treatment event. Protective cap 380 may be delivered with endoscope 350 or another elongate device such that cap 380 can be placed over and then positioned to protect the Ampulla of Vater. In a typical embodiment, protective cap 380 is removed within 24 hours of placement, such as by being removed during the procedure after treatment of the target tissue.

In addition to or as an alternative to fluid delivery assembly 130, system 300 may further include tissue expansion device 390, configured to expand the target tissue area, such as sub-mucosal tissue expanding device, such one or more tissue expansion devices 100 of FIG. 1 or another tissue expansion device described herein in reference to FIGS. 2 through 18. Tissue expansion device 390 may be inserted through endoscope 350 and/or alongside endoscope 350. Tissue expansion can greatly alleviate the need for precision of treatment, such as precision of energy delivery, due to the increased size (e.g. increased depth) of the target tissue and an associated safety zone of tissue to which treatment causes no significant adverse event (e.g. an expanded submucosal layer prior to a mucosal layer ablation).

System 300 may further include one or more pharmaceutical or other agents 500, such as an agent configured for systemic and/or local delivery to a patient. These agents may be delivered, pre-procedurally, peri-procedurally and/or post-procedurally. The agents may be configured to improve healing, such as agents selected from the group consisting of: antibiotics, steroids, mucosal cytoprotective agents such as sucralfate, proton pump inhibitors or other acid blocking drugs; and combinations of these. Alternative or in addition to these agents, pre-procedural and/or post-procedural diets may be employed. Pre-procedural diets may include food intake that is low in carbohydrates and/or low in calories. Post-procedural diets may include food intake that comprise a total liquid diet or a diet that is low in calories and/or low in carbohydrates. In some embodiments, a diuretic or other fluid reducing agent may be delivered to the patient, such as a diuretic delivered after completion of a tissue expansion procedure.

In a typical embodiment, system 300 does not include a chronically implanted component or device, only body inserted devices that are removed at the end of the clinical procedure or shortly thereafter, such as devices removed within 8 hours of insertion, within 24 hours of insertion and/or within one week of insertion. In an alternative embodiment, implant 510 may be included. Implant 510 may comprise one or more of: a stent; a sleeve; and a drug delivery device such as a coated stent, a coated sleeve and/or an implanted pump. In embodiments including an implant, such as implant 510, tissue expansion such as submucosal tissue expansion can be performed to enhance the anchoring of the implant such as to the luminal wall of the gastrointestinal tract.

Each of the components of system 300 may be removably attached to another component, particularly controller 360, energy delivery unit 330, vacuum source 340, motion transfer element 335, ground pad 332 and endoscope 350 and device 301.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A method of expanding tissue comprising:
   providing a tissue expansion device comprising:
   (a) at least one fluid delivery tube comprising a proximal end, a distal end, and a lumen therebetween; and
   (b) at least one fluid delivery element in fluid communication with the at least one fluid delivery tube lumen; and
   delivering a visualizable fluid through the at least one fluid delivery element into a first tissue location in a patient's duodenum to perform a near full circumferential expansion of luminal wall tissue, wherein the visualizable expansion fluid comprises a dye or other visualizable colorant which produces a color when injected into target at said first tissue location; and
   visualizing a color of the first tissue location;
   determining a thickness of the near full circumferential tissue expansion based upon an observed color, wherein a deeper observed color of the visualizable expansion fluid visualized at the target tissue corresponds to a thicker the tissue expansion at the target tissue.

2. The method of claim 1, wherein the visualizable fluid consists essentially of saline and the dye.

3. The method of claim 1, visualizing the color of the first tissue location by comprises using an endoscope camera.

4. The method of claim 1, wherein the at least one fluid delivery element comprises a first fluid delivery element and a second fluid delivery element and wherein the fluid is delivered by injecting the visualizable through the fluid first fluid delivery element and the second fluid delivery element.

5. The method of claim 4, wherein said first fluid delivery element and said second fluid delivery element comprises multiple hollow fluid delivery needles in fluid communication with the at least one fluid delivery tube lumen.

6. The method of claim 5, wherein delivering the visualizable expansion fluid comprises injecting a volume of visualizable expansion fluid sufficient to expand said target tissue through the multiple hollow fluid delivery needles.

7. The method of claim 6, wherein the visualizable expansion is injected through the multiple hollow fluid delivery needles simultaneously.

8. The method of claim 6, wherein the visualizable expansion is injected through the multiple hollow fluid delivery needles sequentially.

9. The method of claim 6, wherein the multiple hollow fluid delivery needle are advanced into the tissue by a fixed distance.

10. The method of claim 1, further comprising drawing a vacuum around the fluid delivery element after the visualizable fluid has been delivered.

11. The method of claim 1, further comprising applying a force to maintain contact between the fluid delivery elements and the tissue.

12. The method of claim 1, further comprising preventing motion of at least a portion of the tissue as at least one of the fluid delivery elements penetrate the tissue.

* * * * *